United States Patent
Desai et al.

(10) Patent No.: US 10,011,609 B2
(45) Date of Patent: Jul. 3, 2018

(54) HETEROCYCLIC COMPOUNDS

(71) Applicant: CADILA HEALTHCARE LIMITED, Ahmedabad, Gujarat (IN)

(72) Inventors: Ranjit C. Desai, Gujarat (IN); Brijeshkumar Srivastava, Gujarat (IN)

(73) Assignee: CADILA HEALTHCARE LIMITED, Ahmedabad, Gujarat (IN)

( * ) Notice: Subject to any disclaimer, the term of this patent is extended or adjusted under 35 U.S.C. 154(b) by 0 days.

(21) Appl. No.: 15/034,661

(22) PCT Filed: Nov. 3, 2014

(86) PCT No.: PCT/IN2014/000704
§ 371 (c)(1),
(2) Date: May 5, 2016

(87) PCT Pub. No.: WO2015/097713
PCT Pub. Date: Jul. 2, 2015

(65) Prior Publication Data
US 2016/0257701 A1     Sep. 8, 2016

(30) Foreign Application Priority Data

Nov. 14, 2013  (IN) .......................... 3577/MUM/2013

(51) Int. Cl.
| | | |
|---|---|---|
| *C07D 513/04* | (2006.01) | |
| *C07D 491/08* | (2006.01) | |
| *A61K 31/404* | (2006.01) | |
| *A61K 31/407* | (2006.01) | |
| *A61K 31/4162* | (2006.01) | |
| *A61K 31/4365* | (2006.01) | |
| *A61K 31/437* | (2006.01) | |
| *A61K 31/439* | (2006.01) | |
| *A61K 31/47* | (2006.01) | |
| *A61K 31/472* | (2006.01) | |
| *A61K 31/4985* | (2006.01) | |
| *A61K 31/519* | (2006.01) | |
| *C07D 215/06* | (2006.01) | |
| *C07D 215/20* | (2006.01) | |
| *C07D 217/04* | (2006.01) | |
| *C07D 471/04* | (2006.01) | |
| *C07D 487/04* | (2006.01) | |
| *C07D 491/04* | (2006.01) | |
| *C07D 207/08* | (2006.01) | |
| *C07D 207/20* | (2006.01) | |
| *C07D 495/04* | (2006.01) | |
| *C07D 498/04* | (2006.01) | |
| *C07D 209/12* | (2006.01) | |
| *A61K 31/40* | (2006.01) | |
| *A61K 31/435* | (2006.01) | |
| *A61K 31/4375* | (2006.01) | |
| *A61K 31/4453* | (2006.01) | |
| *A61K 31/496* | (2006.01) | |
| *C07D 207/06* | (2006.01) | |

(Continued)

(52) U.S. Cl.
CPC ............ *C07D 513/04* (2013.01); *A61K 31/40* (2013.01); *A61K 31/404* (2013.01); *A61K 31/407* (2013.01); *A61K 31/4162* (2013.01); *A61K 31/435* (2013.01); *A61K 31/437* (2013.01); *A61K 31/439* (2013.01); *A61K 31/4365* (2013.01); *A61K 31/4375* (2013.01); *A61K 31/4453* (2013.01); *A61K 31/47* (2013.01); *A61K 31/472* (2013.01); *A61K 31/496* (2013.01); *A61K 31/4985* (2013.01); *A61K 31/519* (2013.01); *C07D 207/06* (2013.01); *C07D 207/08* (2013.01); *C07D 207/20* (2013.01); *C07D 209/08* (2013.01); *C07D 209/12* (2013.01); *C07D 209/44* (2013.01); *C07D 215/06* (2013.01); *C07D 215/20* (2013.01); *C07D 217/04* (2013.01); *C07D 295/096* (2013.01); *C07D 471/04* (2013.01); *C07D 487/04* (2013.01); *C07D 491/04* (2013.01); *C07D 491/048* (2013.01); *C07D 491/08* (2013.01); *C07D 495/04* (2013.01); *C07D 498/04* (2013.01); *C07F 3/00* (2013.01)

(58) Field of Classification Search
USPC .......................... 514/252.14, 254.03, 255.03
See application file for complete search history.

(56) References Cited

U.S. PATENT DOCUMENTS

| | | | |
|---|---|---|---|
| 7,517,910 B2 | 4/2009 | Yasuma et al. | |
| 7,820,837 B2 | 10/2010 | Yasuma et al. | |

(Continued)

FOREIGN PATENT DOCUMENTS

| | | |
|---|---|---|
| EP | 1 731 505 A1 | 12/2006 |
| WO | 2004/011446 A1 | 2/2004 |

(Continued)

OTHER PUBLICATIONS

Prentki, M., et al., "Islet β cell failure in type 2 diabetes", The Journal of Clinical Investigation, Jul. 2006, vol. 116, No. 7, pp. 1802-1812.

(Continued)

*Primary Examiner* — Pancham Bakshi
(74) *Attorney, Agent, or Firm* — Ladas & Parry LLP

(57) ABSTRACT

The present invention relates to novel GPR 40 agonists of the general formula (I), their tautomeric forms, their stereoisomers, their pharmaceutically acceptable salts, pharmaceutical compositions containing them, methods for their preparation, use of these compounds in medicine and the intermediates involved in their preparation.

6 Claims, No Drawings

(51) Int. Cl.
*C07D 209/08* (2006.01)
*C07D 209/44* (2006.01)
*C07D 295/096* (2006.01)
*C07D 491/048* (2006.01)
*C07F 3/00* (2006.01)

(56) References Cited

U.S. PATENT DOCUMENTS

| | | |
|---|---|---|
| 7,968,552 B2 | 6/2011 | Negoro et al. |
| 2006/0004012 A1 | 1/2006 | Akerman et al. |
| 2011/0092531 A1 | 4/2011 | Hamdouchi et al. |
| 2012/0035196 A1 | 2/2012 | Negoro et al. |
| 2014/0038970 A1 | 2/2014 | Josien et al. |
| 2014/0045746 A1 | 2/2014 | Hagmann et al. |
| 2014/0057871 A1 | 2/2014 | Okano et al. |
| 2014/0058125 A1 | 2/2014 | Ulven et al. |
| 2014/0128333 A1 | 5/2014 | Hancke Orozco et al. |
| 2014/0148462 A1 | 5/2014 | Eckhardt et al. |
| 2014/0163025 A1 | 6/2014 | Eckhardt et al. |
| 2014/0221349 A1 | 8/2014 | Eckhardt |
| 2016/0024063 A1* | 1/2016 | Yang .............. C07D 213/74 514/252.14 |

FOREIGN PATENT DOCUMENTS

| | | |
|---|---|---|
| WO | 2005/063729 A1 | 7/2005 |
| WO | 2005/086661 A2 | 9/2005 |
| WO | 2005/095338 A1 | 10/2005 |
| WO | 2006/038738 A1 | 4/2006 |
| WO | 2006/083612 A1 | 8/2006 |
| WO | 2006/083781 A1 | 8/2006 |
| WO | 2007/013679 A1 | 2/2007 |
| WO | 2007/049050 A2 | 5/2007 |
| WO | 2007/123225 A1 | 11/2007 |
| WO | 2007/136572 A2 | 11/2007 |
| WO | 2007/136573 A2 | 11/2007 |
| WO | 2008/002931 A2 | 1/2008 |
| WO | 2008/030520 A1 | 3/2008 |
| WO | 2008/054674 A2 | 5/2008 |
| WO | 2008/054675 A2 | 5/2008 |
| WO | 2008/130514 A1 | 10/2008 |
| WO | 2008/139987 A1 | 11/2008 |
| WO | 2009/038204 A1 | 3/2009 |
| WO | 2009/048527 A1 | 4/2009 |
| WO | 2009/054423 A1 | 4/2009 |
| WO | 2009/058237 A1 | 5/2009 |
| WO | 2010/012650 A1 | 2/2010 |
| WO | 2010/045258 A2 | 4/2010 |
| WO | 2010/085522 A1 | 7/2010 |
| WO | 2010/085525 A1 | 7/2010 |
| WO | 2010/085528 A1 | 7/2010 |
| WO | 2010/091176 A1 | 8/2010 |
| WO | 2011/044073 A1 | 4/2011 |
| WO | 2011/046851 A1 | 4/2011 |
| WO | 2011/052756 A1 | 5/2011 |
| WO | 2011/066183 A1 | 6/2011 |
| WO | 2011/069958 A2 | 6/2011 |
| WO | 2011/078371 A1 | 6/2011 |
| WO | 2011/083752 A1 | 7/2011 |
| WO | 2012/004261 A1 | 1/2012 |
| WO | 2012/010413 A1 | 1/2012 |
| WO | 2012/011125 A1 | 1/2012 |
| WO | 2012/020738 A1 | 2/2012 |
| WO | 2012/074126 A1 | 6/2012 |
| WO | 2012/108478 A1 | 8/2012 |
| WO | 2012/111849 A1 | 8/2012 |
| WO | 2013/025424 A1 | 2/2013 |
| WO | 2013/128378 A1 | 9/2013 |
| WO | 2013/144097 A1 | 10/2013 |
| WO | 2013/144098 A1 | 10/2013 |
| WO | 2013/147443 A1 | 10/2013 |
| WO | 2014/022528 A1 | 2/2014 |
| WO | 2014/073904 A1 | 5/2014 |
| WO | 2014/078608 A1 | 5/2014 |
| WO | 2014/078609 A1 | 5/2014 |
| WO | 2014/078610 A1 | 5/2014 |
| WO | 2014/171762 A1 | 10/2014 |
| WO | 2015/028960 A1 | 3/2015 |

OTHER PUBLICATIONS

Itoh, Y., et al., "Free fatty acids regulate insulin secretion from pancreatic β cells through GPR40", Nature, Mar. 13, 2003, vol. 422, pp. 173-176.

Kotarsky, K, et al., "A human cell surface receptor activated by free fatty acids and thiazolidinedione drugs", Biochemical and Biophysical Research Communications 301, 2003, pp. 406-410.

Brown, A. J., et al., "The Orphan G Protein-coupled Receptors GPR41 and GPR43 Are Activated by Propionate and Other Short Chain Carboxylic Acids", The Journal of Biological Chemistry, Mar. 28, 2003, vol. 278, No. 13, pp. 11312-11319.

Garrido, D.M., et al., "Synthesis and activity of small molecule GPR40 agonists", Bioorganic & Medicinal Chemistry Letters 16, 2006, pp. 1840-1845.

Briscoe, C.P., et al., "Pharmacological regulation of insulin secretion in MIN6 cells through the fatty acid receptor GPR40: identification of agonist and antagonist small molecules", British Journal of Pharmacology, 2006, vol. 148(5), pp. 619-628.

Song, F., et al., "Synthesis and Biological Evaluation of 3-Aryl-3-(4-phenoxy)-propionic Acid as a Novel Series of G Protein-Coupled Receptor 40 Agonists", Journal of Medicinal Chemistry, 2007, vol. 50, No. 12, pp. 2807-2817.

Tikhonova, I.G., et al., "Bidirectional, Iterative Approach to the Structural Delineation of the Functional "Chemoprint" in GPR40 for Agonist Recognition", Journal of Medicinal Chemistry, 2007, vol. 50, No. 13, pp. 2981-2989.

Bharate, S.B., et al., "Discovery of diacylphloroglucinols as a new class of GPR40 (FFAR1) agonists", Bioorganic and Medicinal Chemistry Letters 18, 2008, pp. 6357-6361.

Hu, H., et al., "A novel class of antagonists for the FFAs receptor GPR40", Biochemical and Biophysical Research Communications 390, 2009, pp. 557-563.

Zhou, C., et al., "Discovery of 5-aryloxy-2,4-thiazolidinediones as potent GPR40 agonists", Bioorganic and Medicinal Chemistry Letters 20, 2010, pp. 1298-1301.

Negoro, N., et al., "Discovery of TAK-875: A Potent, Selective, and Orally Bioavailable GPR40 Agonist", ACS Medicinal Chemistry Letters, 2010, 1(6), pp. 290-294.

Christiansen, E., et al., "Structure-Activity Study of Dihydrocinnamic Acids and Discovery of the Potent FFA1 (GPR40) Agonist TUG-469", ACS Medicinal Chemistry Letters, 2010, 1(7), pp. 345-349.

Del Guerra, S., et al., "G-protein-coupled receptor 40 (GPR40) expression and its regulation in human pancreatic islets: The role of type 2 diabetes and fatty acids", Nutrition, Metabolism & Cardiovascular Diseases 20, 2010, pp. 22-25.

Rayasam, G.V., et al., "Identification of Berberine as a Novel Agonist of Fatty Acid Receptor GPR40", Phytotherapy Research 24, 2010, pp. 1290-1263.

Walsh, S. P., et al., "3-Substituted 3-(4-aryloxyaryl)-propanoic acids as GPR40 agonists", Bioorganic and Medicinal Chemistry Letters 21, 2011, pp. 3390-3394.

Bhatt, A., et al., "CoMSIA Study on Substituted Aryl Alkanoic Acid Analogs as GPR40 Agonists", Chem. Biol. Drug Des. 77, 2011, pp. 361-372.

Sasaki, S., et al., "Design, Synthesis, and Biological Activity of Potent and Orally Available G Protein-Coupled Receptor 40 Agonists", journal of Medicinal Chemistry, 2011, pp. 1365-1378.

Houze, J. B., et al., "AMG 837: A potent, orally bioavailable GPR40 agonist", Bioorganic and Medicinal Chemistry Letters 22, 2012, pp. 1267-1270.

Mikami, S., et al., "Discovery of Phenylpropanoic Acid Derivatives Containing Polar Functionalities as Potent and Orally Bioavailable G Protein-Coupled Receptor 40 Agonists for the Treatment of Type 2 Diabetes", Journal of Medicinal Chemistry, Nov. 29, 2011, pp. 3756-3776.

(56) References Cited

OTHER PUBLICATIONS

Brown, S. P., et al., "Discovery of AM-1638: A Potent and Orally Bioavailable GPR40/FFA1 Full Agonist", ACS Medicinal Chemistry Letters, 2012, pp. 726-730.

Negoro, N., et al., "Optimization of (2,3-Dihydro-l-benzofuran-3-yl)acetic Acids: Discovery of a Non-Free Fatty Acid-Like, Highly Bioavailable G Protein-Coupled Receptor 40/Free Fatty Acid Receptor 1 Agonist as a Glucose-Dependent Insulinotropic Agent", Journal of Medicinal Chemistry, 2012, pp. 3960-3974.

Gudla, C.S., et al., "Synthesis, characterization and in vitro biological evaluation of some new 3-substituted 9-(4-aryloxyaryl)-propanoic acids as GPR40 agonists", International Journal of Chemistry and Pharmaceutical Sciences, 2014, vol. 2(5), pp. 852-861.

\* cited by examiner

HETEROCYCLIC COMPOUNDS

CROSS-REFERENCE TO RELATED APPLICATION

This U.S. application claims priority under 35 U.S.C 371 to, and is a U.S. National Phase application of, the International Patent Application No. PCT/IN2014/000704, filed 3 Nov. 2014 which claims priority from India Application No. 3577/MUM/2013 filed on 14 Nov. 2013, the disclosures of which are incorporated in their entirety by reference herein.

FIELD OF INVENTION

The present invention relates to novel GPR 40 agonists of the general formula (I), their tautomeric forms, their stereoisomers, their pharmaceutically acceptable salts, pharmaceutical compositions containing them, methods for their preparation, use of these compounds in medicine and the intermediates involved in their preparation.

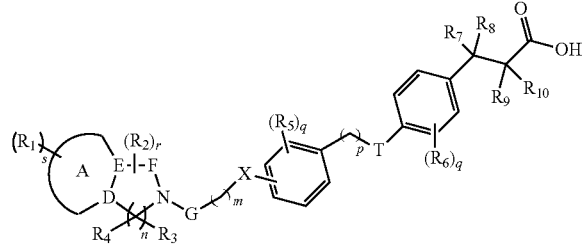

The present invention is directed to G-protein coupled receptor (GPCR) agonists that are useful for the treatment of obesity, diabetes and related metabolic disorders.

The compounds of the general formula (I) lower blood glucose, regulate peripheral satiety, lower or modulate triglyceride levels and/or cholesterol levels and/or low-density lipoproteins (LDL) and raises the high-density lipoproteins. (HDL) plasma levels and hence are useful in combating different medical conditions, where such lowering (and raising) is beneficial. Thus, it could be used in the treatment and/or prophylaxis of obesity, hyperlipidemia, hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as arteriosclerotic cardiovascular diseases, stroke, coronary heart diseases, cerebrovascular diseases, peripheral vessel diseases and related disorders.

These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

About 5% to 10% of the people who have diabetes have IDDM. These individuals don't produce insulin and therefore must inject insulin to keep their blood glucose levels normal. IDDM is characterized by low or undetectable levels of endogenous insulin production caused by destruction of the insulin-producing β cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. N. Engl. J. Med. 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically non-apparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics $3^{rd}$ Ed. 1:1401-1402 (1996)).

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

The G-protein-coupled receptor GPR 40 functions as a receptor for long-chain free fatty acids (FFAs) in the body and as such is implicated in a large number of metabolic conditions in the body. For example it has been alleged that a GPR 40 agonist promotes insulin secretion whilst a GPR 40 antagonist inhibits insulin secretion and so depending upon the circumstances the agonist and antagonist may be useful as therapeutic agents for the number of insulin related conditions such as type 2 diabetes, obesity, impaired glucose tolerance, insulin resistance, neurodegenerative diseases and the like.

There is increasing evidences that lipids can also serve as extracellular ligands for a specific class of receptors and thus act as "nutritional sensors" (Nolan C J et al. J. Clinic. Invest., 2006, 116, 1802-1812 The free fatty acids can regulate cell function. Free fatty acids have demonstrated as ligands for orphan G protein-coupled receptors (GPCRs) and have been proposed to play a critical role in physiological glucose homeostasis.

GPR40, GPR120, GPR41 and GPR43 exemplify a growing number of GPCRs that have been shown to be activated by free fatty acids. GPR40 and GPR120 are activated by medium to long-chain free fatty acids whereas GPR 41 and GPR 43 are activated by short-chain fatty acid (Brown A J et al, 2003).

GPR 40 is highly expressed on pancreatic β-cells, and enhances glucose-stimulated insulin secretion (*Nature*, 2003, 422, 173-176, J. Bio. Chem. 2003; 278, 11303-11311, *Biochem. Biophys. Res. Commun.* 2003, 301, 406-410).

Free fatty acids regulate insulin secretion from pancreatic β cells through GPR40 is reported (*Lett. to Nature* 2003, 422, 173-176).

GlaxoSmithKline Research and Development, US published an article in Bioorg. *Med. Chem. Lett.* 2006, 16, 1840-1845 titled Synthesis and activity of small molecule GPR40 agonists. (Does this describe GW9508?) Another article titled Pharmacological regulation of insulin secretion in MIN6 cells through the fatty aid receptor GPR40: Identification of agonist and antagonist small molecules is reported in
*Br. J. Pharmacol.* 2006, 148, 619-928 from GlaxoSmithKline, USA (Does this describe GW9508?)

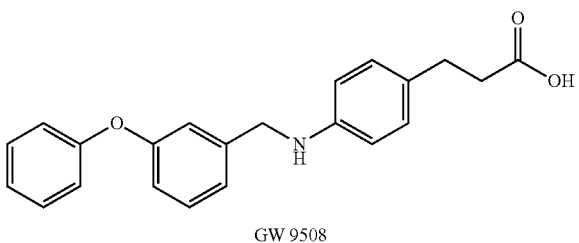 [SMILES: O=C(O)CCc1ccc(NCc2cccc(Oc3ccccc3)c2)cc1]

GW 9508

Solid phase synthesis and SAR of small molecule agonists for the GPR 40 receptor is published in *Bioorg. Med. Chem. Lett.* 2007, 16, 1840-1845 by Glaxo SmithKline Res. & Dev. USA, including those with the following structures.

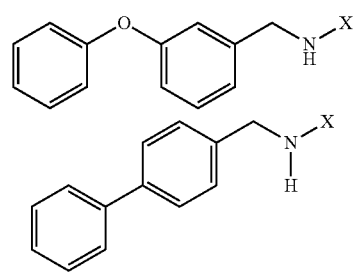

Johnson & Johnson Pharmaceutical Research and development, USA published "Synthesis and Biological Evaluation of 3-Aryl-3-(4-phenoxy)-propanoic acid as a Novel Series of G-protein-coupled receptor 40 agonists (*J. Med. Chem.* 2007, 16, 2807-2817)

National Institutes of Health, Bethesda, Md. published "Bidirectional Iterative Approach to the Structural Delineation of the Functional Chemo print in GPR 40 for agonist Recognition (*J. Med. Chem.* 2007, 50, 2981-2990).

Discovery of diacyl phloroglucinols of the following formula

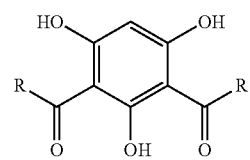

as a new class of GPR40 (FFAR1) agonists has been published by Piramal Life Sciences, Ltd. in *Bioorg. Med. Chem. Left.* 2008, 18, 6357-6361

Synthesis and SAR of 1,2,3,4-tetrahydroisoquinoline-1-ones as novel G-protein coupled receptor40 (GPR40) antagonists of the following formula has been published in *Bioorg. Med. Chem. Lett.* 2009, 19, 2400-2403 by Pfizer

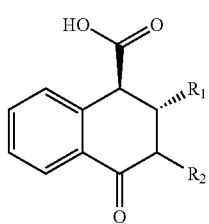

Piramal Life Sciences Ltd. published "Progress in the discovery and development of small molecule modulators of G-protein coupled receptor 40 (GPR40/FFA1/FFAR1), an emerging target for type 2 diabetes" in *Exp. Opin. Therapeutic Patents* 2009, 19(2), 237-264.

There was a report published in *Zhongguo Bingli Shengli Zazhi* 2009, 25(7). 1376-1380 from Sun Yat. Sen University, Guangzhou, which mentions the role GPR 40 on lipoapoptosis.

A novel class of antagonists for the FFA's receptor GPR 40 was published in *Biochem. Biophy. Res. Commun.* 2009, 390, 557-563.

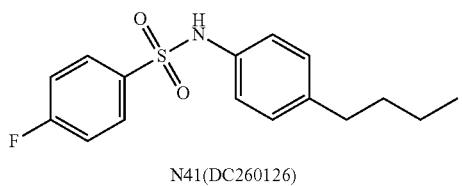 [SMILES: CCCCc1ccc(NS(=O)(=O)c2ccc(F)cc2)cc1]

N41(DC260126)

Merck Res. Laboratories published "Discovery of 5-aryloxy-2,4-thiazolidinediones as potent GPR40 agonists" having the following formula in *Bioorg. Med. Chem. Lett.* 2010, 20, 1298-1301

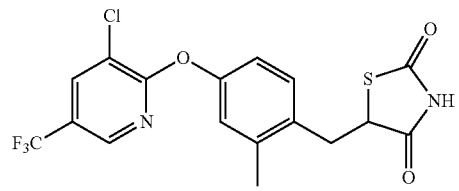 [SMILES: Cc1cc(Oc2ncc(C(F)(F)F)cc2Cl)ccc1CC1SC(=O)NC1=O]

Discovery of TAK-875, a, potent, selective, and orally bioavailable GPR 40 agonist is reported by Takeda Pharmaceutical Ltd. *ACS Med. Chem. Lett.* 2010, 1(6), 290-294

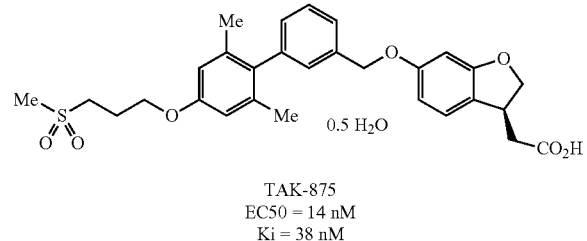 [SMILES: Cc1cc(OCCCS(C)(=O)=O)cc(C)c1-c1cccc(COc2ccc3c(c2)OC[C@H]3CC(=O)O)c1]

TAK-875
EC50 = 14 nM
Ki = 38 nM

In another report from University of Southern Denmark" Structure—Activity of Dihydrocinnamic acids and discovery of potent FFA1 (GPR40) agonist TUG-469" is reported in *ACS Med. Chem. Lett.* 2010, 1(7), 345-349.

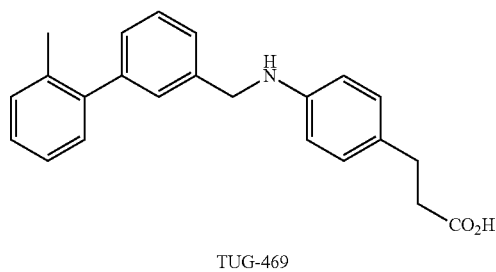 [SMILES: Cc1ccccc1-c1cccc(CNc2ccc(CCC(=O)O)cc2)c1]

TUG-469

The free fatty acid 1 receptor (FFAR1 or GPR40), which is highly expressed on pancreatic β-cells and amplifies glucose-stimulated insulin secretion, has emerged as an attractive target for the treatment of type 2 diabetes (*ACS Med. Chem. Lett.* 2010, 1(6), 290-294).

G-protein coupled receptor (GPR40) expression and its regulation in human pancreatic islets: The role of type 2 diabetes and fatty acids is reported in *Nutrition Metabolism & Cardiovascular diseases* 2010, 20(1), 22-25

Ranbaxy reported "Identification of Berberine as a novel agonist of fatty acid receptor GPR40" in *Phytother Res.* 2010, 24, 1260-63.

The following substituted 3-(4-aryloxyaryl)-propanoic acids as GPR40 agonists are reported by Merck Res. Lab. in *Bioorg. Med. Chem. Lett.* 2011, 21, 3390-3394

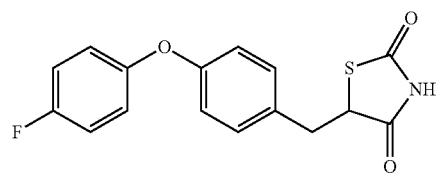

1. $EC_{50}$ = 0.74 μM

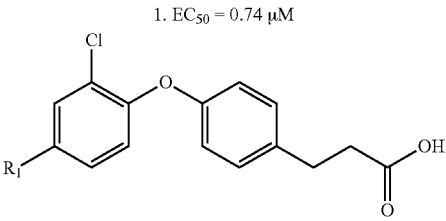

2. $R_1$ = Cl ($EC_{50}$ = 1.358 μM)
3. $R_1$ = $CF_3$ ($EC_{50}$ = 0.686 μM)

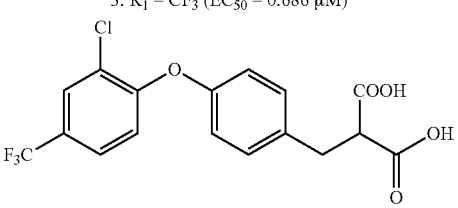

4. $EC_{50}$ = 0.970 μM

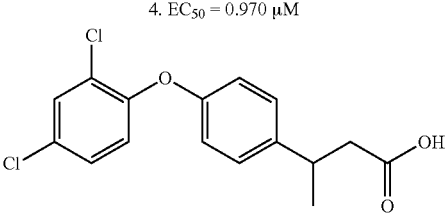

5. $EC_{50}$ = 2.484 μM

CoMSIA study on substituted aryl alkanoic acid analogs as GPR 40 agonists is reported *Chem. Bio. Drug. Des.* 2011, 77, 361-372

Takeda further published "Design, Synthesis and biological activity of potential and orally available G-protein coupled receptor 40 agonists" in *J. Med. Chem.* 2011, 54(5), 1365-1378.

Amgen disclosed a potent orally bioavailable GPR 40 agonist AMG-837 in *Bioorg. Med. Chem. Lett.* 2012, 22, 1267-1270

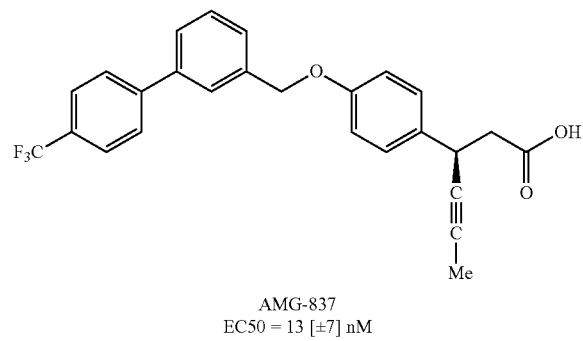 [SMILES: CC#C[C@H](CC(=O)O)c1ccc(OCc2cccc(-c3ccc(C(F)(F)F)cc3)c2)cc1]

AMG-837
EC50 = 13 [±7] nM

Discovery of phenylpropanoic acid derivatives containing polar functionalities as Potent and orally bioavailable G protein-coupled receptor 40 Agonist for the treatment of type 2 Diabetes is reported in *J. Med. Chem.* 2012, 55, 3756-3776 by Takeda.

Discovery of AM-1638: A potent and orally bioavailable GPR40/FFA1 full agonist is reported in *ACS Med. Chem. Lett.* 2012, 3(9), 726-730.

Optimization of (2,3-Dihydro-1-benzofuran-3-yl)acetic acids: Discovery of a Non-free Fatty acid like, highly bioavailable G protein-coupled receptor 40/free acid receptor 1 agonist as a glucose-dependent insulinotropic agent is reported by Takeda in *J. Med. Chem.* 2012, 5, 3960-3974.

Bayer disclosed indane, dihydrobenzofuran, and tetrahydronaphthalene carboxylic acid derivatives and their use as antidiabetics in patent application no. WO 2004011446 with the following formulae

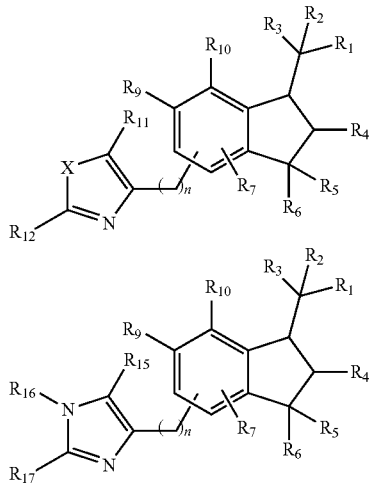

Takeda disclosed 3-(4-Benzyloxyphenyl) propanoic acid derivatives in a patent WO 2005063729 with the following general formula:

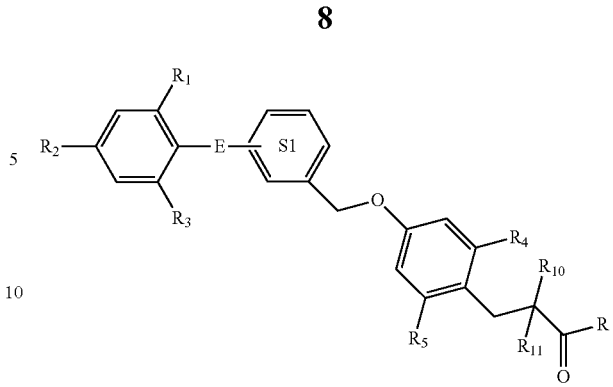

WO 2005086661 A1 (22 Sep. 2005, Amgen Inc.) disclosed compounds, pharmaceutical compositions and methods for use in treating metabolic disorders, having the following formula:

$$Q-L^1-P-L^2-M-X-L^3-A$$

US 2006/0004012, Akerman et al. disclosed certain compounds, pharmaceutical compositions and methods for use in treating metabolic disorders, the said compounds being GPR 40 agonists.

WO 06/038738 A1 (13 Apr. 2006, Takeda Pharmaceutical Ltd., Japan) disclosed certain receptor function regulating agent with the following general structure

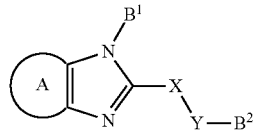

Merck & Co. disclosed antidiabetic bicyclic compounds in WO2006083781. Disclosed therein are bicyclic compounds containing a phenyl or pyridyl ring fused to a cycloalkyl or heterocyclic ring, to which is attached a 5-membered heterocyclic ring, including pharmaceutically acceptable salts and prodrugs thereof, as agonists of G protein coupled receptor 40 (GPR40) and are useful as therapeutic compounds, particularly in the treatment of Type 2 diabetes mellitus, and of conditions that are often associated with the disease, including obesity and lipid disorders, such as mixed or diabetic dyslipidemia, hyperlipidemia, hypercholesterolemia, and hypertriglyceridemia are disclosed.

Merck & Co., in another patent application WO 2006083612 disclosed antidiabetic bicyclic compounds, wherein, the bicyclic compounds contain a fused pyridine ring including pharmaceutically acceptable salts and prodrugs thereof, as agonists of G protein coupled receptor 40 (GPR40) and are useful as therapeutic compounds, particularly in the treatment of Type 2 diabetes mellitus, and of conditions that are often associated with the disease, including obesity and lipid disorders, such as mixed or diabetic dyslipidemia, hyperlipidemia, hypercholesterolemia, and hypertriglyceridemia. The compounds disclosed in the patent application has the following general structure:

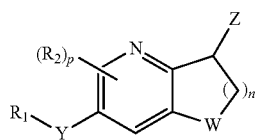

wherein Z is selected from the group consisting of $CR_3R_4CO_2R_5$, —$OCR_3R_4CO_2R_5$, $N(R_6)(CR_3R_4CO_2R_5)$, —$SCR_3R_4CO_2R_5$, tetrazole, and the heterocyclic ring II.

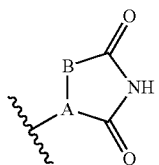

Condensed ring compounds have been disclosed by Yasum et al. in a U.S. Pat. No. 7,820,837. The following formula mentioned in U.S. Pat. No. 7,517,910 claims compounds having a GPR 40 receptor function modulating action, which are useful as insulin secretagogues, agents for the prophylaxis or treatment of diabetes and the like

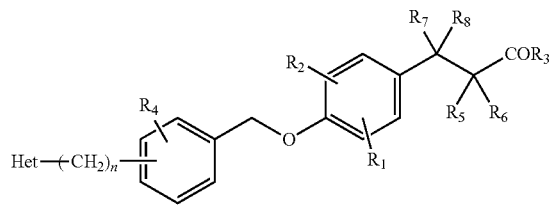

Novel Spiropiperidine compounds have been mentioned by Eli Lilly & Company in WO 2011066183

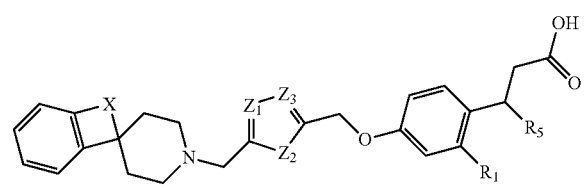

Eli Lilly also disclosed the following Spiropiperidines in patent application no. US20110092531

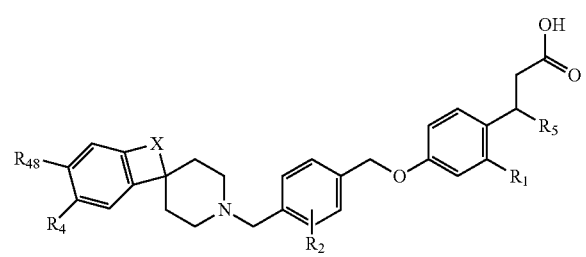

Novel 1,2,3,4-tetrahydroquinoline derivatives useful for the treatment of diabetes have been described by Eli Lilly & Company in patent application no. WO 2013025424

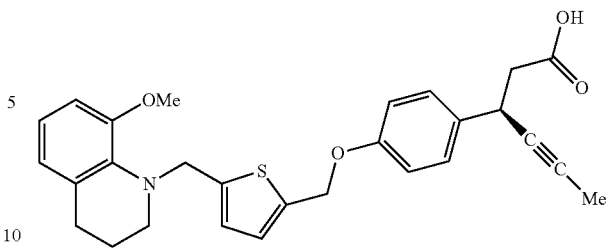

A patent application, WO 2013147443 titled "Preparation of β-substituted carboxylic acid derivatives for the treatment of diabetes" has been published by Daichi Sankyo.

Piramal Enterprises Limited has published a patent application no. WO 2013/128378 for phenyl alkanoic acid derivatives as GPR agonists with the structure below

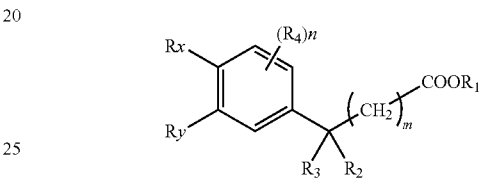

Boehringer Ingelheim has published patent application numbers WO 2013/144097 & WO 2013/144098 titled "New indanyloxy dihydrobenzofuranyl acetic acid derivatives and their use as GPR receptor agonists" with the structures defined below

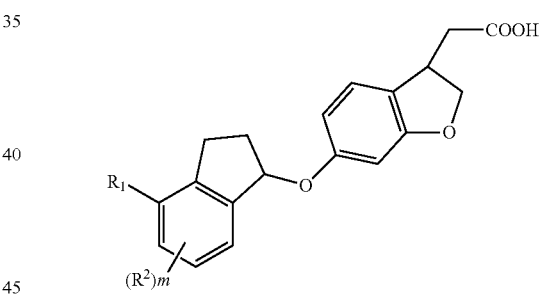

Novel therapeutic target for treatment of cancers and related therapies and methods are disclosed in patent application no. WO 2014145817 by Children's Medical Center Corporation.

WO 2014146604 disclosed certain fused ring compounds having GPR40 receptor function regulating action.

Tricyclic compound and use thereof has been published by SK Chemicals Co., Ltd. in patent application no. WO2014133361.

Certain antidiabetic bicyclic compounds have been disclosed in patent application no. WO2014130608.

Boehringer Ingelheim International disclosed certain other indanyloxy dihydrobenzofuranyl acetic acids in patent application nos. WO2013164292, WO2014122067, WO2014086712, and WO2014082918 & US20140148462, US20140221349 & US20140163025.

Takeda Pharmaceutical Company Limited have disclosed, fused cyclic compounds as GPR40 receptor modulators in a patent application no. EP2743268. Bristol-Myers Squibb has disclosed Dihydropyrazole GPR40 modulators in patent application nos. WO2014078611, WO2014078610, WO2014078609 & WO2014078608.

LG Life Sciences Limited has disclosed certain GPR40 receptor agonist in patent WO2014073904. Hancke Orozco et al. have disclosed compounds, compositions, and methods for decreasing intestinal glucose uptake and inducing incretin release in patent application no. US20140128333. Merck Sharp & Dohme Corp. disclosed antidiabetic tricyclic compounds in patents application nos. US20140045746, WO2014022528 and in another application disclosed certain bridged and fused antidiabetic compounds in patent US 20140038970.

Novel fluoro-substituted compounds capable of modulating the G-protein coupled receptor GPR40 have been disclosed in patent application no. US20140058125.

Mochida Pharmaceutical Co. has disclosed Cyclic amide derivative in patent US20140057871. Negoro et al. have disclosed certain carboxylic acid compounds in patent application no. US20120035196. Several other patent applications have disclosed a varied number of compounds as GPR40 modulators. Some of the representative literature is provided below:

Chandra Sekhar Gudla et al have disclosed some new 3-substituted 3-(aryloxyaryl)-propanoic acid in IJCPS, 2014, Vol. 2(5), 852-861.

WO 2005095338, WO 2006038738, WO 2006083612, WO 2006083781, WO 2007013679, WO 2007136572, WO 2007136573. WO 2007049050. WO 20070123225, WO 2008002931, WO 2008054674, WO 2008054675. WO 200830520, WO 2008130514, WO 2008139987, WO 2009058237, WO 2009048527, WO 2009054423, U.S. Pat. No. 7,968,552, WO 2009038204. WO 2010045258. WO 2010012650, WO 2010085522, WO 2010085525, WO 2010085528, WO 2010091176, WO 2011044073, WO 2011052756, WO 2011078371, WO 2011069958, WO 2011083752, WO 2012111849, WO 2012108478, WO 2012074126, WO 2012020738, WO 2012004261, WO 2012010413, WO 2012010413, WO 2012011125 etc.

Drugs aimed at the pathophysiology associated with insulin dependent Type I diabetes and non-insulin dependent Type II diabetes have many potential side effects and do not adequately address the dyslipidemia and hyperglycemia in a high proportion of patients. Treatment is often focused at individual patient needs using diet, exercise, hypoglycaemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and microvascular disease is an established morbidity associated with untreated or poorly controlled metabolic syndrome.

There is a continuing need for novel antiobesity and antidiabetic agents, particularly ones that are well tolerated with few adverse effects.

The present invention is directed to agonists of GPR 40 that are useful for the treatment of diabetes. In humans, GPR 40 is expressed in the pancreas. As discussed above, several GPR 40 agonists have been developed and are continuing to be developed. However, the therapeutic potential of these compounds to treat diseases has not yet been proved and so there remains the need to develop newer medicines which are better or of comparable efficacy with the present treatment regimes, have lesser side effects and require a lower dosage regime.

We herein disclose novel compounds of formula (I) useful as antidiabetic, anti-obesity, hypolipidaemic, hypolipoproteinemic, and antihyperglycemic agents which may have beneficial effect in the treatment and/or prophylaxis of diseases caused by hyperlipidemia, diseases classified under Syndrome X and atherosclerosis, and methods for their preparation.

SUMMARY OF THE INVENTION

The main objective of the present invention is to provide novel GPR40 agonists represented by the general formula (I), their tautomeric forms, their stereoisomers, their pharmaceutically acceptable salts, and pharmaceutical compositions containing them or their mixtures thereof.

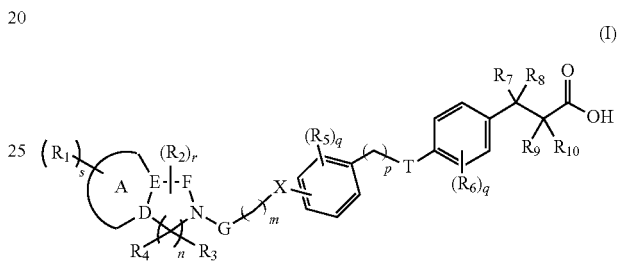

(I)

In an embodiment of the present invention is provided processes for the preparation of compounds represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

In yet another embodiment is provided a pharmaceutical composition comprising the compound of formula (I) and a second suitable therapeutic agent for the treatment of diabetes, obesity and other related disorders.

DETAILED DESCRIPTION OF THE INVENTION

Accordingly, the present invention relates to compounds of the general formula (I)

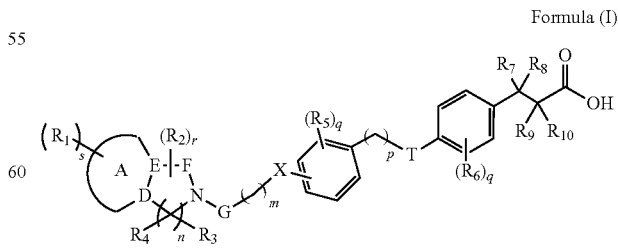

Formula (I)

their tautomeric forms, their stereoisomers, their pharmaceutically acceptable salts, and pharmaceutical compositions containing them wherein each of $R_1$, $R_2$, $R_3$, $R_4$, $R_5$, $R_6$, at each occurrence independently represents H, halogen, hydroxyl, CN, $NO_2$, CHO, COOH, CO, optionally substituted groups selected from, alkyl, alkoxy, thiol, sulphoxide, sulphone, acyl, $NH_2$ or optionally substituted NHCO-linear or branched ($C_1$-$C_6$) alkyl, aralkyl, cycloalkyl, cycloalkylalkyl, heterocyclyl, hetererocyclylalkyl, heteroaryl, heteroaralkyl or the groups OR, C(O)OR, C(O)R, and $SO_2$R wherein 'R' at each occurrence independently represents optionally substituted groups selected from H, linear or branched ($C_1$-$C_6$)alkyl, aryl, aralkyl, cycloalkyl, cycloalkylalkyl, heterocyclyl, hetrerocyclylalkyl, heteroaryl, heteroaralkyl groups; In an alternate embodiment.

$R_3$ and $R_4$ together may form an oxo group;

'A' is selected from 3-7 member partially saturated, unsaturated or saturated ring which may further be having one or more than one heteroatom selected from O, S, or N;

Each of 'E' & 'D' may independently be either nitrogen or carbon. 'F' may be selected from C, N or O; 'G' may be present or absent and when present represents either a bond or is selected from O, S, $NR_a$, wherein '$R_a$' represents linear or branched ($C_1$-$C_6$) alkyl;

m=1-3; each of 'n', 'r', 'p' and 's' independently represents an integer ranging from 0 to 6; q=0-4;

'X' may be present or absent and when present is selected from $CH_2$, O, S, and $NR_a$, $SO_2NH$; wherein $R_a$ is as defined earlier;

'T' is selected from oxygen, —NH, S, SO, $SO_2$ or $NR_a$, wherein $R_a$ is as defined earlier; each of $R_7$ and $R_8$ independently may be selected ($C_2$-$C_4$)alkyne, nitrile, or a cycloalkyl; Alternatively $R_7$ and $R_8$ may combine with the carbon atom to which is attached to form a 3-7 membered cyclic ring which may optionally further have one or more than one heteroatom selected from S, N, or O;

$R_9$ & $R_{10}$ may be selected from hydrogen, alkyl, alkoxy, and halogen groups.

A preferred embodiment of the present invention relates to compound of the general Formula (I')

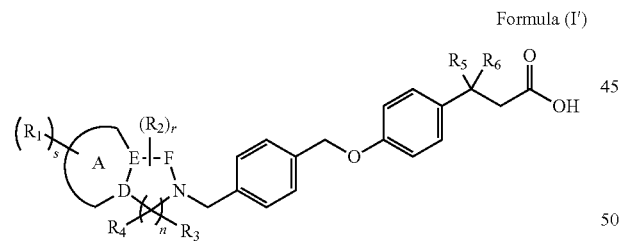

Formula (I')

their tautomeric forms, their stereoisomers, their pharmaceutically acceptable salts, and pharmaceutical compositions containing them wherein Each of $R_1$, $R_2$, $R_3$ and $R_4$ at each occurrence independently represents H, halogen, hydroxyl, CN, $NO_2$, CHO, COOH, CO, optionally substituted groups selected from, alkyl, alkoxy, thiol, sulphoxide, sulphone, acyl, $NH_2$ or optionally substituted NHCO-linear or branched ($C_1$-$C_6$) alkyl, aralkyl, cycloalkyl, cycloalkylalkyl, heterocyclyl, hetererocyclylalkyl, heteroaryl, heteroaralkyl or the groups OR, C(O)OR, C(O)R, and $SO_2$R wherein 'R' at each occurrence independently represents optionally substituted groups selected from H, linear or branched ($C_1$-$C_6$)alkyl, aryl, aralkyl, cycloalkyl, cycloalkylalkyl, heterocyclyl, hetrerocyclylalkyl, heteroaryl, heteroaralkyl groups;

In an alternate embodiment, $R_3$ and $R_4$ together may form an oxo group;

'A' is selected from 3-7 member partially saturated, unsaturated or saturated ring which may further be having one or more than one heteroatom selected from O, S, or N;

Each of 'E' & 'D' may independently be either nitrogen or carbon. 'F' may be selected from C, N or O;

Each of 'n', 'r' and 's' independently represents an integer ranging from 0 to 6;

each of $R_5$ and $R_6$ independently may be selected ($C_2$-$C_4$)alkyne, nitrile, or a cycloalkyl; Alternatively $R_5$ and $R_6$ may combine with the carbon atom to which it is formed to form a 3-7 membered cyclic ring which may optionally further have one or more than one heteroatom selected from S, N, or O;

The preferred heterocycles representing

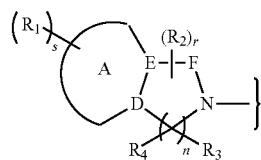

may be selected from the following bicyclic rings mentioned below

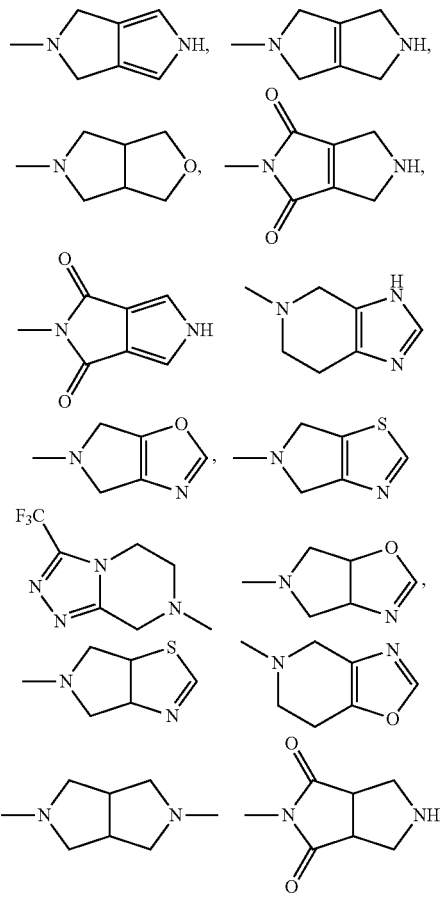

15
-continued
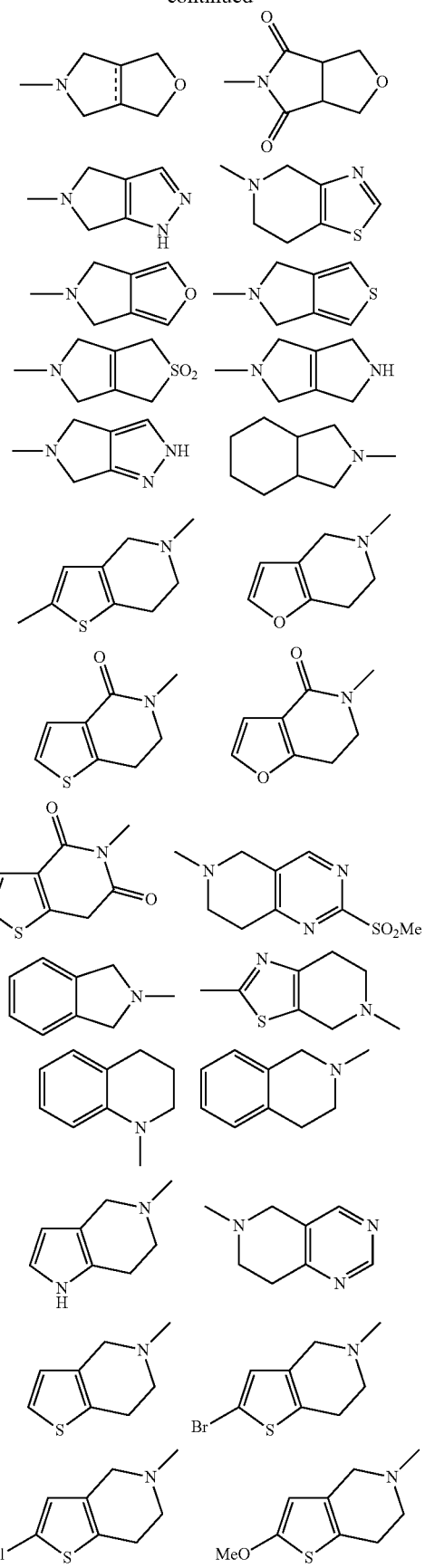
16
-continued
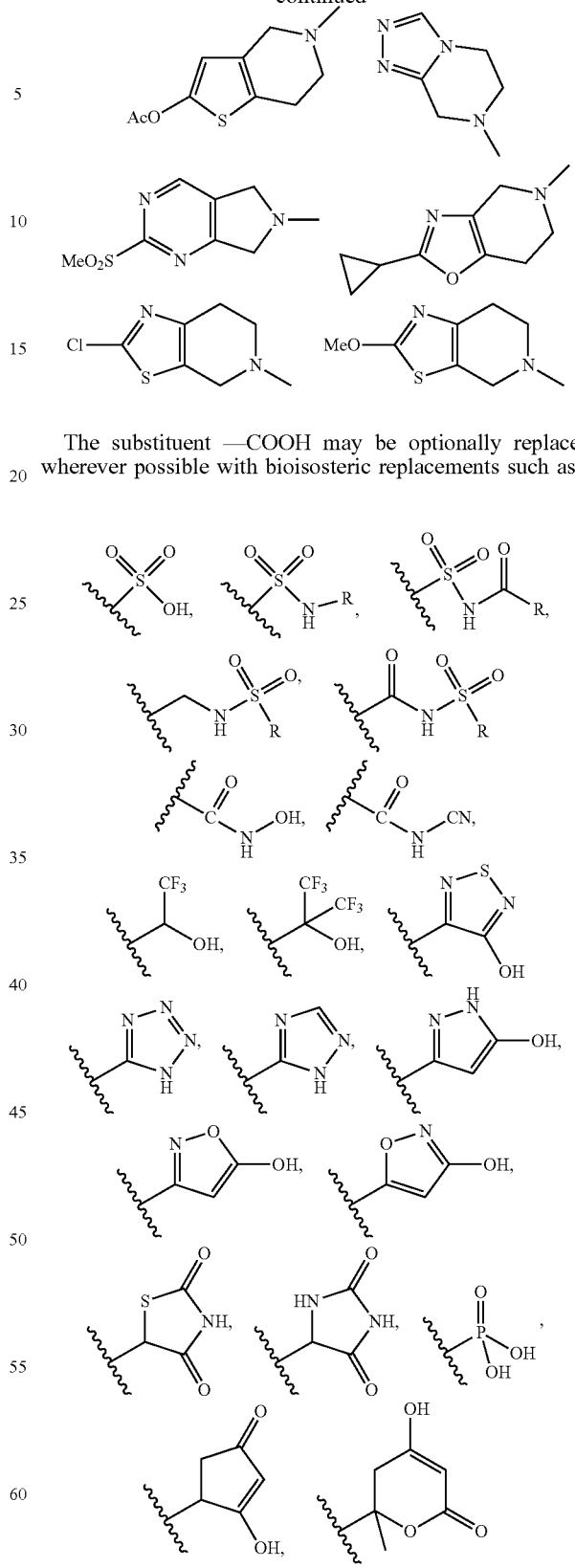
The substituent —COOH may be optionally replaced wherever possible with bioisosteric replacements such as:
and the like;
When any of the groups from $R_1$ to $R_{10}$ are substituted with one or many groups, the substituents may be independently selected from the groups comprising hydroxyl, oxo, halo, thio, nitro, amino, cyano, formyl, or substituted or unsubstituted groups selected from amidino, alkyl, haloalkyl, alkoxy, haloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxyl amino, sulfenyl derivatives, sulfonyl derivatives, sulfonic acid and its derivatives.

The aryl group may be an aromatic system containing one, two or three rings wherein such rings may be attached together in a dependent manner or may be fused; in a preferred embodiment such aryl group may be selected from phenyl, naphthyl, tetrahydronaphthyl, indane, biphenyl groups;

The heteroaryl group represents 5 to 8 membered aromatic radicals, which may be single or fused containing one or more hetero atoms selected from O, N or S; in a preferred embodiment such groups may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzopyranonyl, benzofuranyl, benzothienyl, indolinyl, indolyl, azaindolyl, azaindolinyl, benzodihydrofuranyl, benzodihydrothienyl, pyrazolopyrimidinyl, pyrazolopyrimidonyl, azaquinazolinyl, azaquinazolinoyl, pyridofuranyl, pyridothienyl, thienopyrimidyl, thienopyrimidonyl, quinolinyl, pyrimidinyl, pyrazolyl, quinazolinyl, quinazolonyl, pyrimidonyl, pyridazinyl, triazinyl, benzoxazinyl, benzoxazinonyl, benzothiazinyl, benzothiazinonyl, benzoxazolyl, benzothiazolyl, benzimidazolyl, benzotriazolyl, phthalazynil, naphthylidinyl, purinyl, carbazolyl, phenothiazinyl, phenoxazinyl groups;

The term "heterocyclyl" represents saturated, partially saturated or unsaturated ring-shaped radicals, the heteroatoms being selected from nitrogen, sulfur or oxygen; in a preferred embodiment such groups may be selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, and the like; examples of partially saturated heterocyclic radicals include dihydrothiophene, dihydropyran, dihydrofuran, dihydrothiazole groups.

The "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;

the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains;

the "alkynyl" group used either alone or in combination with other radicals, is selected from a linear or branched radical containing two to six carbon atoms, more preferably thienyl, 1-propynyl, 2-propynyl, 1-butynyl, 2-butynyl, 3-butynyl, 1-pentynyl, 2-pentynyl, 3-pentynyl, 4-pentynyl, 1-hexynyl, and the like. The term "alkynyl" includes di- and tri-ynes;

the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like; The terms "bicycloalkyl" means more than one cycloalkyl groups fused together;

the "cycloalkenyl" group used either alone or in combination with other radicals, are preferably selected from cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl and the like;

the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "cycloalkoxy" group used either alone or in combination with other radicals, is selected from groups containing an cycloalkyl radical, as defined above, attached directly to an oxygen atom, more preferably groups selected from cyclopropoxy, cyclobutoxy, cyclopentyloxy, cyclohexyloxy, cycloheptyloxy and the like;

the "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like;

the "aralkyl" group used either alone or in combination with other radicals, is selected from groups containing an aryl radical, as defined above, attached directly to an alkyl radical, as define above, more preferably groups selected from benzyl, phenethyl, and the like;

the "aralkoxy" group used either alone or in combination with other radicals, is selected from groups containing an aralkyl radical, as defined above, attached directly to an oxygen atom, more preferably groups selected from benzyloxy, phenethyloxy, and the like;

the "heteroaralkyl" group used either alone or in combination with other radicals, is selected from groups containing an heteroaryl radical, as defined above, attached directly to an alkyl radicals, as define above, more preferably groups selected from pyridinealkyl, thiophenealkyl, quinolinealkyl, and the like;

the "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like;

the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "haloalkoxy" group is selected from suitable haloalkyl, as defined above, directly attached to an oxygen atom, more preferably groups selected from fluoromethoxy, chloromethoxy, fluoroethoxy, chloroethoxy and the like:

the "perhaloalkoxy" group is selected from a suitable perhaloalkyl radical, as defined above, directly attached to an oxygen atom, more preferably groups selected from trifluoromethoxy, trifluoroethoxy, and the like;

the groups "heteroaryloxy", "heteroaralkoxy", "heterocycloxy", "heterocylylalkoxy" are selected from suitable heteroaryl, heteroarylalkyl, heterocyclyl, heterocylylalkyl groups respectively, as defined above, attached to an oxygen atom;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;

the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;

the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted;

the "mono-substituted amino" group used either alone or in combination with other radicals, represents an amino group substituted with one group selected from ($C_1$-$C_6$)alkyl, substituted alkyl, aryl, substituted aryl or arylalkyl groups as defined earlier, more preferably such groups are selected from methylamine, ethylamine, n-propylamine, n-butylamine, n-pentylamine and the like;

the 'disubstituted amino" group used either alone or in combination with other radicals, represents an amino group, substituted with two radicals that may be same or different selected from ($C_1$-$C_6$)alkyl, substituted alkyl, aryl, substituted aryl, or arylalkyl groups, as defined above, more preferably the groups are selected from dimethylamino, methylethylamino, diethylamino, phenylmethyl amino and the like;

the "arylamino" used either alone or in combination with other radicals, represents an aryl group, as defined above, linked through amino having a free valence bond from the nitrogen atom, more preferably the groups are selected from phenylamino, naphthylamino, N-methyl anilino and the like;

the "oxo" or "carbonyl" group used either alone (—C═O—) or in combination with other radicals such as alkyl-described above, for e.g. "alkylcarbonyl", denotes a carbonyl radical (—C═O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N$—C═O), wherein the amino group is mono- or di-substituted or unsubstituted, more preferably the groups are selected from methyl amide, dimethyl amide, ethyl amide, diethyl amide, and the like;

the "aminocarbonyl" group used either alone or in combination with other radicals, may be selected from 'aminocarbonyl', 'aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote amiocarbonyl radicals substituted, respectively, with one aryl radical, or one alkyl, and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic alkylthio selected from cyclopropylthio, cyclobutylthio, cyclopentylthio, cyclohexylthio and the like, which may be optionally substituted;

the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonylamino", "alkylaminocarbonylamino", "dialkylaminocarbonylamino" groups used alone or in combination with other radicals, is a carbonylamino (—CONH$_2$) group, attached to amino(NH$_2$), alkylamino group or dialkylamino group respectively, where alkyl group is as defined above;

the "amidino" group used either alone or in combination with other radicals, represents a —C(=NH)—NH$_2$ radical; the "alkylamidino" group represents an alkyl radical, as described above, attached to an amidino group;

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group. —SO— or R$_x$SO, where Rx is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —SO$_2$—, or R$_x$SO$_2$—, where R$_x$ is as defined above.

ore preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

the "sulfonyloxy" group used either alone or in combination with other radicals, with other terms such as alkylsulfonyloxy, represents a divalent radical —SO$_3$—, or R$_x$SO$_3$—, where R$_x$ is as defined above. More preferably, the groups may be selected from "alkylsulfonyl" wherein suitable alkyl radicals, selected from those defined above, is attached to a sulfonyloxy radical, such as methanesulfonyloxy, ethanesulfonyloxy, propanesulfonyloxy and the like. "arylsulfonyl" wherein an aryl radical, as defined above, is attached to a sulfonyl radical, such as benzenesulfonyloxy and the like Suitable groups and substituents on the groups may be selected from those described anywhere in the specification.

Particularly useful compounds may be selected from
(S)-3-(4-((3-((6,7-dihydrothieno[3,2-c]pyridin-5(4H)-yl) methyl)benzyl)oxy)phenyl)hex-4-ynoic acid (1);

Lithium 3-(4-((3-((4H-furo[3,4-c]pyrrol-5(6H)-yl)methyl) benzyl)oxy)phenyl)-3-cyanopropanoic acid;

3-cyano-3-(4-((3-((4-oxo-6,7-dihydrothieno[3,2-c]pyridin-5 (4H)-yl)methyl)benzyl)oxy)phenyl)propanoic acid;

Lithium 3-cyano-3-(4-((3-((3-(trifluoromethyl)-5,6-dihydro-[1,2,4]triazolo[4,3-a]pyrazin-7(8H)-yl)methyl) benzyl)oxy)phenyl)propanoic acid;

3-cyano-3-(4-((3-((2,2-dioxido-1H-thieno[3,4-c]pyrrol-5 (3H,4H,6H)-yl)methyl)benzyl)oxy)phenyl)propanoic acid;

3-cyano-3-(4-((3-((6,7-dihydrothieno[3,2-c]pyridin-5(4H)-yl)methyl)benzyl)oxy)phenyl)propanoic acid;

(S)-3-(4-((3-((2-methyl-6,7-dihydrothieno[3,2-c]pyridin-5 (4H)-yl)methyl)benzyl)oxy)phenyl)hex-4-ynoic acid;

(S)-3-(4-((3-((1-(tert-butoxycarbonyl)-6,7-dihydro-1H-pyrrolo[3,2-c]pyridin-5(4H)-yl)methyl)benzyl)oxy)phenyl) hex-4-ynoic acid;

(S)-3-(4-((3-((6,7-dihydro-1H-pyrrolo[3,2-c]pyridin-5(4H)-yl)methyl)benzyl)oxy)phenyl)hex-4-ynoic acid;

(S)-3-(4-((3-((2-methyl-6,7-dihydrothiazolo[5,4-c]pyridin-5 (4H)-yl)methyl)benzyl)oxy)phenyl)hex-4-ynoic acid;

(S)-3-(4-((3-((3-(trifluoromethyl)-5,6-dihydro-[1,2,4]triazolo[4,3-a]pyrazin-7(8H)-yl)methyl)benzyl)oxy)phenyl)hex-4-ynoic acid;

(S)-3-(4-((3-(isoindolin-2-ylmethyl)benzyl)oxy)phenyl) hex-4-ynoic acid;

(S)-3-(4-((3-((3,4-dihydroquinolin-1(2H)-yl)methyl)benzyl)oxy)phenyl)hex-4-ynoic acid;

(S)-3-(4-((3-((2-bromo-6,7-dihydrothieno[3,2-c]pyridin-5 (4H)-yl)methyl)benzyl)oxy)phenyl)hex-4-ynoic acid;

(S)-3-(4-((3-((3,4-dihydroisoquinolin-2(1H)-yl)methyl)benzyl)oxy)phenyl)hex-4-ynoic acid;

calcium(S)-3-(4-((3-((2-methyl-6,7-dihydrothieno[3,2-c] pyridin-5(4H)-yl)methyl)benzyl)oxy)phenyl)hex-4-ynoate(S)-3-(4-((3-((2-methyl-6,7-dihydrothieno[3,2-c]pyridin-5(4H)-yl)methyl)benzyl)oxy)phenyl)hex-4-ynoate;

calcium (S)-3-(4-((3-((2-methyl-6,7-dihydrothiazolo[4,5-c] pyridin-5(4H)-yl)methyl)benzyl)oxy)phenyl)hex-4-ynoate(S)-3-(4-((3-((2-methyl-6,7-dihydrothiazolo[4,5-c] pyridin-5(4H)-yl)methyl)benzyl)oxy)phenyl)hex-4-ynoate;

(S)-3-(4-((3-((2-(Difluoromethyl)-6,7-dihydrothieno[3,2-c] pyridin-5(4H)-yl)methyl)benzyl)oxy)phenyl)hex-4-ynoic acid;

Calcium (S)-3-(4-((3-((2-bromo-6,7-dihydrothieno[3,2-c] pyridin-5(4H)-yl)methyl)benzyl)oxy)phenyl)hex-4-ynoate;

Calcium (S)-3-(4-((3-((3,4-dihydroisoquinolin-2(1H)-yl) methyl)benzyl)oxy)phenyl)hex-4-ynoate;

(S)-3-(4-((3-((7,8-Dihydropyrido[4,3-d]pyrimidin-6(5H)-yl)methyl)benzyl)oxy)phenyl)hex-4-ynoic acid;

(S)-3-(4-((3-((1-Methylpyrrolo[3,4-c]pyrazol-5(1H,4H, 6H)-yl)methyl)benzyl)oxy)phenyl)hex-4-ynoic acid;

(3S)-3-(4-((3-(6-Oxa-3-azabicyclo[3.1.1]heptan-3-ylmethyl)benzyl)oxy)phenyl)hex-4-ynoic acid;

(S)-3-(4-((3-(Indolin-1-ylmethyl)benzyl)oxy)phenyl)hex-4-ynoic acid;

(S)-3-(4-((3-((5,6-Dihydro-[1,2,4]triazolo[4,3-a]pyrazin-7 (8H)-yl)methyl)benzyl)oxy)phenyl)hex-4-ynoic acid;

(S)-3-(4-((3-((2-Cyclopropyl-6,7-dihydrooxazolo[4,5-c] pyridin-5(4H)-yl)methyl)benzyl)oxy)phenyl)hex-4-ynoic acid;

(3S)-3-(4-((3-((5-Benzylhexahydropyrrolo[3,4-c]pyrrol-2 (1H)-yl)methyl)benzyl)oxy)phenyl)hex-4-ynoic acid compound with formic acid;

(S)-3-(4-((3-((4H-Thieno[2,3-c]pyrrol-5(6H)-yl)methyl) benzyl)oxy)phenyl)hex-4-ynoic acid;

6-(3-((4-((S)-1-carboxypent-3-yn-2-yl)phenoxy)methyl)
benzyl)-6,7-dihydro-5H-pyrrolo[3,4-d]pyrimidin-6-ium
formate;
1-(3-((4-((S)-1-carboxypent-3-yn-2-yl)phenoxy)methyl)
benzyl)-7-methoxy-1,2,3,4-tetrahydroquinolin-1-ium formate;
(S)-3-(4-((3-((2-Chloro-6,7-dihydrothiazolo[5,4-c]pyridin-5(4H)-yl)methyl)benzyl)oxy)phenyl)hex-4-ynoic acid;
(S)-3-(4-((3-((2-Bromo-6,7-dihydrothiazolo[5,4-c]pyridin-5(4H)-yl)methyl)benzyl)oxy)phenyl)hex-4-ynoic acid;
(S)-3-(4-((3-(pyrrolo[3,4-c]pyrazol-5(1H,4H,6H)-ylmethyl)benzyl)oxy)phenyl)hex-4-ynoic acid;
(S)-3-(4-((3-((2-(hydroxymethyl)-6,7-dihydrothieno[3,2-c]pyridin-5(4H)-yl)methyl)benzyl)oxy)phenyl)hex-4-ynoic acid;
(S)-5-(3-((4-(1-carboxypent-3-yn-2-yl)phenoxy)methyl)benzyl)-4,5,6,7-tetrahydrothieno[3,2-c]pyridine-2-carboxylic acid;
3-cyclopropyl-3-(3-((3-((2-methyl-6,7-dihydrothieno[3,2-c]pyridin-5(4H)-yl)methyl)benzyl)oxy)phenyl)propanoic acid;
(S)-3-(4-((3-((1-methyl-6,7-dihydro-1H-pyrrolo[3,2-c]pyridin-5(4H)-yl)methyl)benzyl)oxy)phenyl)hex-4-ynoic acid;
(S)-3-(4-((3-((2-amino-6,7-dihydrothiazolo[5,4-c]pyridin-5(4H)-yl)methyl)benzyl)oxy)phenyl)hex-4-ynoic acid;
Calcium (S)-3-(4-((3-((2-chloro-6,7-dihydrothieno[3,2-c]pyridin-5(4H)-yl)methyl)benzyl)oxy)phenyl)hex-4-ynoate;
(S)-3-(4-((3-((2-carbamoyl-6,7-dihydrothieno[3,2-c]pyridin-5(4H)-yl)methyl)benzyl)oxy)phenyl)hex-4-ynoic acid;
(S)-3-(4-((3-((2-isopropylpyrrolo[3,4-c]pyrazol-5(2H,4H,6H)-yl)methyl)benzyl)oxy)phenyl)hex-4-ynoic acid;
(S)-3-(4-((3-((2-(methoxycarbonyl)-6,7-dihydrothieno[3,2-c]pyridin-5(4H)-yl)methyl)benzyl)oxy)phenyl)hex-4-ynoic acid;
(S)-3-(4-((3-((2-cyano-6,7-dihydrothieno[3,2-c]pyridin-5(4H)-yl)methyl)benzyl)oxy)phenyl)hex-4-ynoic acid;
(S)-3-(4-((3-((2-formyl-6,7-dihydrothieno[3,2-c]pyridin-5(4H)-yl)methyl)benzyl)oxy)phenyl)hex-4-ynoic acid;
(S)-3-(4-((3-((2-methyl-6,7-dihydropyrazolo[1,5-a]pyrazin-5(4H)-yl)methyl)benzyl)oxy)phenyl)hex-4-ynoic acid;
(S)-3-(4-((3-((2-(methylcarbamoyl)-6,7-dihydrothieno[3,2-c]pyridin-5(4H)-yl)methyl)benzyl)oxy)phenyl)hex-4-ynoic acid;
(S)-3-(4-((3-((2-(dimethylcarbamoyl)-6,7-dihydrothieno[3,2-c]pyridin-5(4H)-yl)methyl)benzyl)oxy)phenyl)hex-4-ynoic acid;
(3S)-3-(4-((3-((2-Methyl-5-(4-(methylsulfonyl)phenyl)pyrrolidin-1-yl)methyl)benzyl)oxy)phenyl)hex-4-ynoic acid;
(S)-3-(4-((3-((2-(Methylsulfonyl)-7,8-dihydropyrido[4,3-d]pyrimidin-6(5H)-yl)methyl)benzyl)oxy)phenyl)hex-4-ynoic acid;
(S)-3-(4-((3-((2-Methoxy-7,8-dihydropyrido[4,3-d]pyrimidin-6(5H)-yl)methyl)benzyl)oxy)phenyl)hex-4-ynoic acid;
(3S)-3-(4-((3-((2-phenylpyrrolidin-1-yl)methyl)benzyl)oxy)phenyl)hex-4-ynoic acid;
(S)-3-(4-((3-(Pyrrolidin-1-ylmethyl)benzyl)oxy)phenyl)hex-4-ynoic acid compound with formic acid;
(S)-3-(4-((3-(Piperidin-1-ylmethyl)benzyl)oxy)phenyl)hex-4-ynoic acid compound with formic acid;
(S)-3-(4-((3-((1-isopropylpyrrolo[3,4-c]pyrazol-5(1H,4H,6H)-yl)methyl)benzyl)oxy)phenyl)hex-4-ynoic acid compound with formic acid;

(R)-3-(4-((3-((2-methyl-6,7-dihydrothieno[3,2-c]pyridin-5(4H)-yl)methyl)benzyl)oxy)phenyl)hex-4-ynoic acid;
(R)-3-(4-((3-((2-Methyl-6,7-dihydrothiazolo[5,4-c]pyridin-5(4'-1)-yl)methyl)benzyl)oxy)phenyl)hex-4-ynoic acid;
(S)-3-(4-((3-((6,7-Dihydro-[1,2,3]triazolo[1,5-a]pyrazin-5(4H)-yl)methyl)benzyl)oxy)phenyl)hex-4-ynoic acid;
3-(4-((3-((2-Methyl-6,7-dihydrothieno[3,2-c]pyridin-5(4H)-yl)methyl)benzyl)oxy)phenyl)hex-4-ynoic acid;
3-(4-((3-((2-Methyl-6,7-dihydrothiazolo[5,4-c]pyridin-5(4H)-yl)methyl)benzyl)oxy)phenyl)hex-4-ynoic acid;
Calcium (S)-3-(4-((3-((2-chloro-6,7-dihydrothiazolo[5,4-c]pyridin-5(4H)-yl)methyl)benzyl)oxy)phenyl)hex-4-ynoate;
(S)-3-(4-((3-((2-(cyclopropylcarbamoyl)-6,7-dihydrothieno[3,2-c]pyridin-5(4H)-yl)methyl)benzyl)oxy)phenyl)hex-4-ynoic acid;
(S)-3-(4-((3-((2-(pyrrolidine-1-carbonyl)-6,7-dihydrothieno[3,2-c]pyridin-5(4H)-yl)methyl)benzyl)oxy)phenyl)hex-4-ynoic acid;
(S)-3-(4-((3-((2-Aacetamido-6,7-dihydrothieno[3,2-c]pyridin-5(4H)-yl)methyl)benzyl)oxy)phenyl)hex-4-ynoic acid;
Calcium (S)-3-(4-((3-((2-cyclopropyl-6,7-dihydrooxazolo[4,5-c]pyridin-5(4H)-yl)methyl)benzyl)oxy)phenyl)hex-4-ynoate;
(S)-3-(4-((3-((2-Nitro-6,7-dihydrothieno[3,2-c]pyridin-5(4H)-yl)methyl)benzyl)oxy)phenyl)hex-4-ynoic acid;
(S)-3-(4-((3-((2-(Dimethylamino)-7,8-dihydropyrido[4,3-d]pyrimidin-6(5H)-yl)methyl)benzyl)oxy)phenyl)hex-4-ynoic acid compound with 2,2,2-trifluoroacetic acid;
(S)-3-(4-((3-((2-Amino-7,8-dihydropyrido[4,3-d]pyrimidin-6(5H)-yl)methyl)benzyl)oxy)phenyl)hex-4-ynoic acid compound with 2,2,2-trifluoroacetic acid;
(S)-3-(4-((3-((7,8-Dihydro-1,6-naphthyridin-6(5H)-yl)methyl)benzyl)oxy)phenyl)hex-4-ynoic acid;
(S)-3-(4-((3-((2-Cyclopropyl-6,7-dihydrothieno[3,2-c]pyridin-5(4H)-yl)methyl)benzyl)oxy)phenyl)hex-4-ynoic acid compound with 2,2,2-trifluoroacetic acid;
(S)-3-(4-((3-((2-Acetamido-6,7-dihydrothiazolo[5,4-c]pyridin-5(4H)-yl)methyl)benzyl)oxy)phenyl)hex-4-ynoic acid compound with 2,2,2-trifluoroacetic acid;
(S)-3-(4-((3-((2-Ethyl-6,7-dihydrothieno[3,2-c]pyridin-5(4H)-yl)methyl)benzyl)oxy)phenyl)hex-4-ynoic acid;
(S)-3-(4-((3-((2-Acetyl-6,7-dihydrothieno[3,2-c]pyridin-5(4H)-yl)methyl)benzyl)oxy)phenyl)hex-4-ynoic acid; and
(S)-3-(4-((3-((2-((Methylamino)methyl)-6,7-dihydrothieno[3,2-c]pyridin-5(4H)-yl)methyl)benzyl)oxy)phenyl)hex-4-ynoic acid compound with 2,2,2-trifluoroacetic-acid.

The following compounds can be synthesized following the similar procedure as described for example 1 with suitable modifications as are well known to a person skilled in the art and are considered to be encompassed within the scope of the present invention.

3-(4-((3-((4H-furo[3,4-c]pyrrol-5(6H)-yl)methyl)benzyl)oxy)phenyl)-3-cyanopropanoic acid

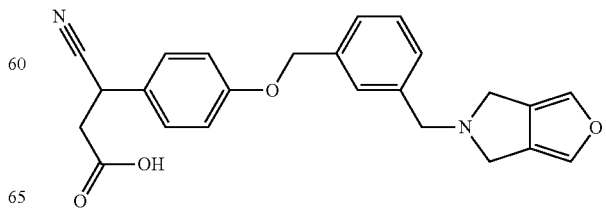

25

3-cyano-3-(4-((3-((4-oxo-6,7-dihydrothieno[3,2-c]
pyridin-5(4H)yl)methyl)benzyl)oxy)phenyl)pro-
panoic acid

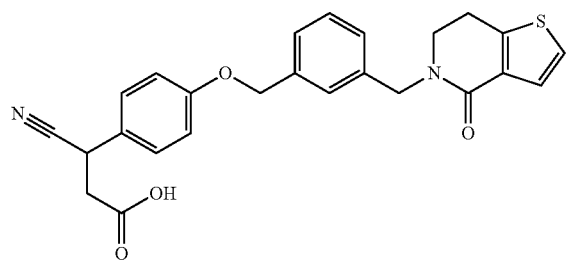 [SMILES: N#CC(CC(=O)O)c1ccc(OCc2cccc(CN3CCc4sccc4C3=O)c2)cc1]

3-cyano-3-(4-((3-((2,2-dioxido-1H-thieno[3,4-c]
pyrrol-5(3H,4H,6H)-yl)methyl)benzyl)oxy)phenyl)
propanoic acid

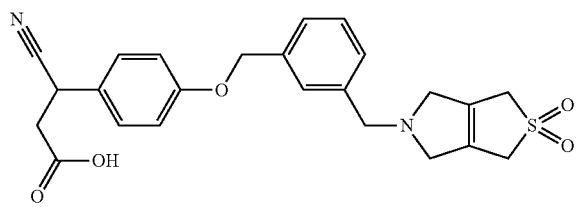 [SMILES: N#CC(CC(=O)O)c1ccc(OCc2cccc(CN3CC4=C(C3)CS(=O)(=O)C4)c2)cc1]

3-cyano-3-(4-((3-((6,7-dihydrothieno[3,2-c]pyridin-5
(4H)-yl)methyl)benzyl)oxy)phenyl)propanoic acid

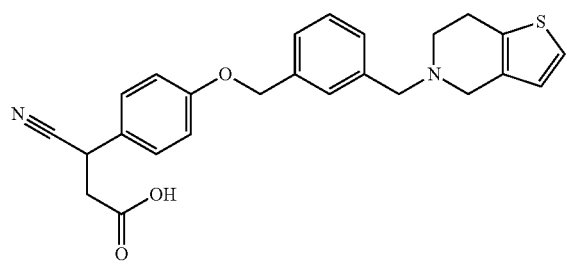 [SMILES: N#CC(CC(=O)O)c1ccc(OCc2cccc(CN3CCc4sccc4C3)c2)cc1]

(S)-3-(4-((3-((2-methoxy-6,7-dihydrothieno[3,2-c]
pyridin-5(4H)-yl)methyl)benzyl)oxy)phenyl)hex-4-
ynoic acid

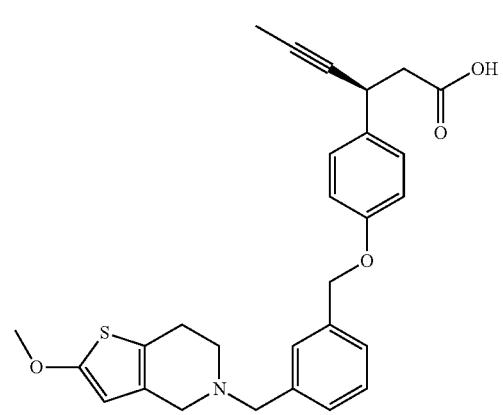 [SMILES: CC#C[C@@H](CC(=O)O)c1ccc(OCc2cccc(CN3CCc4sc(OC)cc4C3)c2)cc1]

26

(S)-3-(4-((3-((2-acetoxy-6,7-dihydrothieno[3,2-c]
pyridin-5(4H)-yl)methyl)benzyl)oxy)phenyl)hex-4-
ynoic acid

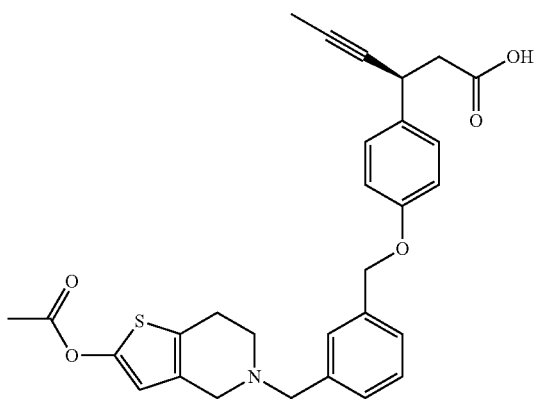 [SMILES: CC#C[C@@H](CC(=O)O)c1ccc(OCc2cccc(CN3CCc4sc(OC(C)=O)cc4C3)c2)cc1]

(S)-3-(4-((3-((2-(methylsulfonyl)-5H-pyrrolo[3,4-d]
pyrimidin-6(7H)-yl)methyl)benzyl)oxy)phenyl)hex-
4-ynoic acid

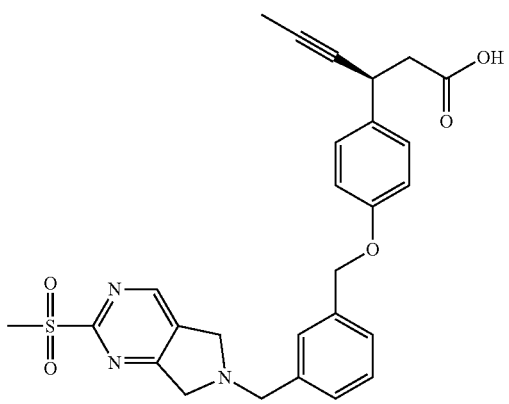 [SMILES: CC#C[C@@H](CC(=O)O)c1ccc(OCc2cccc(CN3Cc4cnc(S(C)(=O)=O)nc4C3)c2)cc1]

(S)-3-(4-((3-((6,7-dihydrofuro[3,2-c]pyridin-5(4H)-
yl)methyl)benzyl)oxy)phenyl)hex-4-ynoic acid

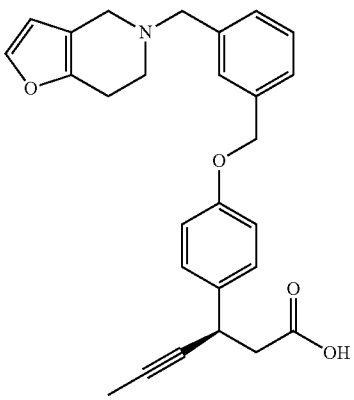 [SMILES: CC#C[C@H](CC(=O)O)c1ccc(OCc2cccc(CN3CCc4occc4C3)c2)cc1]

27

(S)-3-(4-((3-((2-(2,2,2-trifluoroethyl)-6,7-dihydrothieno[3,2-c]pyridin-5(4H)-yl)methyl)benzyl)oxy)phenyl)hex-4-ynoic acid

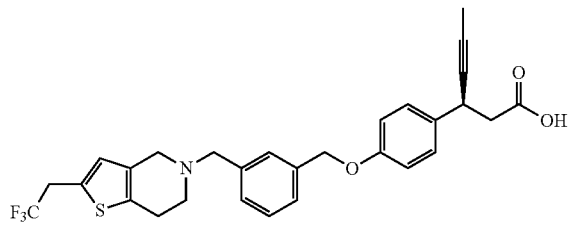 [SMILES: CC#C[C@@H](CC(=O)O)c1ccc(OCc2cccc(CN3CCc4sc(CC(F)(F)F)cc4C3)c2)cc1]

(S)-3-(4-((3-((2-isopropyl-6,7-dihydrothieno[32-c]pyridin-5(4H)-yl)methyl)benzyl)oxy)phenyl)hex-4-ynoic acid

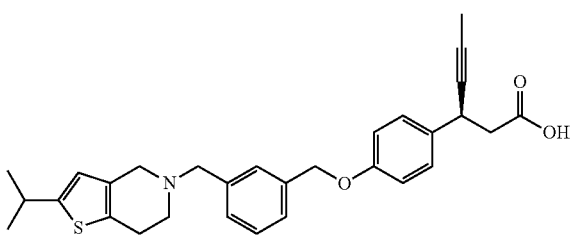 [SMILES: CC#C[C@@H](CC(=O)O)c1ccc(OCc2cccc(CN3CCc4sc(C(C)C)cc4C3)c2)cc1]

(S)-3-(4-((3-((2-(dimethylamino)-6,7-dihydrothieno[3,2-c]pyridin-5(4H)-yl)methyl)benzyl)oxy)phenyl)hex-4-ynoic acid

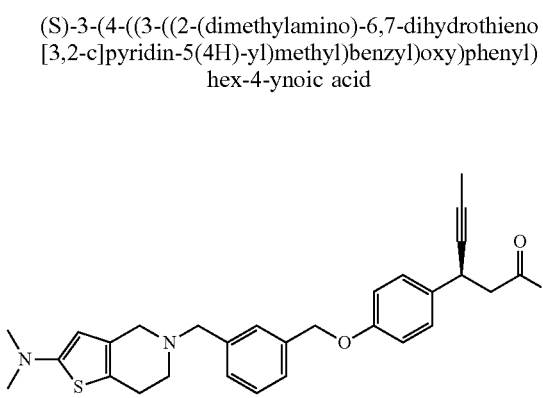

(S)-3-(4-((3-((2-(tert-butyl)-6,7-dihydrothieno[3,2-c]pyridin-5(4H)-yl)methyl)benzyl)oxy)phenyl)hex-4-ynoic acid

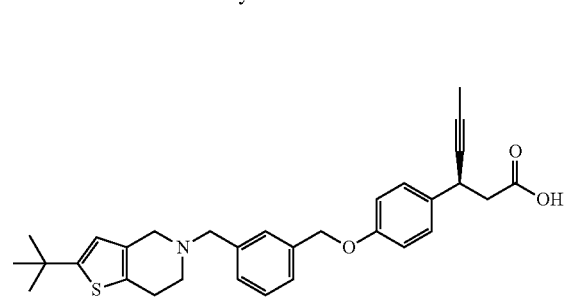

28

(S)-3-(4-((3-((2-oxo-1,2,6,7-tetrahydrothiazolo[5,4-c]pyridin-5(4H)-yl)methyl)benzyl)oxy)phenyl)hex-4-ynoic acid

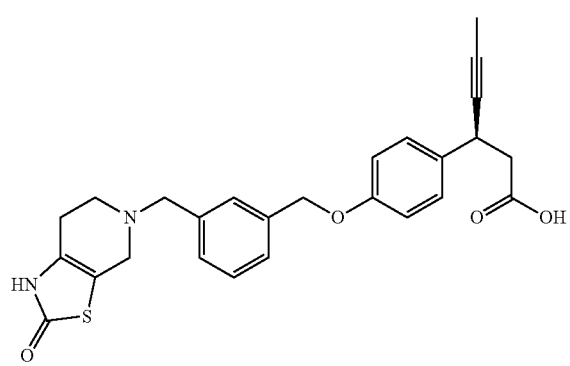 [SMILES: CC#C[C@@H](CC(=O)O)c1ccc(OCc2cccc(CN3CCc4[nH]c(=O)sc4C3)c2)cc1]

(S)-3-(4-((3-((2-cyano-6,7-dihydrothiazolo[5,4-c]pyridin-5(4H)-yl)methyl)benzyl)oxy)phenyl)hex-4-ynoic acid

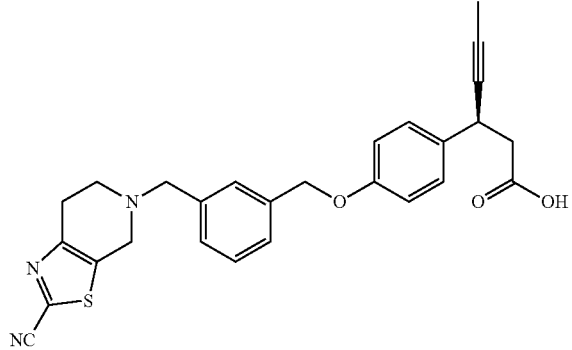 [SMILES: CC#C[C@@H](CC(=O)O)c1ccc(OCc2cccc(CN3CCc4nc(C#N)sc4C3)c2)cc1]

(3S)-3-(4-((3-((4-phenyl-6,7-dihydrothieno[3,2-c]pyridin-5(4H)-yl)methyl)benzyl)oxy)phenyl)hex-4-ynoic acid

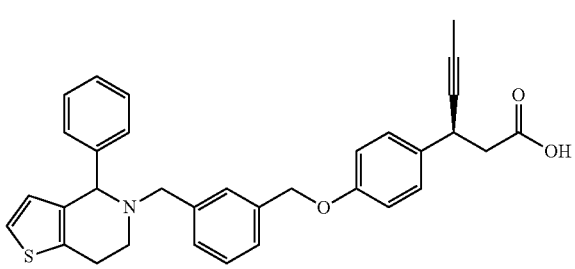 [SMILES: CC#C[C@@H](CC(=O)O)c1ccc(OCc2cccc(CN3CCc4sccc4C3c3ccccc3)c2)cc1]

(3S)-3-(4-((3-((4-methyl-6,7-dihydrothieno[3,2-c]pyridin-5(4H)-yl)methyl)benzyl)oxy)phenyl)hex-4-ynoic acid

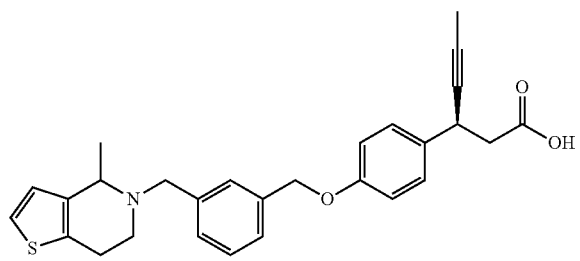 [SMILES: CC#C[C@@H](CC(=O)O)c1ccc(OCc2cccc(CN3CCc4sccc4C3C)c2)cc1]

The novel compounds of this invention may be prepared using the reactions and techniques described in the below section along with, whenever appropriate other suitable processes known to a skilled person. The reactions are performed in solvents appropriate to the reagents and materials employed and are suitable for the transformations being effected. It is understood by those skilled in the art that the nature and order of the synthetic steps presented may be varied for the purpose of optimizing the formation of the compounds of the present invention and also that certain steps may be modified, altered, obvious steps added or deleted in order to optimize as well as required for preparing the compounds of the present invention. Such, obvious changes should also be considered as being part of the present invention.

Scheme 1: Compounds of general formula (I) may be prepared according to the scheme described below

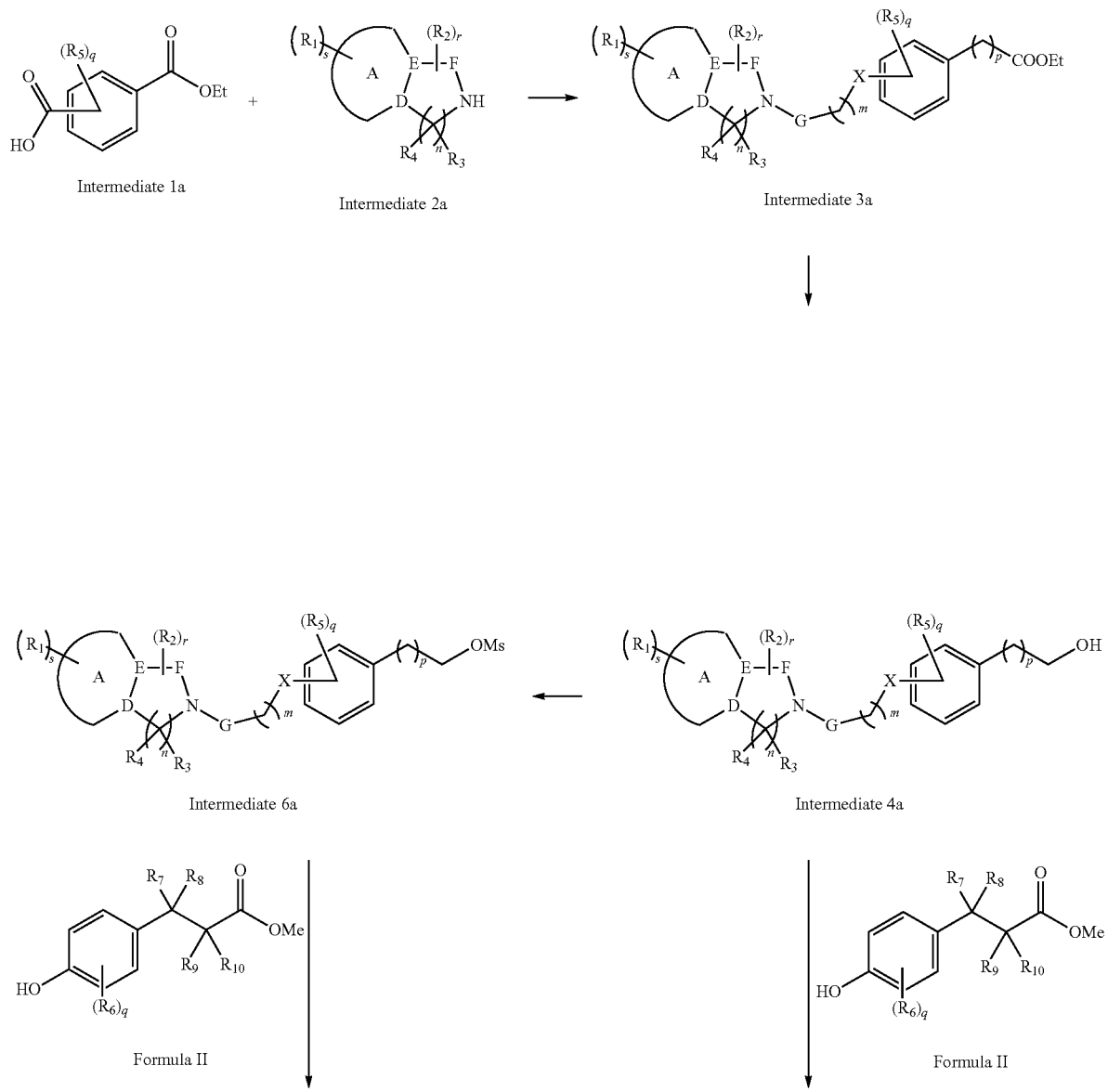

-continued

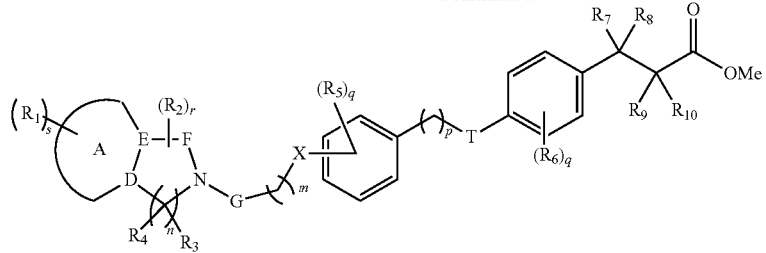

Intermediate 5a

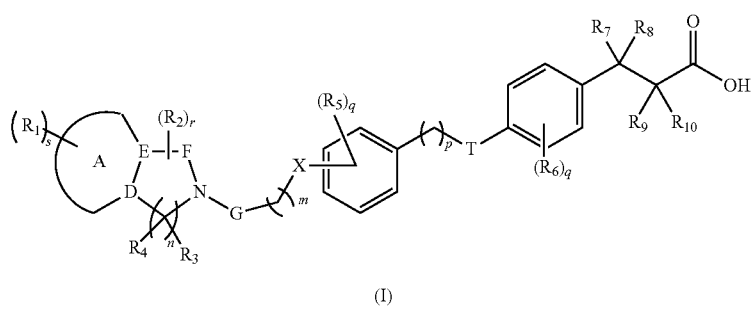

(I)

A compound of formula (I) can be prepared in accordance with reactions as depicted in scheme 1.

The first step involves the reaction of substituted carboxylic acid (intermediate 1a) with an appropriate substituted heterocycle (intermediate 2a) under peptide bond formation conditions to give intermediate 3a. The ester of intermediate 3a can be reduced using a suitable reducing agent such as diisobutylaluminum hydride, lithium aluminum hydride or sodium borohydride etc. to give intermediate 4a. Intermediate 4a can be further reacted with compounds of formula II under Mitsunobu conditions to give intermediate 5a. Mitsunobu conditions involve reacting an alcohol intermediate 4a with a nucleophile such as a phenol (formula II), using a suitable phosphine such as tributyl phosphine, triphenyl phosphine, or triethyl phosphine and ah azodicarbonyl such as ADDP or an azodicarboxylate (DEAD).

Alternatively, intermediate 4a can be converted to compound having suitable leaving group such as mesylate derivative (intermediate 6a) using an appropriate set of reactants and conditions such as methanesulfonyl chloride and triethylamine.

The intermediate 6a can be reacted with compound of formula II using diisopropyl ethylamine or cesium carbonate to give intermediate 5a.

The intermediate 5a can be hydrolyzed to give carboxylic acid derivative of formula (I) using bases such as lithium hydroxide, sodium hydroxide or potassium hydroxide.

In an optional step, a pharmaceutically acceptable salt of a compound of formula (I) can be formed by reaction of appropriate compound of formula (I) with a pharmaceutically acceptable base or with and acid in a suitable solvent under standard conditions. Optionally, the formation of such salts can occur simultaneously upon hydrolysis of an ester intermediate.

The formation of such salts is well known and appreciated in the art.

The compounds of the present invention can be used either alone or in combination with one or more therapeutic agents selected from insulin, insulin derivatives and mimetics, insulin secretagogues, insulin sensitizers, biguanide agents, alpha-glucosidase inhibitors, insulinotropic sulfonylurea receptor ligands, meglitinides, GLP-1, GLP-1 analogs, DPP-IV inhibitors, GPR-119 activators, sodium-dependent glucose co-transporter (SGLT2) inhibitors, PPAR modulators, non-glitazone type PPAR delta agonist, HMG-CoA reductase inhibitors, cholesterol-lowering drugs, rennin inhibitors, anti-thrombotic and anti-platelet agents and other anti-obesity agents or pharmaceutically acceptable salts thereof. Such use will depend on the condition of the patient being treated and is well within the scope of a skilled practitioner.

Following the general process described above, including suitable modifications and additions which are within the scope of a skilled person, the following compounds of formula (1) were prepared as follows:

1H NMR spectral data given in the examples (vide infra) are recorded using a 400 MHz spectrometer (Bruker AVANCE-400) and reported in δ scale. Until and otherwise mentioned the solvent used for NMR is $CDCl_3$.

Example 1
(S)-3-(4-((3-((6,7-dihydrothieno[3,2-c]pyridin-5(4H)yl)methyl)benzyl)oxy)phenyl)hex-4-ynoic acid (1)
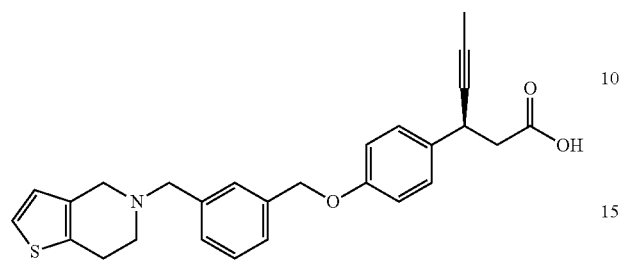
Scheme 2:
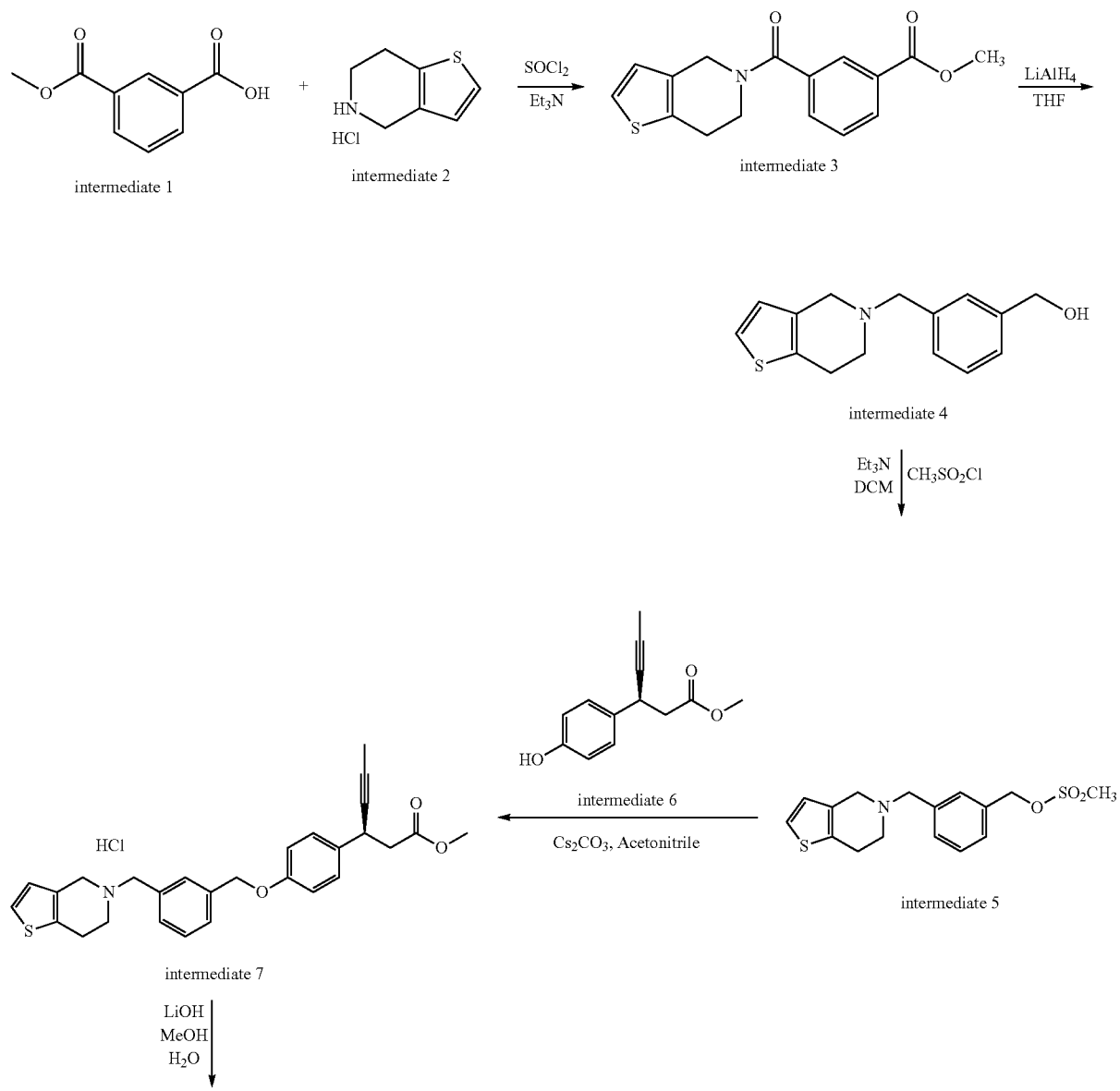

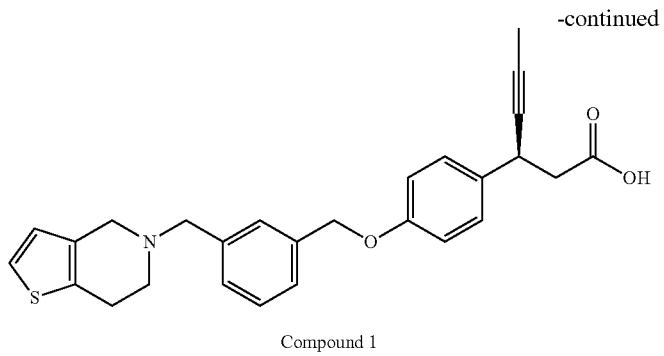

Compound 1

Procedure i. Methyl 3-(4,5,6,7-tetrahydrothieno[3,2-c]pyridine-5-carbonyl)benzoate (Intermediate 3)

To 3-(methoxycarbonyl)benzoic acid intermediate 1 (10 g, 55.5 mmol) was added thionyl chloride (16.21 mL, 222 mmol) in small portions at 25° C. followed by a drop of dimethylformamide. The reaction mixture was stirred under refluxing for 3 h. Excess thionyl chloride was evaporated under reduced pressure at 100° C. The 4,5,6,7-tetrahydrothieno[3,2-c]pyridine hydrochloride intermediate 2 (12.19 g, 69.4 mmol) was dissolved in 100 mL of water, to that added solution of sodium hydroxide (4.44 g, 111 mmol) in 25 mL of water. Free base of 4,5,6,7-tetrahydrothieno[3,2-c]pyridine was extracted in dichloromethane (75 mL), dried over anhydrous potassium carbonate. The acid chloride was dissolved in anhydrous dichloromethane (75 mL) and cooled to 0° C.

To the reaction mixture added drop wise triethylamine (15.47 mL, 111 mmol) followed by solution of 4,5,6,7-tetrahydrothieno[3,2-c]pyridine in dichloromethane (75 mL) drop by drop at 0° C. The reaction mixture was warmed to 25° C. and stirred it for 3 h. Progress of the reaction was monitored by TLC. The reaction mixture was poured into ice-water (125 mL), adjusted pH ~4 with 10% HCl and extracted with dichloromethane (3×100 mL). The combined organic fractions were washed with 5% sodium hydroxide (100 mL) followed by brine (100 mL), dried over anhydrous Na2SO4 and evaporated on a rotatory evaporator under reduced pressure to afford crude amide intermediate 3.

The crude product was purified by flash column chromatography using 230-400 mesh silica-gel as a stationary phase and 10-50% ethyl acetate-hexanes as a mobile phase afforded pure methyl 3-(4,5,6,7-tetrahydrothieno[3,2-c]pyridine-5-carbonyl)benzoate (12 g, 39.8 mmol, 71.7% yield)

ii. (3-((6,7-Dihydrothieno[3,2-c]pyridin-5(4H)-yl)methyl)phenyl)methanol (Intermediate 4)

To a solution of methyl 3-(4,5,6,7-tetrahydrothieno[3,2-c]pyridine-5-carbonyl)benzoate intermediate 3 (12 g, 39.8 mmol) in dry THF (100 mL) was added LiAlH₄ (3.02 g, 80 mmol) in small portions at 25° C. The reaction mixture was stirred under refluxing for 3 h. The progress of reaction was monitored by TLC by using mobile phase 30% ethyl acetate in hexane. Suspension of aqueous sodium sulfate was added drop wise to the reaction mixture to quench excess LiAlH₄. Ethyl acetate (150 mL) was added to the reaction mixture and refluxed for 30 min and decanted ethyl acetate, this process was repeated three times to ensure no product in white slug of lithium sulfate and aluminum hydroxide. The combined organic fractions were dried over anhydrous Na₂SO₄ and evaporated on a rotatory evaporator under reduced pressure to afford crude product as pale yellow sticky mass of intermediate 4.

The crude alcohol intermediate 4 was purified by flash column chromatography using 230-400 mesh silica-gel as stationary phase and 10-50% ethyl acetate-hexane as a mobile phase afforded pure (3-((6,7-dihydrothieno[3,2-c]pyridin-5(4H)-yl)methyl)phenyl)methanol intermediate 4 (5.41 g, 20.86 mmol, 52.4% yield).

iii. (S)-3-(4-((3-((6,7-dihydrothieno[3,2-c]pyridin-5(4H)-yl)methyl)benzyl)oxy)phenyl)hex-4-ynoic acid (1)

To a solution of (3-((6,7-dihydrothieno[3,2-c]pyridin-5(4H)-yl)methyl)phenyl)methanol intermediate 4 (0.16 g, 0.617 mmol) in 5 mL of anhydrous tetrahydrofuran was added triethylamine (0.258 ml, 1.851 mmol) followed by methanesulfonyl chloride (141 mg, 1.234 mmol) at 0° C. The reaction mixture was stirred at 25° C. for 1 h. The progress of the reaction was monitored by TLC. The reaction mixture was poured into ice-water (25 mL) and extracted with dichloromethane (3×25 mL). The combined organic fractions were dried over anhydrous Na₂SO₄ and evaporated on a rotatory evaporator under reduced pressure to afford 3-((6,7-dihydrothieno[3,2-c]pyridin-5(4H)-yl)methyl)benzyl mesylate intermediate (5) as pale yellow sticky mass.

To a solution of (S)-methyl-3-(4-hydroxyphenyl)hex-4-ynoate intermediate 6 (162 mg, 0.740 mmol) in Acetonitrile (5.00 ml) was added cesium carbonate (603 mg, 1.851 mmol) followed by solution of 3-((6,7-dihydrothieno[3,2-c]pyridin-5(4H)-yl)methyl)benzyl mesylate 5 in 2 mL of acetonitrile at 25° C. Reaction mixture was stirred for 3 h at 75° C. Progress of the reaction was monitored by TLC. After completion of the reaction, volatiles were evaporated off under reduced pressure. The reaction mixture was poured into ice-water (25 mL) and product was extracted with dichloromethane (3×25 mL). The combined organic fractions were dried over anhydrous Na₂SO₄ and evaporated on a rotatory evaporator under reduced pressure to afford crude product as pale yellow sticky mass. Ethereal hydrochloride solution was added to the crude product, ether was evaporated off and residue was triturated with ethyl acetate afforded 65 mg of (S)-methyl 3-(4-((3-((6,7-dihydrothieno[3,2-c]pyridin-5(4H)-yl)methyl)benzyl)oxy)phenyl)hex-4-ynoate hydrochloride intermediate (7). Ester hydrochloride salt intermediate 7 (60 mg, 0.121 mmol) was hydrolyzed using mixture of THF (2 mL) and MeOH (1 mL) was added NaOH (24.19 mg, 0.605 mmol) in water (1 mL) at 25° C.

Reaction mixture was stirred for 12 h at 25° C. Progress of the reaction was monitored by TLC. After completion of the reaction, volatiles were evaporated off, the residue was treated with ice-water (5 mL), adjusted pH ~4 (1N HCl), extracted with dichloromethane (3×25 mL) and dried over anhydrous Na$_2$SO$_4$. Evaporation of solvents on a rotatory evaporator under reduced pressure to afford crude product. Crude acid was purified by preparative TLC to afford (S)-3-(4-((3-((6,7-dihydrothieno[3,2-c]pyridin-5(4H)-yl)methyl)benzyl)oxy)phenyl)hex-4-ynoic acid 1 (42 mg, 0.094 mmol, 78% yield)

$^1$H NMR (DMSO-d$_6$, 400 MHz) δ: 7.42 (s, 1H), 7.37-7.24 (m, 6H), 6.94 (d, J=8.4 Hz, 2H), 6.75 (d, J=5.2 Hz, 1H), 5.07 (s, 2H), 3.94 (m, 1H), 3.68 (s, 2H), 3.43 (s, 2H), 2.78-2.72 (m, 4H), 2.57-2.55 (m, 2H), 1.77 (d, J=1.6 Hz, 3H); ESIMS: 446.2 (M+H)$^+$.

The following compounds can be prepared by following the general scheme 1 and the process described in Example 1 above, including their suitable modifications well within the scope of a skilled person.

Example 2

Lithium 3-(4-((3-((4H-furo[3,4-c]pyrrol-5(6H)-yl)methyl)benzyl)oxy)phenyl)-3-cyanopropanoic acid

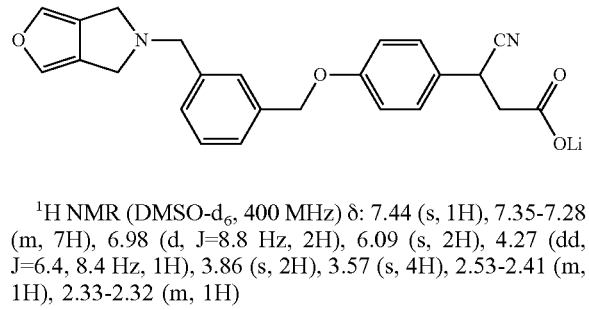

$^1$H NMR (DMSO-d$_6$, 400 MHz) δ: 7.44 (s, 1H), 7.35-7.28 (m, 7H), 6.98 (d, J=8.8 Hz, 2H), 6.09 (s, 2H), 4.27 (dd, J=6.4, 8.4 Hz, 1H), 3.86 (s, 2H), 3.57 (s, 4H), 2.53-2.41 (m, 1H), 2.33-2.32 (m, 1H)

Example 3

3-cyano-3-(4-((3-((4-oxo-6,7-dihydrothieno[3,2-c]pyridin-5(4H)yl)methyl)benzyl)oxy)phenyl)propanoic acid

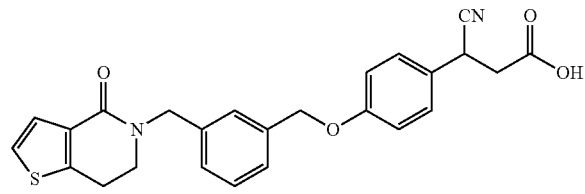 [SMILES: N#CC(CC(=O)O)c1ccc(OCc2cccc(CN3CCc4sccc4C3=O)c2)cc1]

$^1$H NMR: (CDCl$_3$, 400 MHz):—7.47 (d, J=5.2 Hz, 1H), 7.37-7.23 (m, 6H), 7.11 (d, J=5.2 Hz, 1H), 6.92 (d, J=8.8 Hz, 2H), 5.06 (s, 2H), 4.77-4.68 (m, 2H), 4.19 (t, J=7.6 Hz, 1H), 3.55 (t, J=6.8 Hz, 2H), 3.06-2.98 (m, 3H), 2.88-2.82 (m, 1H)

Example 4

Lithium 3-cyano-3-(4-((3-((3-(trifluoromethyl)-5,6-dihydro-[1,2,4]triazolo[4,3-a]pyrazin-7(8H)-yl)methyl)benzyl)oxy)phenyl)propanoic acid

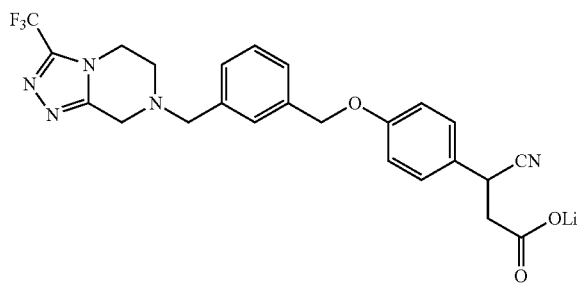

$^1$H NMR (CD$_3$OD, 400 MHz) δ: 7.48 (s, 1H), 7.39-7.36 (m, 3H), 7.31 (dd, =2, 6.8 Hz, 2H), 6.98 (dd, J=2.4, 6.8 Hz, 2H), 5.10 (s, 2H), 4.3-4.26 (m, 1H), 4.18 (t, J=5.2 Hz, 2H), 3.89 (s, 2H), 3.83 (s, 2H), 2.97 (t, J=5.6 Hz, 2H), 2.74 (dd, J=8.8, 15.6 Hz, 1H), 2.58 (dd, J=8.8, 15.6 Hz, 1H).

Example 5

3-cyano-3-(4-((3-((2,2-dioxido-1H-thieno[3,4-c]pyrrol-5(3H,4H,6H)-yl)methyl)benzyl)oxy)phenyl)propanoic acid

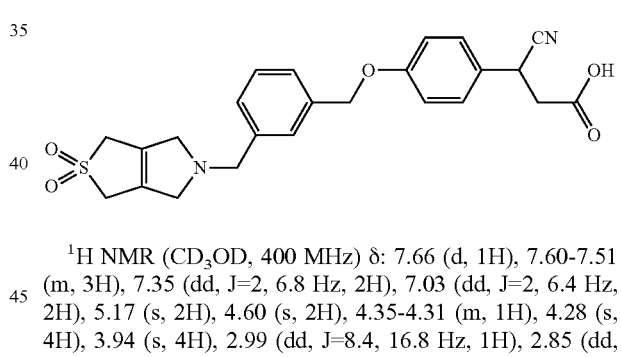

$^1$H NMR (CD$_3$OD, 400 MHz) δ: 7.66 (d, 1H), 7.60-7.51 (m, 3H), 7.35 (dd, J=2, 6.8 Hz, 2H), 7.03 (dd, J=2, 6.4 Hz, 2H), 5.17 (s, 2H), 4.60 (s, 2H), 4.35-4.31 (m, 1H), 4.28 (s, 4H), 3.94 (s, 4H), 2.99 (dd, J=8.4, 16.8 Hz, 1H), 2.85 (dd, J=6.4, 16.4 Hz, 1H).

Example 6

3-cyano-3-(4-((3-((6,7-dihydrothieno[3,2-c]pyridin-5(4H)-yl)methyl)benzyl)oxy)phenyl)propanoic acid

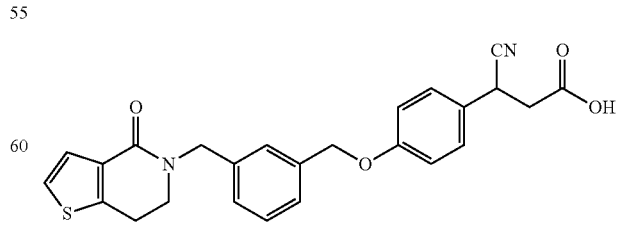

$^1$H NMR (CDCl$_3$, 400 MHz) δ: 7.58 (s, 1H), 7.37-7.32 (m, 2H), 7.22-7.16 (m, 4H), 6.88 (dd, J=2, 6.8 Hz, 2H), 6.71 (d, J=5.2 Hz, 1H), 5.00 (s, 2H), 4.18-4.14 (m, 1H), 3.99 (s,

2H), 3.88 (s, 2H), 3.19-3.16 (m, 2H), 3.03-3.00 (m, 2H), 2.87-2.81 (m, 1H), 2.70-2.64 (m, 1H).

Example 7

(S)-3-(4-((3-((2-methyl-6,7-dihydrothieno[3,2-c]pyridin-5(4H)-yl)methyl)benzyl)oxy)phenyl)hex-4-ynoic acid

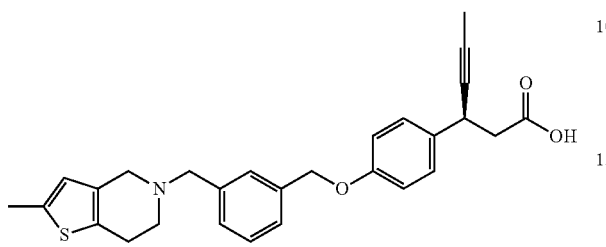

$^1$H NMR (CDCl$_3$, 400 MHz) δ: 7.38-7.25 (m, 6H), 6.88 (d, J=5.2 Hz, 2H), 6.33 (s, 1H), 5.04-4.98 (m, 2H), 4.05-4.00 (m, 1H), 3.80-3.71 (m, 2H), 3.64-3.55 (m, 2H), 2.92-2.61 (m, 6H), 2.39 (s, 3H), 1.82 (d, J=2.4 Hz, 3H).

Example 8

(S)-3-(4-((3-((1-(tert-butoxycarbonyl)-6,7-dihydro-1H-pyrrolo[3,2-c]pyridin-5(4H)-yl)methyl)benzyl)oxy)phenyl)hex-4-ynoic acid

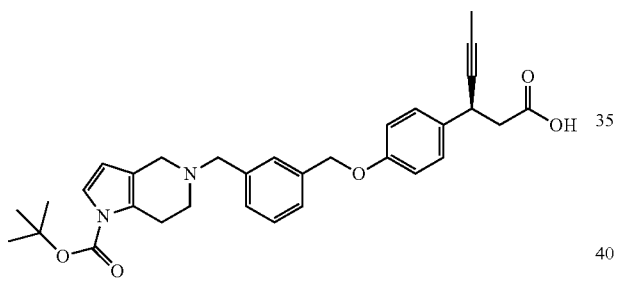

$^1$H NMR (CDCl$_3$, 400 MHz) δ: 7.47-7.38 (m, 4H), 7.27 (d, J=8.8 Hz, 2H), 7.18 (d, J=3.2 Hz, 1H), 6.86 (d, J=8.8 Hz, 2H), 5.94 (d, J=3.2 Hz, 2H), 5.05 (s, 2H), 4.08 (s, 2H), 4.05-4.01 (m, 1H), 3.85 (s$_{(br)}$, 2H), 3.30-3.15 (m, 4H), 2.78 (dd, J=8.8, 15.2 Hz, 1H), 2.65 (dd, J=8, 15.2 Hz, 1H), 1.80 (d, J=2.4 Hz, 3H), 1.59 (s, 9H).

Example 9

(S)-3-(4-((3-((6,7-dihydro-1H-pyrrolo[3,2-c]pyridin-5(4H)-yl)methyl)benzyl)oxy)phenyl)hex-4-ynoic acid

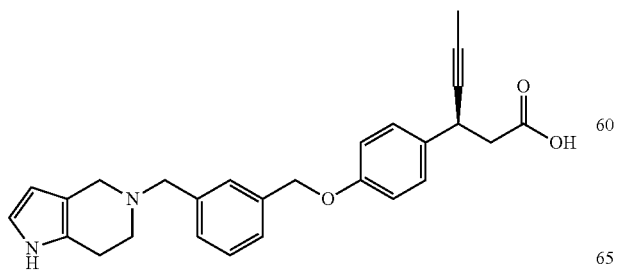

$^1$H NMR (CDCl$_3$, 400 MHz) δ: 8.51 (s, 1H), 7.42-7.33 (m, 4H), 7.25 (d, J=8.9 Hz, 2H), 6.81 (d, J=9 Hz, 2H), 6.63 (t, J=2.4 Hz, 1H), 5.89 (t, J=2.4 Hz, 1H), 5.06 (s, 2H), 4.07-3.99 (m, 3H), 3.87 (s, 2H), 3.08 (s$_{(br)}$, 2H), 2.80-2.74 (m, 3H), 2.61 (m, 1H), 1.80 (d, J=2.4 Hz, 3H)

Example 10

(S)-3-(4-((3-((2-methyl-6,7-dihydrothiazolo[5,4-c]pyridin-5(4H)-yl)methyl)benzyl)oxy)phenyl)hex-4-ynoic acid

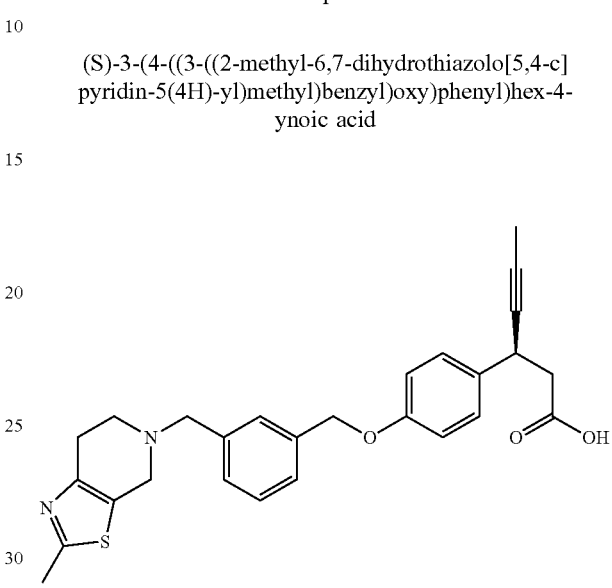

$^1$H NMR (CDCl$_3$, 400 MHz) δ: 7.41-7.38 (m, 4H), 7.27 (d, J=8.4 Hz, 2H), 6.85 (d, J=8.4 Hz, 2H), 5.19-5.08 (m, 2H), 4.04-3.91 (m, 1H), 3.75 (s$_{(br)}$, 4H), 2.87-2.69 (m, 4H), 2.66 (s, 3H), 2.58-2.41 (m, 2H), 1.80 (d, J=2.4 Hz, 3H)

Example 11

(S)-3-(4-((3-((3-(trifluoromethyl)-5,6-dihydro-[1,2,4]triazolo[4,3-a]pyrazin-7(8H)-yl)methyl)benzyl)oxy)phenyl)hex-4-ynoic acid

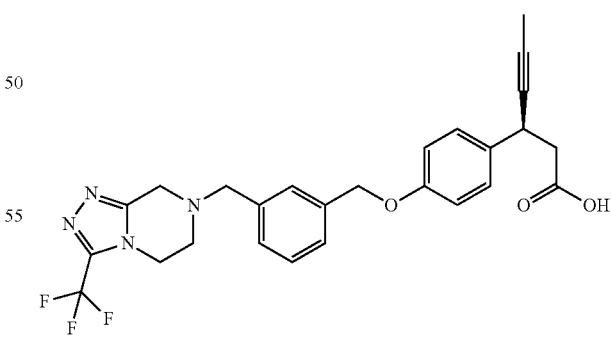

$^1$H NMR (CDCl$_3$, 400 MHz) δ: 7.40-7.26 (m, 6H), 6.86 (d, J=8.8 Hz, 2H), 5.12 (dd, J=12.8, 18.4 Hz, 2H), 4.15-4.12 (m, 2H), 4.04-3.99 (m, 1H), 3.86-3.69 (m, 4H), 3.00-2.85 (m, 2H), 2.82 (dd, J=6.8, 15.2 Hz, 1H), 2.65 (dd, J=6.8, 15.2 Hz, 11H), 1.82 (J=2 Hz, 3H).

Example 12

(S)-3-(4-((3-(isoindolin-2-ylmethyl)benzyl)oxy)phenyl)hex-4-ynoic acid trifluoroacetic acid

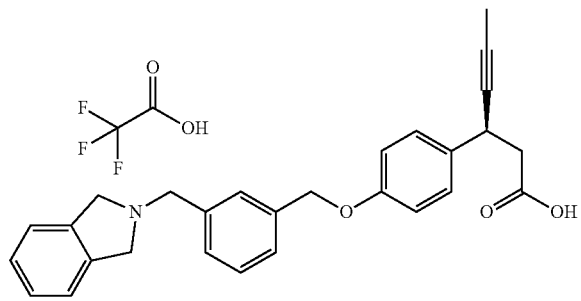

$^1$H NMR (CDCl$_3$, 400 MHz) δ: 7.52-7.44 (m, 2H), 7.42-7.34 (m, 4H), 7.31-7.26 (m, 4H), 6.85 (d, J=8.4 Hz, 2H), 5.09 (s, 2H), 4.70 (s, 2H), 4.34-4.29 (m, 2H), 4.04-4.00 (m, 1H), 3.32 (s, 2H), 2.85-2.78 (m, 1H), 2.70-2.63 (m, 1H), 1.80 (d, J=2.4 Hz, 3H).

Example 13

(S)-3-(4-((3-((3,4-dihydroquinolin-1(2H)-yl)methyl)benzyl)oxy)phenyl)hex-4-ynoic acid

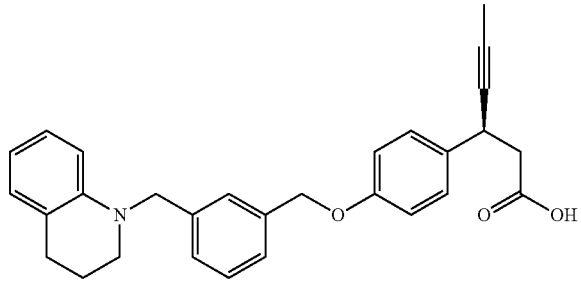 [SMILES: CC#C[C@@H](CC(=O)O)c1ccc(OCc2cccc(CN3CCCc4ccccc43)c2)cc1]

$^1$H NMR (CDCl$_3$, 400 MHz) δ: 7.32-7.22 (m, 6H), 6.99-6.90 (m, 4H), 6.60-6.57 (m, 1H), 6.50 (d, J=8.4 Hz, 2H), 5.02 (s, 2H), 4.49 (s, 2H), 4.06 (s$_{(br)}$, 1H), 3.36 (s$_{(br)}$, 2H), 3.02-2.78 (m, 4H), 2.02-2.00 (m, 2H), 1.80 (s, 3H).

Example 14

(S)-3-(4-((3-((2-bromo-6,7-dihydrothieno[3,2-c]pyridin-5(4H)-yl)methyl)benzyl)oxy)phenyl)hex-4-ynoic acid

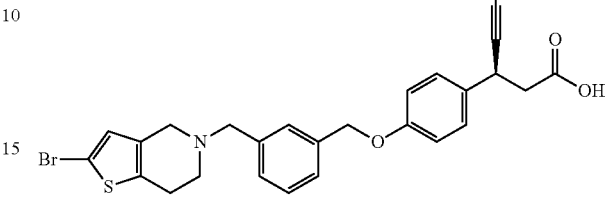

$^1$H NMR (CDCl$_3$, 400 MHz) δ: 7.42-7.36 (m, 3H), 7.32-7.25 (m, 3H), 6.90 (d, J=8.4 Hz, 2H), 6.66 (s, 1H), 5.05 (s, 2H), 4.06-4.02 (m, 1H), 3.94-3.92 (m, 2H), 3.68 (s$_{(br)}$, 2H), 3.01 (s$_{(br)}$, 2H), 2.88-2.85 (m, 2H), 2.80-2.74 (m, 1H), 2.69-2.63 (m, 1H), 1.83 (d, J=2.4 Hz, 3H).

Example 15

(S)-3-(4-((3-((3,4-dihydroisoquinolin-2(1H)-yl)methyl)benzyl)oxy)phenyl)hex-4-ynoic acid

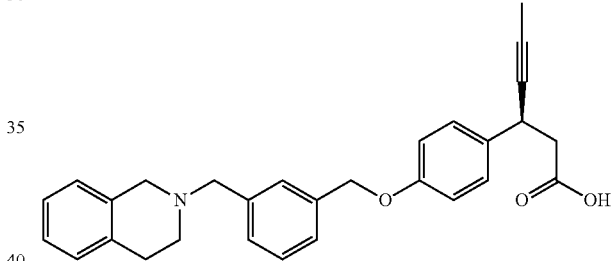

$^1$H NMR (CDCl$_3$, 400 MHz) δ: 7.47 (s, 1H), 7.42-7.27 (m, 5H), 7.22-7.15 (m, 3H), 7.05-7.02 (m, 1H), 6.93 (d, J=8.8 Hz, 2H), 5.10-5.03 (m, 2H), 4.10-4.06 (m, 2H), 2.02-2.00 (m, 2H), 1.80 (s, 3H), 3.87-3.80 (m, 4H), 2.96-2.86 (m, 4H), 2.86-2.80 (m, 1H), 2.78-2.74 (m, 1H), 1.86 (d, J=2.4 Hz, 3H).

Example 16 calcium(S)-3-(4-((3-((2-methyl-6,7-dihydrothieno[3,2-c]pyridin-5(4H)-yl)methyl)benzyl)oxy)phenyl)hex-4-ynoate(S)-3-(4-((3-((2-methyl-6,7-dihydrothieno[3,2-c]pyridin-5(4H)-yl)methyl)benzyl)oxy)phenyl)hex-4-ynoate

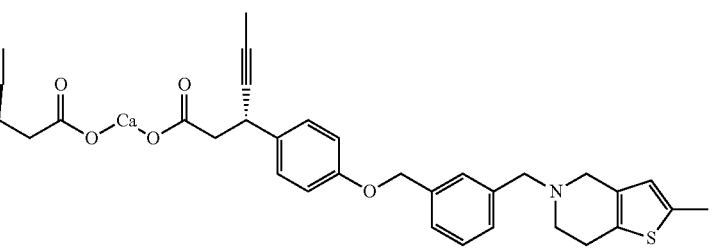

¹H NMR (DMSO-d₆, 400 MHz) δ: 7.40 (s, 1H), 7.35-7.23 (m, 5H), 6.88 (d, J=8.4 Hz, 2H), 6.41 (s, 1H), 5.04 (s, 2H), 4.00 (s$_{(br)}$, 1H), 3.64 (s, 2H), 3.32 (s, 2H), 2.68 (s, 4H), 2.40-2.37 (m, 1H), 2.33 (s, 3H), 2.27-2.21 (m, 1H), 1.74 (d, J=2 Hz, 3H).

Example 17 calcium (S)-3-(4-((3-((2-methyl-6,7-dihydrothiazolo[4,5-c]pyridin-5(4H)-yl)methyl)benzyl)oxy)phenyl)hex-4-ynoate(S)-3-(4-((3-((2-methyl-6,7-dihydrothiazolo[4,5-c]pyridin-5(4H)-yl)methyl)benzyl)oxy)phenyl)hex-4-ynoate

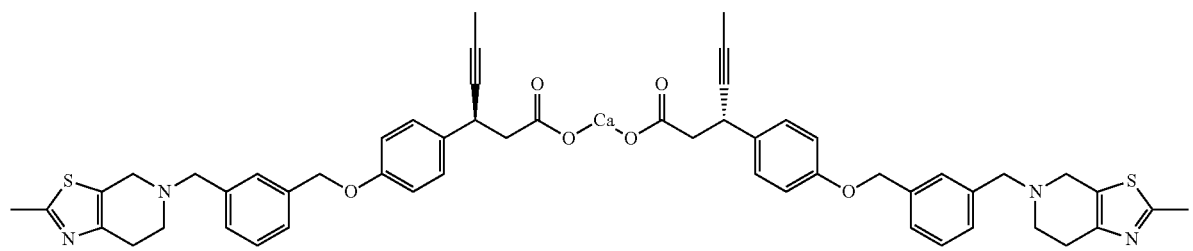

¹H NMR (DMSO-d₆, 400 MHz) δ: 7.41 (s, 1H), 7.34-7.23 (m, 5H), 6.89 (d, J=8.8 Hz, 2H), 5.01 (s, 2H), 4.05-3.99 (m, 1H), 3.68 (s, 2H), 3.56 (s, 2H), 2.76-2.74 (m, 2H), 2.68 (s$_{(br)}$, 2H), 2.56 (s, 3H), 2.40-2.36 (m, 1H), 2.26-2.22 (m, 1H), 1.73 (d, J=2.4 Hz, 3H).

Example 18

(S)-3-(4-((3-((2-(Difluoromethyl)-6,7-dihydrothieno[3,2-c]pyridin-5(4H)-yl)methyl)benzyl)oxy)phenyl)hex-4-ynoic acid

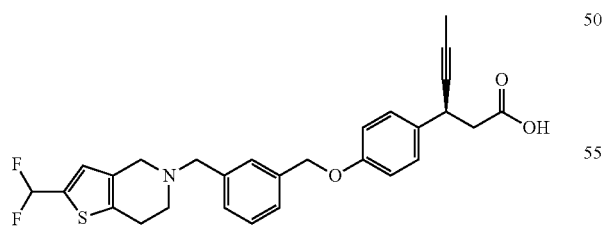

¹H NMR (CDCl₃, 400 MHz) δ: 7.39-7.26 (m, 6H), 6.91-6.59 (m, 4H), 5.03 (s, 2H), 4.12-4.10 (m, 1H), 3.73 (s, 2H), 3.55 (s, 2H), 2.88-2.64 (m, 6H), 1.82 (d, J=2.4 Hz, 3H).

Example 19
Calcium (S)-3-(4-((3-((2-bromo-6,7-dihydrothieno[3,2-c]pyridin-5(4H)-yl)methyl)benzyl)oxy)phenyl)hex-4-ynoate
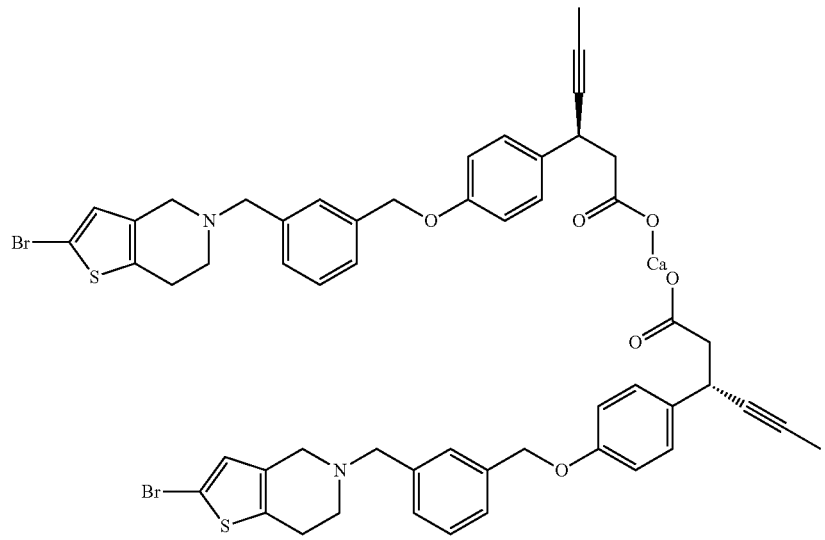
$^1$H NMR (DMSO-d$_6$, 400 MHz) δ: 7.41 (s, 1H), 7.37-7.24 (m, 5H), 6.93-6.89 (m, 3H), 5.06 (s, 2H), 3.96-3.94 (m, 1H), 3.66 (s, 2H), 3.38 (s, 2H), 2.71 (s, 4H), 2.49-2.32 (m, 2H), 1.76 (d, J=2.4 Hz, 3H).
Example 20
Calcium (S)-3-(4-((3-((3,4-dihydroisoquinolin-2(1H)-yl)methyl)benzyl)oxy)phenyl)hex-4-ynoate
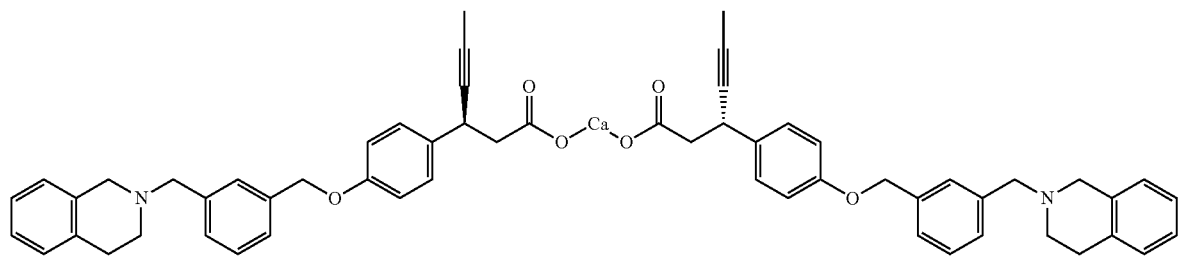
$^1$H NMR (DMSO-d$_6$, 400 MHz) δ: 7.37 (s, 1H), 7.35-7.23 (m, 5H), 7.11-7.07 (m, 3H), 6.98-6.97 (m, 1H), 6.89 (d, J=8.8 Hz, 2H), 5.05 (s, 2H), 3.99-3.97 (m, 1H), 3.64 (s, 2H), 3.52 (s, 2H), 2.79-2.77 (m, 2H), 2.65-2.64 (m, 2H), 2.42-2.36 (m, 1H), 2.28-2.22 (m, 1H), 1.74 (d, J=2.4 Hz, 3H).

Example 21

(S)-3-(4-((3-((7,8-Dihydropyrido[4,3-d]pyrimidin-6(5H)-yl)methyl)benzyl)oxy)phenyl)hex-4-ynoic acid

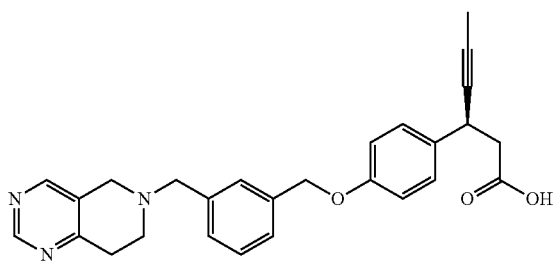 [SMILES: CC#C[C@@H](CC(=O)O)c1ccc(OCc2cccc(CN3CCc4ncncc4C3)c2)cc1]

¹H NMR (CDCl₃, 400 MHz) δ: 8.94 (s, 1H), 8.30 (s, 1H), 7.45 (s, 1H), 7.38-7.25 (m, 5H), 6.86 (dd, J=2, 6.8 Hz, 2H), 5.15-5.09 (m, 2H), 4.06-4.03 (m, 1H), 3.78-3.62 (m, 4H), 2.89-2.73 (m, 6H), 1.82 (d, J=2.4 Hz, 3H).

Example 22

(S)-3-(4-((3-((1-Methylpyrrolo[3,4-c]pyrazol-5(1H,4H,6H)-yl)methyl)benzyl)oxy)phenyl)hex-4-ynoic acid

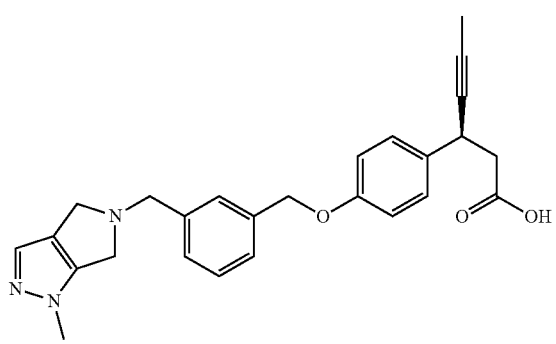 [SMILES: CC#C[C@@H](CC(=O)O)c1ccc(OCc2cccc(CN3Cc4cnn(C)c4C3)c2)cc1]

¹H NMR (CDCl₃, 400 MHz) δ: 7.43-7.24 (m, 6H), 7.17 (s, 1H), 6.88 (td, J=5.2, 8.4 Hz, 2H), 5.03 (s, 2H), 4.07 (s, 2H), 4.02-3.97 (m, 5H), 3.75 (s, 3H), 2.78-2.72 (m, 1H), 2.66-2.60 (m, 1H), 1.80 (d, J=2.4 Hz, 3H).

Example 23

(3S)-3-(4-((3-(6-Oxa-3-azabicyclo[3.1.1]heptan-3-ylmethyl)benzyl)oxy)phenyl)hex-4-ynoic acid

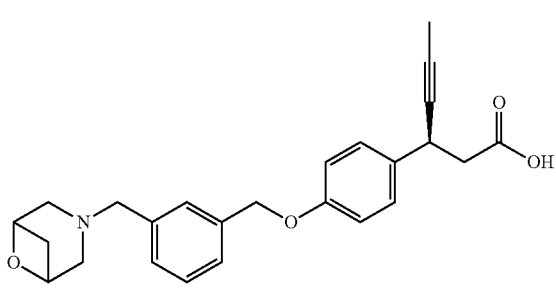 [SMILES: CC#C[C@@H](CC(=O)O)c1ccc(OCc2cccc(CN3CC4CC(C3)O4)c2)cc1]

¹H NMR (CDCl₃, 400 MHz) δ:7.53-7.25 (m, 6H), 6.89 (d, J=8.4 Hz, 2H), 5.09 (s, 2H), 4.54-4.52 (m, 2H), 4.05-3.93 (m, 3H), 3.24-2.94 (m, 4H), 2.81-2.75 (m, 1H), 2.69-2.63 (m, 1H), 2.42 (d, J=8.8 Hz, 2H), 1.83 (d, J=2.4 Hz, 3H).

Example 24

(S)-3-(4-((3-(Indolin-1-ylmethyl)benzyl)oxy)phenyl)hex-4-ynoic acid

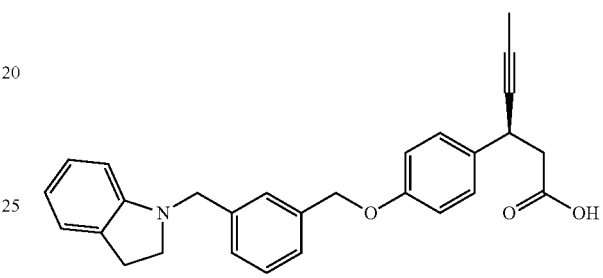

¹H NMR (CDCl₃, 400 MHz) δ: 7.41 (s, 1H), 7.37-7.25 (m, 5H), 7.10-7.05 (m, 2H), 6.93-6.89 (m, 2H), 6.70-6.66 (m, 1H), 6.51 (d, J=7.6 Hz, 1H), 5.03 (s, 2H), 4.26 (s, 2H), 4.07-4.02 (m, 1H), 3.30 (t, J=8.4 Hz, 2H), 2.96 (t, J=8.4 Hz, 2H), 2.83-2.76 (m, 1H), 2.73-2.67 (m, 1H), 1.83 (d, J=2.4 Hz, 3H).

Example 25

(S)-3-(4-((3-((5,6-Dihydro-[1,2,4]triazolo[4,3-a]pyrazin-7(8H)-yl)methyl)benzyl)oxy)phenyl)hex-4-ynoic acid

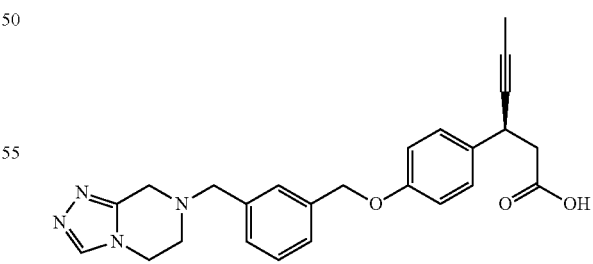

¹H NMR (CD₃OD, 400 MHz) δ: 8.50 (s, 1H), 7.49 (s, 1H), 7.40-7.35 (m, 3H), 7.28 (d, J=6.8 Hz, 2H), 6.93 (d, J=6.8 Hz, 2H), 5.01 (s, 2H), 4.15-4.11 (m, 2H), 4.00-3.97 (m, 1H), 3.87-3.83 (m, 4H), 2.97-2.94 (m, 2H), 2.66-2.62 (m, 2H), 1.81 (d, J=2.4 Hz, 3H).

Example 26

(S)-3-(4-((3-((2-Cyclopropyl-6,7-dihydrooxazolo[4,5-c]pyridin-5(4H)-yl)methyl)benzyl)oxy)phenyl)hex-4-ynoic acid

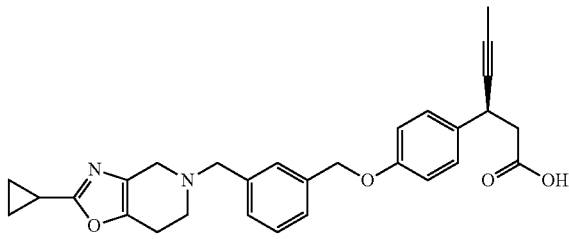 [SMILES: CC#C[C@@H](CC(=O)O)c1ccc(OCc2cccc(CN3CCc4oc(C5CC5)nc4C3)c2)cc1]

$^1$H NMR (CDCl$_3$, 400 MHz) δ: 7.52-7.20 (m, 6H), 6.81 (d, J=8.8 Hz, 2H), 5.21-5.12 (m, 2H), 4.00-3.95 (m, 1H), 3.78-3.67 (m, 2H), 3.23-2.59 (m, 8H), 2.04-1.97 (m, 1H), 1.81 (d, J=2.4 Hz, 3H), 1.00-0.96 (m, 4H).

Example 27

(3S)-3-(4-((3-((5-Benzylhexahydropyrrolo[3,4-c]pyrrol-2(1H)-yl)methyl)benzyl)oxy)phenyl)hex-4-ynoic acid compound with formic acid

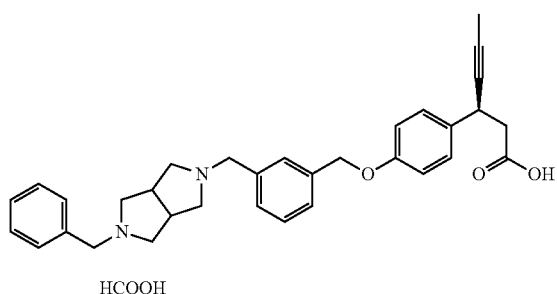 [SMILES: CC#C[C@@H](CC(=O)O)c1ccc(OCc2cccc(CN3CC4CN(Cc5ccccc5)CC4C3)c2)cc1 ; "HCOOH"]

$^1$H NMR (CDCl$_3$, 400 MHz) δ: 8.45 (s$_{(br)}$, 0.78H, HCOOH), 7.52-7.15 (m, 9H), 7.16 (d, J=7.2 Hz, 1H), 6.78 (dd, J=2.8, 11.6 Hz, 2H), 5.12 (s, 2H), 4.05-4.00 (m, 1H), 3.93-3.68 (m, 4H), 3.04-3.01 (m, 2H), 2.83-2.78 (m, 3H), 2.68-2.64 (m, 1H), 2.58-2.40 (m, 6H), 1.77 (d, J=2.4 Hz, 3H).

Example 28

(S)-3-(4-((3-((4H-Thieno[2,3-c]pyrrol-5(6H)-yl)methyl)benzyl)oxy)phenyl)hex-4-ynoic acid

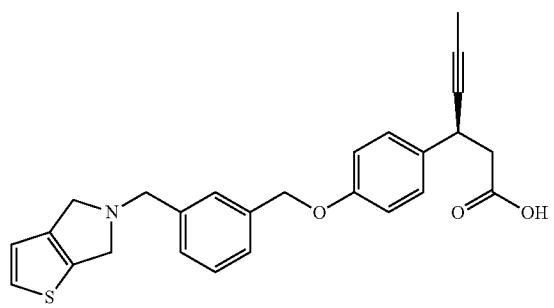 [SMILES: CC#C[C@@H](CC(=O)O)c1ccc(OCc2cccc(CN3Cc4ccsc4C3)c2)cc1]

$^1$H NMR (CDCl$_3$, 400 MHz) δ: 7.43 (s, 1H), 7.39-7.24 (m, 6H), 6.86 (d, J=8.4 Hz, 2H), 6.80 (d, J=5.2 Hz, 1H), 5.06-4.99 (m, 2H), 4.17-4.00 (m, 7H), 2.77-2.71 (m, 1H), 2.65-2.59 (m, 1H), 1.80 (d, J=2.4 Hz, 3H).

Example 29

6-(3-((4-((S)-1-carboxypent-3-yn-2-yl)phenoxy)methyl)benzyl)-6,7-dihydro-5H-pyrrolo[3,4-d]pyrimidin-6-ium formate

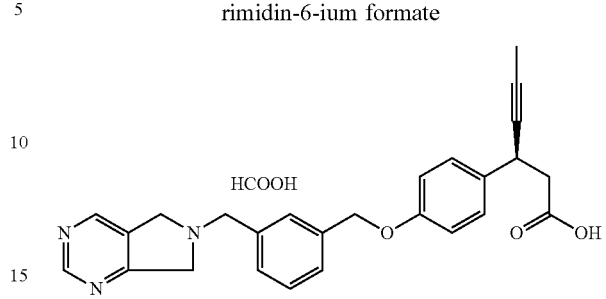

$^1$HNMR (CDCl$_3$, 400 MHz) δ: 8.98 (s, 1H), 8.63 (s, 1H), 8.37 (s, 1H), 7.45 (s, 1H), 7.37-7.31 (m, 3H), 7.25 (d, J=8.8 Hz, 2H), 6.93 (d, J=8.8 Hz, 2H), 5.08 (s, 2H), 3.95-3.90 (m, 7H), 2.55-2.52 (m, 1H), 2.12 (s, 3H).

Example 30

1-(3-((4-((S)-1-carboxypent-3-yn-2-yl)phenoxy)methyl)benzyl)-7-methoxy-1,2,3,4-tetrahydroquinolin-1-ium formate

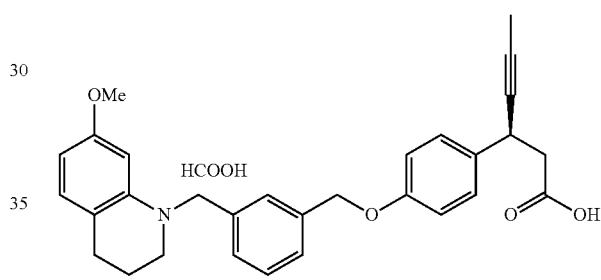

$^1$HNMR (CDCl$_3$, 400 MHz) δ 8.21 (s), 0.28 (formate), 7.33-7.28 (m, 3H), 7.25 (d, J=8.8 Hz, 2H), 7.19 (d, J=7.2 Hz, 1H), 6.91 (d, J=8.4 Hz, 2H), 6.55 (d, J=2.8 Hz, 1H), 6.51-6.48 (dd, J=8.8 Hz & 2.8 Hz, 1H), 6.39 (d, J=8.8 Hz, 1H), 5.0 (s, 2H), 4.39 (s, 2H), 3.95-3.90 (m, 3H), 3.60 (m, 4H), 3.24 (t, 3H), 2.70 (m, 2H), 2.58 (d, 2H), 2.06 (t, 2H), 1.07-1.08 (s, 3H).

Example 31

(S)-3-(4-((3-((2-Chloro-6,7-dihydrothiazolo[5,4-c]pyridin-5(4H)-yl)methyl)benzyl)oxy)phenyl)hex-4-ynoic acid

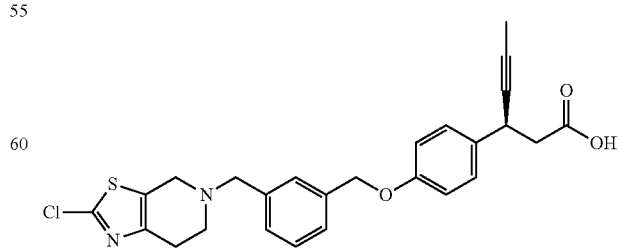

$^1$H NMR (CDCl$_3$, 400 MHz) δ: 7.41-7.30 (m, 3H), 7.35-7.27 (m, 3H), 6.90 (d, J=8.4 Hz, 2H), 5.07 (s, 1H), 4.07-4.02 (m, 1H), 3.82 (s, 2H), 3.72 (s, 2H), 2.98-2.95 (m, 2H), 2.86-2.68 (m, 5H), 1.83 (d, J=2.4 Hz, 3H).

Example 32

(S)-3-(4-((3-((2-Bromo-6,7-dihydrothiazolo[5,4-c]pyridin-5(4H)-yl)methyl)benzyl)oxy)phenyl)hex-4-ynoic acid

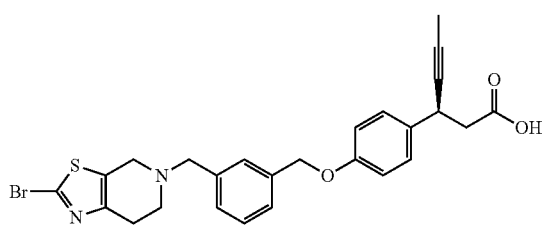 [SMILES: CC#C[C@@H](CC(=O)O)c1ccc(OCc2cccc(CN3CCc4nc(Br)sc4C3)c2)cc1]

¹H NMR (CDCl₃, 400 MHz) δ: 7.39-7.35 (m, 3H), 7.29-7.26 (m, 3H), 6.90 (d, J=8.4 Hz, 2H), 5.05 (s, 2H), 4.06-4.01 (m, 1H), 3.79 (s, 2H), 3.70 (s, 2H), 2.92-2.66 (m, 6H), 1.82 (d, J=2.4 Hz, 3H).

Example 33

(S)-3-(4-((3-(pyrrolo[3,4-c]pyrazol-5(1H,4H,6H)-ylmethyl)benzyl)oxy)phenyl) hex-4-ynoic acid

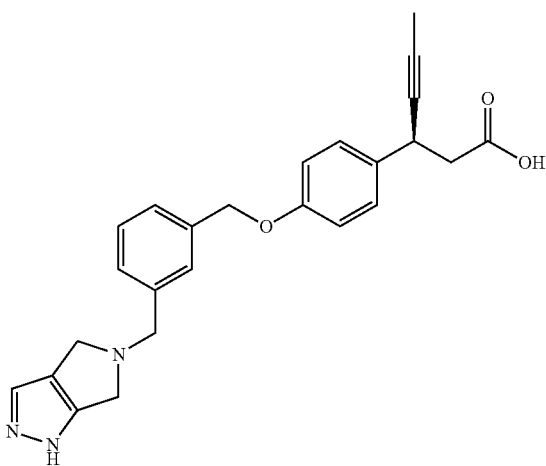 [SMILES: CC#C[C@@H](CC(=O)O)c1ccc(OCc2cccc(CN3Cc4cn[nH]c4C3)c2)cc1]

¹H-NMR (CDCl₃, 400 MHz):—δ 7.32-7.53 (m, 3H), 7.19-7.29 (m, 4H), 6.82-6.84 (m, 2H), 5.16 (s, 2H), 3.90-4.06 (m, 5H), 3.57 (s, 2H), 2.80-2.85 (m, 1H), 1.81 (s, 3H);

Example 34

(S)-3-(4-((3-((2-(hydroxymethyl)-6,7-dihydrothieno[3,2-c]pyridin-5(4H)-yl)methyl)benzyl)oxy)phenyl)hex-4-ynoic acid

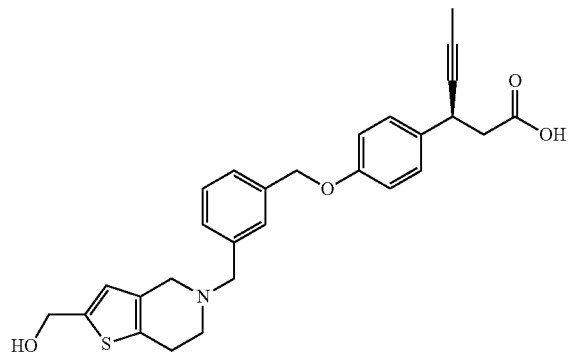 [SMILES: CC#C[C@@H](CC(=O)O)c1ccc(OCc2cccc(CN3CCc4sc(CO)cc4C3)c2)cc1]

¹H-NMR (DMSO, 400 MHz):—δ 7.38 (s, 1H), 7.23-7.33 (m, 5H), 6.92 (d, J=8.8 Hz, 2H), 6.56 (s, 1H), 5.35 (s, 2H), 3.91-3.94 (m, 1H), 3.72-3.84 (m, 4H), 3.40-3.50 (m, 2H (merged), 2.86-2.94 (m, 2H), 2.73-2.76 (m, 2H), 2.50-2.58 (m, 2H), 1.76 (s, 3H);

Example 35

(S)-5-(3-((4-(1-carboxypent-3-yn-2-yl)phenoxy)methyl)benzyl)-4,5,6,7-tetrahydrothieno[3,2-c]pyridine-2-carboxylic acid

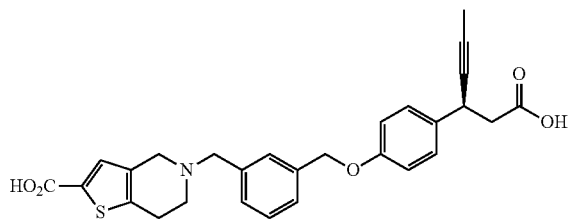 [SMILES: CC#C[C@@H](CC(=O)O)c1ccc(OCc2cccc(CN3CCc4sc(C(=O)O)cc4C3)c2)cc1]

¹H NMR: (DMSO-d₆, 400 MHz):—7.42 (s, 1H), 7.34-7.31 (m, 2H), 7.27-7.26 (m, 1H), 7.22 (d, J=8.8 Hz, 2H), 6.99 (s, 1H), 6.90 (d, J=8.8 Hz, 2H), 5.09 (s, 2H), 3.95-3.91 (m, 1H), 3.65 (s, 2H), 3.29 (s, 2H), 2.74-2.71 (m, 4H), 2.63-2.52 (m, 2H), 1.76 (s, 3H).

Example 36

3-cyclopropyl-3-(3-((3-((2-methyl-6,7-dihydrothieno[3,2-c]pyridin-5(4H)-yl)methyl)benzyl)oxy)phenyl)propanoic acid

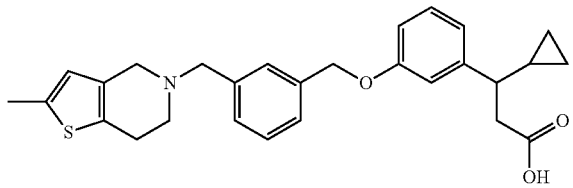 [SMILES: Cc1cc2c(s1)CCN(Cc1cccc(COc3cccc(C(CC(=O)O)C4CC4)c3)c1)C2]

¹H NMR: (DMSO-d₆, 400 MHz):—7.46 (s, 1H), 7.37-7.31 (m, 3H), 7.14 (t, J=8 Hz, 2H), 6.81-6.79 (m, 2H), 6.44 (s, 1H), 5.05 (s, 2H), 3.78 (s, 2H), 3.32 (s, 2H), 2.82-2.74 (m, 4H), 2.49-2.44 (m, 2H), 2.36-2.34 (m, 4H), 1.30-1.28 (m, 1H), 0.49-0.47 (m, 1H), 0.27-0.24 (m, 2H), 0.004-0.002 (m, 1H).

Example 37

(S)-3-(4-((3-((1-methyl-6,7-dihydro-1H-pyrrolo[3,2-c]pyridin-5(4H)-yl)methyl)benzyl)oxy)phenyl)hex-4-ynoic acid

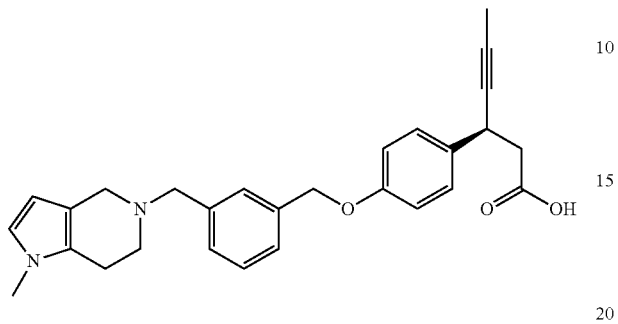

¹H NMR (CDCl₃, 400 MHz): δ 7.53 (s, 1H), 7.47-7.32 (d, 3H), 7.24-7.12 (m, 2H), 6.85 (d, 2H), 6.51 (d, 1H), 5.58 (d, 1H), 5.0-4.95 (d, 2H), 3.9-4.1 (m, 1H), 3.87 (d, 1H), 3.80 (d, 1H), 3.48 (s, 3H), 2.9-3.1 (m, 3H), 1.08 (m, 3H).

Example 38

(S)-3-(4-((3-((2-amino-6,7-dihydrothiazolo[5,4-c]pyridin-5(4H)-yl)methyl)benzyl)oxy)phenyl)hex-4-ynoic acid

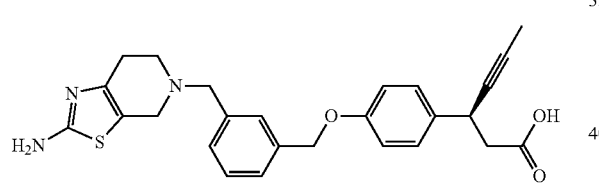

¹H NMR (DMSO-d₆, 400 MHz): δ 8.23 (s, 1H), 7.40 (s, 1H), 7.35 (d, 2H), 7.32-7.24 (m, 3H), 6.93 (d, J=8.4 Hz, 2H), 6.68 (s, 2H), 5.06 (s, 2H), 3.9-4.0 (m, 1H), 3.35 (s, 3H), 2.70-2.66 (m, 2H), 2.58 (d, 2H), 2.44 (d, 3H).

Example 39

Calcium (S)-3-(4-((3-((2-chloro-6,7-dihydrothieno[3,2-c]pyridin-5(4H)-yl)methyl)benzyl)oxy)phenyl)hex-4-ynoate

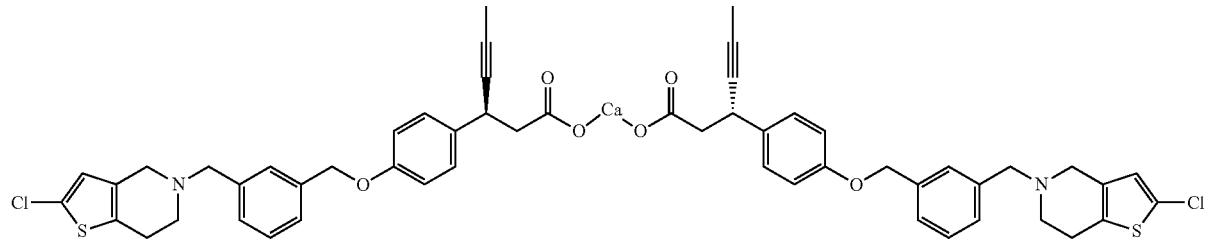

¹H NMR (CDCl₃, 400 MHz) δ: 7.39 (s, 1H), 7.36-7.23 (m, 5H), 6.88 (d, J=8.8 Hz, 2H), 6.78 (s, 1H), 5.04 (s, 2H), 3.99 (s₍br₎, 1H), 3.65 (s, 2H), 3.34 (s, 2H), 2.70 (s₍br₎, 4H), 2.37-2.31 (m, 1H), 2.25-2.19 (m, 1H), 1.73 (d, J=2.4 Hz, 3H).

Example 40

(S)-3-(4-((3-((2-carbamoyl-6,7-dihydrothieno[3,2-c]pyridin-5(4H)-yl)methyl)benzyl)oxy)phenyl)hex-4-ynoic acid

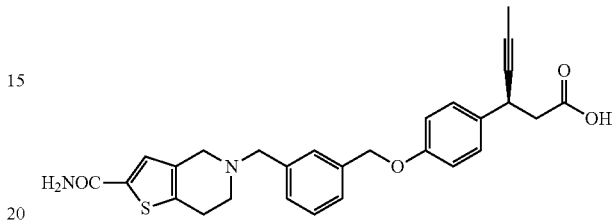

¹H NMR: (DMSO-d₆, 400 MHz):—12.22 (br s, 1H), 7.76 (br s, 1H), 7.42 (s, 1H), 7.37-7.25 (m, 7H), 6.94 (d, J=8.8 Hz, 2H), 5.07 (s, 2H), 3.95-3.91 (m, 1H), 3.68 (s, 2H), 3.43 (s, 2H), 2.78-2.76 (m, 2H), 2.72-2.70 (m, 2H), 2.60-2.57 (m, 2H), 1.77 (s, 3H).

Example 41

((S)-3-(4-((3-((2-isopropylpyrrolo[3,4-c]pyrazol-5(2H,4H,6H)-yl)methyl)benzyl)oxy)phenyl)hex-4-ynoic acid

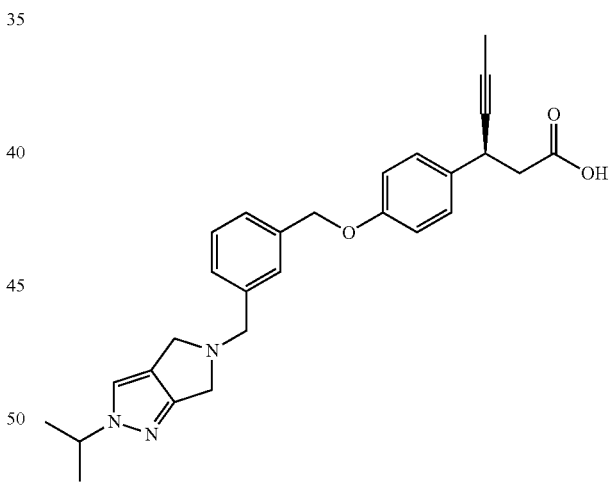

¹H-NMR (DMSO, 400 MHz): δ 12.25 (m, 2H), 7.48-7.51 (m, 2H), 7.39 (s, 3H), 7.27 (d, J=8.8 Hz, 2H), 6.95 (d, J=8.8 Hz, 2H), 5.09 (s, 2H), 4.40-4.47 (m, 1H), 4.10-4.20 (m, 2H), 3.70-3.90 (m, 4H), 2.66-2.66 (m, 2H), 1.77 (s, 3H), 1.36-1.38 (m, 6H);

Example 42

(S)-3-(4-((3-((2-(methoxycarbonyl)-6,7-dihydrothieno[3,2-c]pyridin-5(4H)-yl)methyl)benzyl)oxy)phenyl)hex-4-ynoic acid

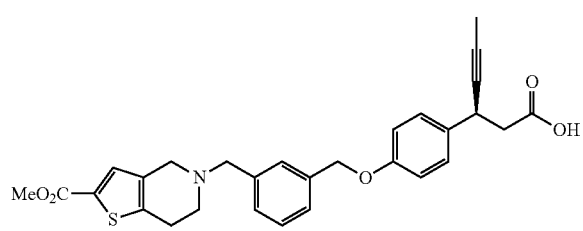 [SMILES: CC#C[C@@H](CC(=O)O)c1ccc(OCc2cccc(CN3CCc4sc(C(=O)OC)cc4C3)c2)cc1]

¹H NMR: (DMSO-d₆, 400 MHz):—12.22 (br s, 1H), 7.50 (s, 1H), 7.41 (s, 1H), 7.37-7.24 (m, 5H), 6.92 (d, J=8.4 Hz, 2H), 5.07 (s, 2H), 3.95-3.91 (m, 1H), 3.77 (s, 3H), 3.68 (s, 2H), 3.46 (s, 2H), 2.84-2.81 (m, 2H), 2.74-2.70 (m, 2H), 2.58-2.53 (m, 2H), 1.90 (s, 3H).

Example 43

(S)-3-(4-((3-((2-cyano-6,7-dihydrothieno[3,2-c]pyridin-5(4H)-yl)methyl)benzyl)oxy)phenyl)hex-4-ynoic acid

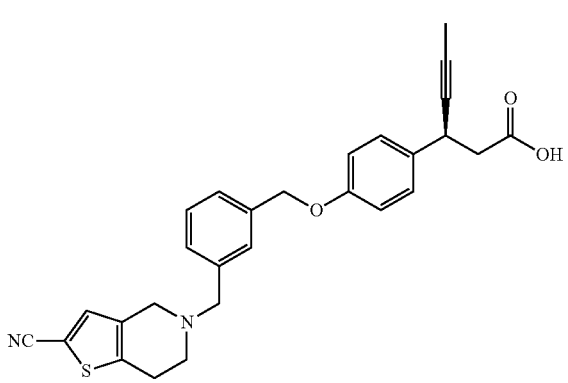 [SMILES: CC#C[C@@H](CC(=O)O)c1ccc(OCc2cccc(CN3CCc4sc(C#N)cc4C3)c2)cc1]

¹H-NMR (DMSO, 400 MHz): δ 8.83 (s, 1H), 7.24-7.41 (m, 6H), 6.92-6.94 (m, 2H), 5.09 (s, 2H), 3.91-3.94 (m, 1H), 3.73 (s, 2H), 3.45 (s, 2H), 2.86-2.94 (m, 2H), 2.73-2.76 (m, 2H), 2.50-2.58 (m, 2H), 1.76 (s, 3H);

Example 44

(S)-3-(4-((3-((2-formyl-6,7-dihydrothieno[3,2-c]pyridin-5(4H)-yl)methyl)benzyl)oxy)phenyl)hex-4-ynoic acid

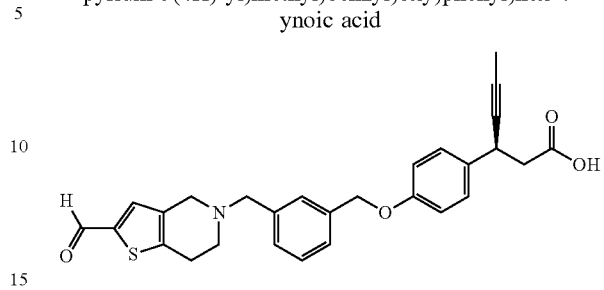

¹H NMR: (DMSO-d₆, 400 MHz):—9.79 (s, 1H), 7.70 (s, 1H), 7.42 (s, 1H), 7.36-7.31 (m, 3H), 7.26-7.24 (d, J=8 Hz, 2H), 6.94-6.92 (d, J=8 Hz, 2H), 5.07 (s, 2H), 3.93 (br s, 1H), 3.70 (s, 2H), 3.50 (s, 2H), 2.89 (s, 2H), 2.74 (s, 2H), 1.76 (s, 3H), 1.23 (s, 2H).

Example 45

S)-3-(4-((3-((2-methyl-6,7-dihydropyrazolo[1,5-a]pyrazin-5(4H)-yl)methyl)benzyl)oxy)phenyl)hex-4-ynoic acid

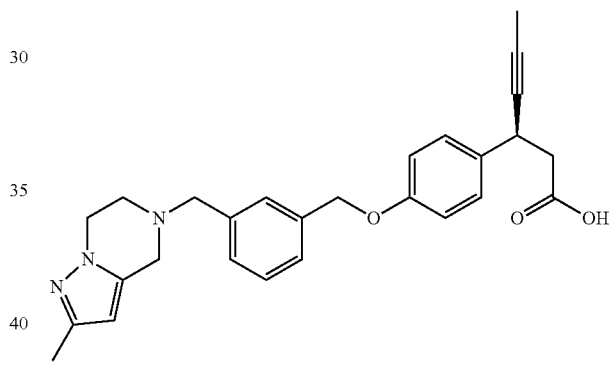

¹H NMR (DMSO-d₆, 400 MHz): δ 7.41 (s, 1H), 7.35 (d, J=6.4 Hz, 2H), 7.30 (m, 1H), 7.25 (d, J=8.8 Hz, 2H), 6.93 (d, J=8.4 Hz, 2H), 5.73 (s, 1H), 5.07 (s, 2H), 3.96-3.92 (m, 3H), 3.68 (s, 2H), 3.52 (s, 2H), 2.84 (t, 2H), 2.66 (t, 2H), 2.08 (s, 3H), 1.77 (s, 3H)

Example 46

(S)-3-(4-((3-((2-(methylcarbamoyl)-6,7-dihydrothieno[3,2-c]pyridin-5(4H)-yl)methyl)benzyl)oxy)phenyl)hex-4-ynoic acid

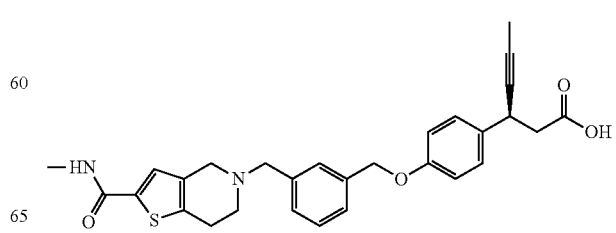

¹H NMR: (DMSO-d₆, 400 MHz):—7.42 (s, 1H), 7.35-7.24 (m, 6H), 7.1-6.93-6.91 (m, 2H), 5.07 (s, 2H), 3.9 (m, 1H), 3.68 (s, 2H), 3.41 (s, 2H), 2.71-2.70 (m, 2H), 2.67-2.66 (m, 6H), 1.76 (s, 3H).

Example 47

(S)-3-(4-((3-((2-(dimethylcarbamoyl)-6,7-dihydrothieno[3,2-c]pyridin-5(4H)-yl)methyl)benzyl)oxy)phenyl)hex-4-ynoic acid

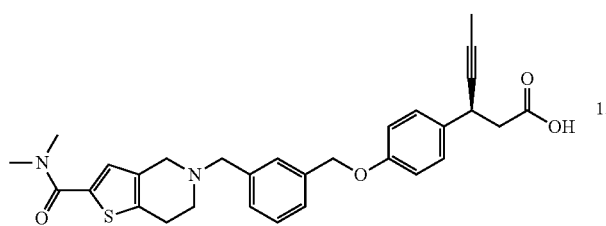

¹H NMR: (DMSO-d₆, 400 MHz):—7.53 (s, 1H), 7.40-7.22 (m, 4H), 7.1-6.68 (m, 3H), 5.08 (s, 2H), 4.12-4.03 (m, 1H), 3.78-3.71 (m, 2H), 3.50 (s, 2H), 3.17 (s, 6H), 2.95-2.88 (m, 2H), 2.83-2.63 (m, 2H), 1.83 (s, 3H).

Example 48

(3S)-3-(4-((3-((2-Methyl-5-(4-(methylsulfonyl)phenyl)pyrrolidin-1-yl)methyl)benzyl)oxy)phenyl)hex-4-ynoic acid

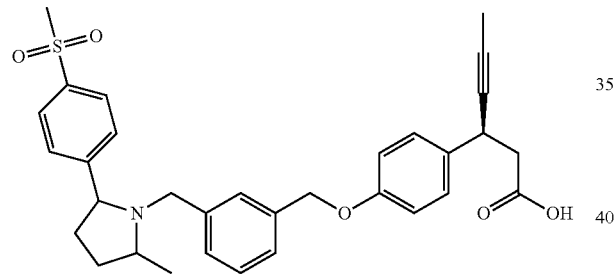

¹H NMR (CDCl₃, 400 MHz) δ: 7.93-7.90 (m, 2H), 7.82-7.76 (m, 2H), 7.53-7.16 (m, 7H), 6.92-6.86 (m, 3H), 5.11-5.01 (m, 3H), 4.45-4.30 (m, 1H), 4.07-3.98 (m, 3H), 3.30-3.20 (m, 1H), 3.097-3.090 (m, 3H), 3.03 (s, 1H), 2.87-2.68 (m, 4H), 2.33-1.98 (m, 8H), 1.84-1.82 (m, 5H), 1.62-1.60 (m, 4H)

Example 49

(S)-3-(4-((3-((2-(Methylsulfonyl)-7,8-dihydropyrido[4,3-d]pyrimidin-6(5H)-yl)methyl)benzyl)oxy)phenyl)hex-4-ynoic acid

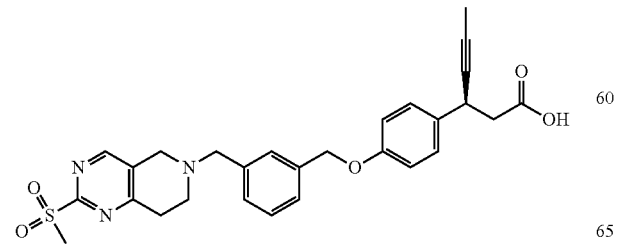

¹H NMR (CDCl₃, 400 MHz) δ: 8.48 (s, 1H), 7.43-7.27 (m, 6H), 6.91 (dd, J=8.8, 2 Hz, 2H), 5.07 (s, 2H), 4.07-4.03 (m, 1H), 3.80 (s, 2H), 3.72 (s, 2H), 3.32 (s, 3H), 3.15-3.09 (m, 2H), 2.92-2.89 (m, 2H), 2.84-2.78 (m, 1H), 2.74-2.68 (m, 1H), 1.83 (d, J=2.4 Hz, 3H)

Example 50

(S)-3-(4-((3-((2-Methoxy-7,8-dihydropyrido[4,3-d]pyrimidin-6(5H)-yl)methyl)benzyl)oxy)phenyl)hex-4-ynoic acid

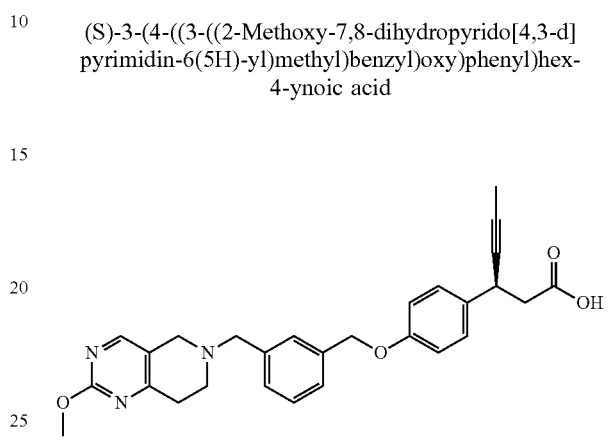

¹H NMR (CDCl₃, 400 MHz) δ: 8.09 (s, 1H), 7.53-7.26 (m, 6H), 6.87 (dd, J=6.8, 2 Hz, 2H), 5.17-5.08 (m, 2H), 4.07-4.02 (m, 1H), 3.98 (s, 3H), 3.75 (s_(br), 2H), 3.58 (s_(br), 2H), 2.88-2.63 (m, 6H), 1.82 (d, J=2.4 Hz, 3H)

Example 51

(3S)-3-(4-((3-((2-phenylpyrrolidin-1-yl)methyl)benzyl)oxy)phenyl)hex-4-ynoic acid

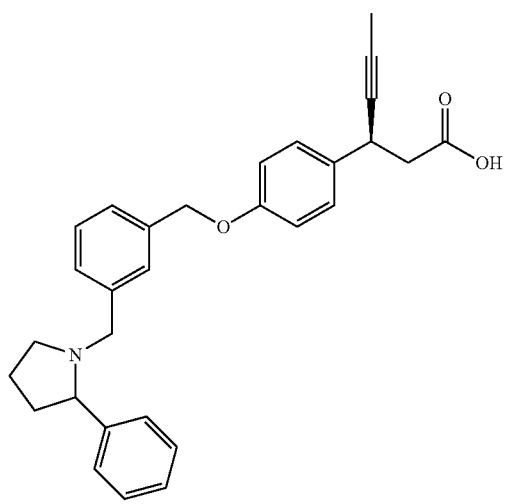 [SMILES: CC#C[C@@H](CC(=O)O)c1ccc(OCc2cccc(CN3CCCC3c3ccccc3)c2)cc1]

¹H-NMR (CDCl₃, 400 MHz): δ 7.43-7.45 (m, 2H), 7.21-7.35 (m, 9H), 6.89-6.91 (d, J=8 Hz, 2H), 5.0 (s, 2H), 4.03 (m, 1H), 3.81-3.85 (m, 1H), 3.37-3.41 (m, 1H), 3.11-3.17 (m, 3H), 2.74-2.80 (m, 1H), 2.64-2.69 (m, 1H), 3.37-2.14-2.51 (m, 2H), 1.85-1.92 (m, 1H), 1.81 (s, 3H), 1.71-1.75 (m, 2H);

Example 52

(S)-3-(4-((3-(Pyrrolidin-1-ylmethyl)benzyl)oxy)phenyl)hex-4-ynoic acid compound with formic acid

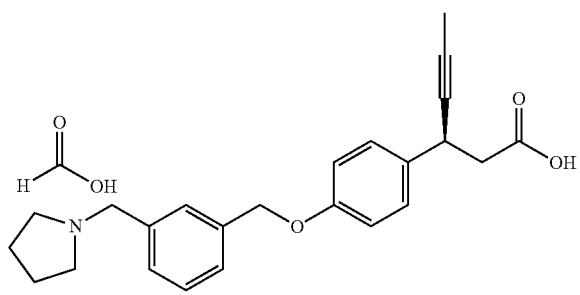

¹H NMR (CD₃OD, 400 MHz) δ: 8.51 (s, 1H, HCOOH), 7.60 (s, 1H), 7.55-7.45 (m, 3H), 7.28 (d, J=8.4 Hz, 2H), 6.91 (d, J=8.8 Hz, 2H), 5.14 (s, 2H), 4.34 (s, 2H), 4.02-3.98 (m, 1H), 3.27-3.24 (m, 4H), 2.62-2.50 (m, 2H), 2.08-2.04 (m, 4H), 1.80 (d, J=2.4 Hz, 3H)

Example 53

(S)-3-(4-((3-(Piperidin-1-yl methyl)benzyl)oxy)phenyl)hex-4-ynoic acid compound with formic acid

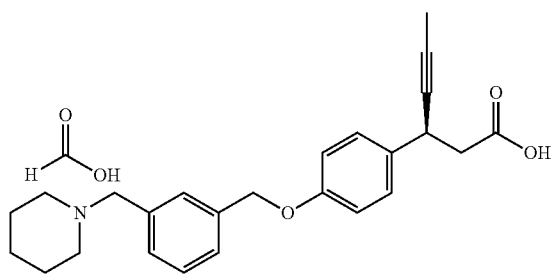

¹H NMR (CD₃OD, 400 MHz) δ: 8.50 (s, 1H, HCOOH), 7.58-7.43 (m, 4H), 7.29 (d, J=8.8, Hz, 2H), 6.91 (d, J=8.8 Hz, 2H), 5.15 (s, 2H), 4.23 (s, 2H), 4.09-4.03 (m, 1H), 3.12-3.08 (m, 4H), 2.63-2.49 (m, 2H), 1.83-1.79 (m, 7H), 1.64-1.61 (m, 2H)

Example 54

(S)-3-(4-((3-((1-isopropylpyrrolo[3,4-c]pyrazol-5(1H,4H,6H)-yl)methyl)benzyl)oxy)phenyl)hex-4-ynoic acid compound with formic acid

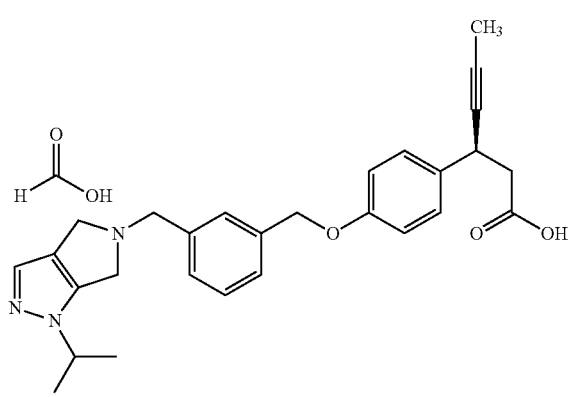

¹H NMR (CD₃OD, 400 MHz) δ: 8.41 (s, 1H, HCOOH), 7.54 (s, 1H), 7.43-7.40 (m, 3H), 7.29 (dd, J=7.2, 2 Hz, 2H), 7.21 (s, 1H), 6.93 (dd, J=6.8, 2 Hz, 2H), 5.11 (s, 2H), 4.45-4.41 (m, 1H), 4.14 (s, 2H), 4.07 (s, 2H), 4.02-3.95 (m, 1H), 3.88 (s, 2H), 2.63-2.59 (m, 2H), 1.80 (d, J=2.4 Hz, 3H), 1.42 (d, J=6.8 Hz, 6H).

Example 55

(R)-3-(4-((3-((2-methyl-6,7-dihydrothieno[3,2-c]pyridin-5(4H)-yl)methyl)benzyl)oxy)phenyl)hex-4-ynoic acid

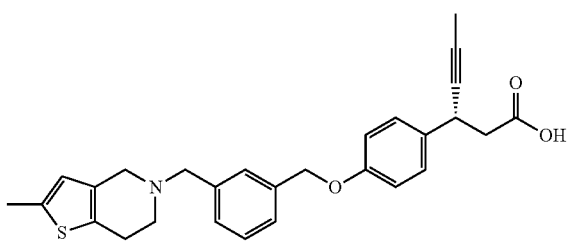 [SMILES: CC#C[C@H](CC(=O)O)c1ccc(OCc2cccc(CN3CCc4sc(C)cc4C3)c2)cc1]

¹H NMR (CDCl₃, 400 MHz) δ: 8.31 (s, 0.36H, Residual HCOOH), 7.47-7.25 (m, 6H), 6.86 (td, J=9.6, 2.8 Hz, 2H), 6.34 (s, 1H), 5.04 (s, 2H), 4.07-4.01 (m, 3H), 3.8 (s$_{(br)}$, 2H), 3.20-3.12 (m, 2H), 2.97-2.95 (m, 2H), 2.78-2.73 (m, 1H), 2.66-2.61 (m, 1H), 2.41 (s, 3H), 1.80 (d, J=2.4 Hz, 3H).

Example 56

(R)-3-(4-((3-((2-Methyl-6,7-dihydrothiazolo[5,4-c]pyridin-5(4H)-yl)methyl)benzyl)oxy)phenyl)hex-4-ynoic acid

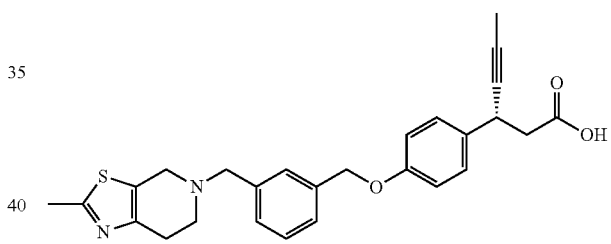

¹H NMR (CDCl₃, 400 MHz) δ: 8.15 (s, 0.3H, Residual HCOOH), 7.41-7.27 (m, 6H), 6.88 (d, J=8.4 Hz, 2H), 5.15-5.07 (m, 2H), 4.06-4.02 (m, 1H), 3.90-3.82 (m, 4H), 2.96-2.92 (m, 2H), 2.88-2.64 (m, 7H), 1.82 (d, J=2.4 Hz, 3H)

Example 57

(S)-3-(4-((3-((6,7-Dihydro-[1,2,3]triazolo[1,5-a]pyrazin-5(4H)-yl)methyl)benzyl)oxy)phenyl)hex-4-ynoic acid

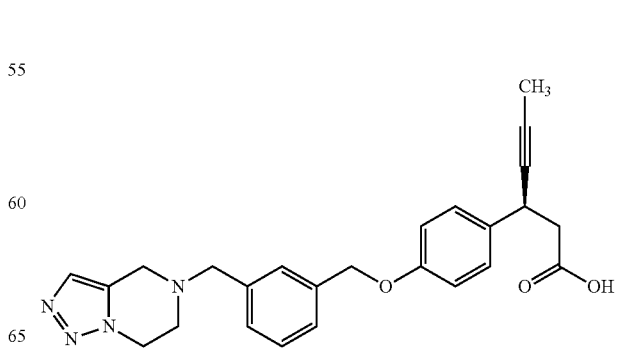

¹H NMR (CD₃OD, 400 MHz) δ: 7.59-7.58 (m, 2H), 7.58-7.43 (m, 3H), 7.29 (d, J=8.8 Hz, 2H), 6.93 (d, J=8.8 Hz, 2H), 5.14 (s, 2H), 4.58-4.55 (m, 2H), 4.19 (s, 2H), 4.15 (s, 2H), 4.01-3.97 (m, 1H), 3.44-3.41 (m, 2H), 2.70-2.58 (m, 2H), 1.81 (d, J=2.4 Hz, 3H).

Example 58

3-(4-((3-((2-Methyl-6,7-dihydrothieno[3,2-c]pyridin-5(4H)-yl)methyl)benzyl)oxy)phenyl)hex-4-ynoic acid

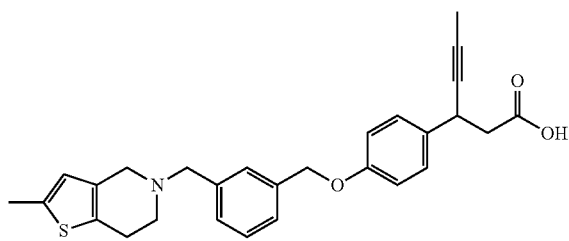

¹H NMR (CDCl₃, 400 MHz) δ: 7.42-4.27 (m, 5H), 6.87 (dd, J=11.2, 3 Hz, 2H), 6.34 (s, 1H), 5.05 (s, 2H), 4.06-4.02 (m, 2H), 3.98 (s, 2H), 3.74 (s, 2H), 3.10-3.04 (m, 2H), 2.92-2.89 (m, 2H), 2.79-2.73 (m, 1H), 2.67-2.61 (m, 1H), 2.41 (s, 3H), 1.81 (d, J=2.4 Hz, 3H).

Example 59

3-(4-((3-((2-Methyl-6,7-dihydrothiazolo[5,4-c]pyridin-5(4H)-yl)methyl)benzyl)oxy)phenyl)hex-4-ynoic acid

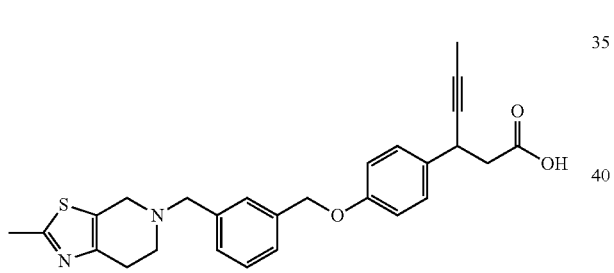

¹H NMR (CDCl₃, 400 MHz) δ: 7.42-7.35 (m, 4H), 7.29-7.27 (m, 2H), 6.88 (d, J=8.8 Hz, 2H), 5.14-5.07 (m, 2H), 4.06-4.03 (m, 1H), 3.93-3.85 (m, 4H), 2.99-2.97 (m, 2H), 2.86-2.64 (m, 7H), 1.82 (d, J=2.4 Hz, 3H)

Example 60

Calcium (S)-3-(4-((3-((2-chloro-6,7-dihydrothiazolo[5,4-c]pyridin-5(4H)-yl)methyl)benzyl)oxy)phenyl)hex-4-ynoate ¹H NMR (DMSO-d₆, 400 MHz) δ: 7.39 (s, 1H), 7.36-7.23 (M, 5H), 6.88 (d, J=8.8 Hz, 2H), 5.03 (s, 2H), 4.02-3.99 (m, 1H), 3.69 (s, 2H), 3.39 (s, 2H), 2.80-2.77 (m, 2H), 2.72-2.69 (m, 2H), 2.41-2.36 (m, 1H), 2.27-2.21 (m, 1H), 1.73 (d, J=2.4 Hz, 3H).

Example 61

(S)-3-(4-((3-((2-(cyclopropylcarbamoyl)-6,7-dihydrothieno[3,2-c]pyridin-5(4H)-yl)methyl)benzyl)oxy)phenyl)hex-4-ynoic acid

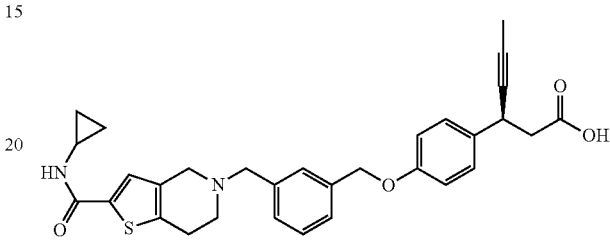

¹H NMR: (DMSO-d₆, 400 MHz):—8.34 (br s, 1H), 7.41 (s, 1H), 7.36-7.29 (m, 3H), 7.27-7.24 (m, 3H), 6.67 (d, J=8.4 Hz, 2H), 5.07 (s, 2H), 3.95-3.91 (m, 1H), 3.67 (s, 2H), 3.42 (s, 2H), 2.77-2.66 (m, 5H), 2.57-2.51 (m, 2H), 1.76 (s, 3H), 0.67-0.62 (m, 2H), 0.53-0.49 (m, 2H

Example 62

(S)-3-(4-((3-((2-(pyrrolidine-1-carbonyl)-6,7-dihydrothieno[3,2-c]pyridin-5(4H)-yl)methyl)benzyl)oxy)phenyl)hex-4-ynoic acid

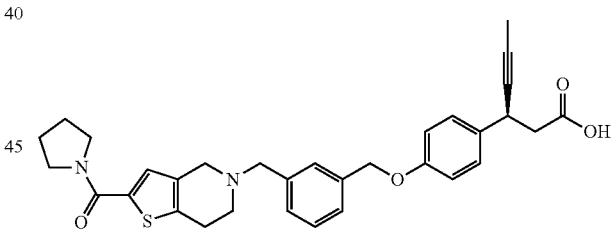

¹H NMR: (DMSO-d₆, 400 MHz):—7.42 (s, 1H), 7.37-7.26 (m, 3H), 7.25-7.13 (m, 3H), 6.93 (d, J=8.8 Hz, 2H), 5.07 (s, 2H), 3.94-3.87 (m, 1H), 3.68 (br s, 4H), 3.43 (br s, 4H), 2.80-2.73 (m, 4H), 2.59-2.50 (m, 2H), 2.91-1.81 (m, 4H), 1.76 (s, 3H)

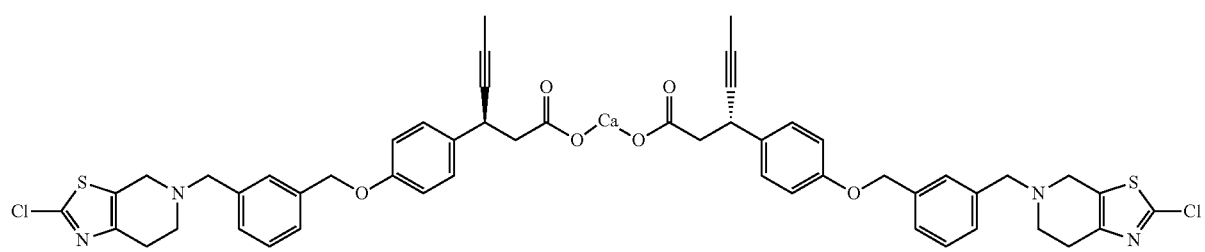

Example 63

(S)-3-(4-((3-((2-Aacetamido-6,7-dihydrothieno[3,2-c]pyridin-5(4H)-yl)methyl)benzyl)oxy)phenyl)hex-4-ynoic acid

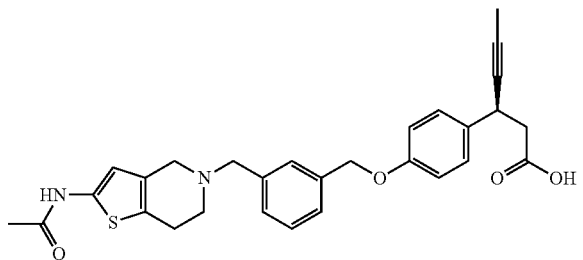 [SMILES: CC#C[C@@H](CC(=O)O)c1ccc(OCc2cccc(CN3CCc4sc(NC(C)=O)cc4C3)c2)cc1]

¹H NMR (CD₃OD, 400 MHz) δ: 7.56 (s, 1H), 7.50-7.41 (m, 3H), 7.28 (d, J=8.8 Hz, 2H), 6.92 (d, J=8.8 Hz, 2H), 6.35 (s, 1H), 5.12 (s, 2H), 4.15 (s, 2H), 4.01-3.97 (m, 1H), 3.84 (s, 2H), 3.25-3.22 (m, 2H), 2.96-2.93 (m, 2H), 2.66-2.53 (m, 2H), 2.10 (s, 3H), 1.79 (d, J=2.4 Hz, 3H).

Example 64

Calcium (S)-3-(4-((3-((2-cyclopropyl-6,7-dihydrooxazolo[4,5-c]pyridin-5(4H)-yl)methyl)benzyl)oxy)phenyl)hex-4-ynoate

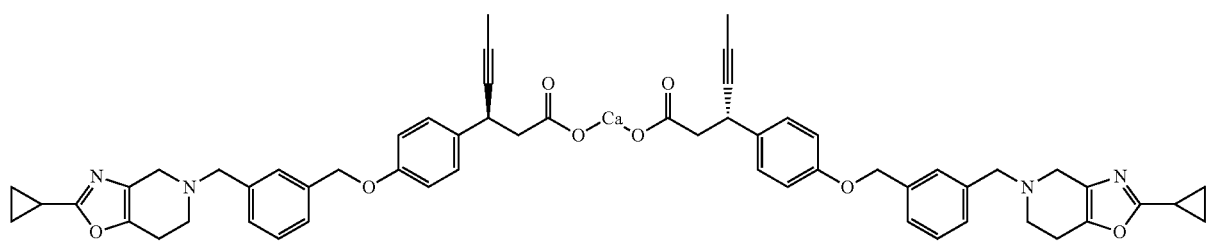

¹H NMR (DMSO-d₆, 400 MHz) δ:7.38 (s, 1H), 7.34-7.24 (m, 5H), 6.88 (d, J=8 Hz, 2H), 5.02 (s, 2H), 4.02-4.01 (m, 1H), 3.66 (s, 2H), 3.26 (s, 2H), 2.73-2.71 (m, 2H), 2.58 (s, 2H), 2.41-2.37 (m, 1H), 2.27-2.24 (m, 1H), 2.03-2.00 (m, 1H), 1.72 (s, 3H), 0.98-0.93 (m, 2H), 0.86-0.82 (m, 2H).

Example 65

(S)-3-(4-((3-((2-Nitro-6,7-dihydrothieno[3,2-c]pyridin-5(4H)-yl)methyl)benzyl)oxy)phenyl)hex-4-ynoic acid

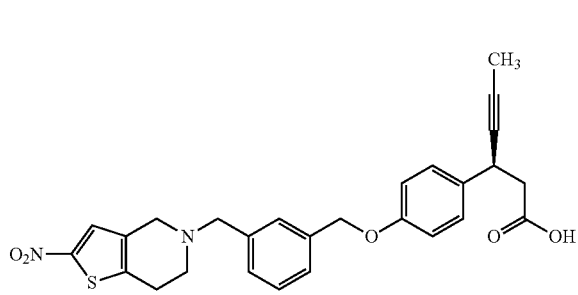 [SMILES: CC#C[C@@H](CC(=O)O)c1ccc(OCc2cccc(CN3CCc4sc([N+](=O)[O-])cc4C3)c2)cc1]

¹H NMR (CD₃OD, 400 MHz) δ: 7.80 (s, 1H), 7.69 (s, 1H), 7.61-7.52 (m, 3H), 7.30 (d, J=8.4 Hz, 2H), 6.95 (d, J=8.4 Hz, 2H), 5.17 (s, 2H), 4.54 (s, 2H), 4.30 (s, 2H), 4.01-3.99 (m, 1H), 3.66 (s₍br₎, 2H), 3.31-3.27 (m, 2H), 2.69-2.58 (m, 2H), 1.80 (d, J=2.4 Hz, 3H)

Example 66

(S)-3-(4-((3-((2-(Dimethylamino)-7,8-dihydropyrido[4,3-d]pyrimidin-6(5H)-yl)methyl)benzyl)oxy)phenyl)hex-4-ynoic acid compound with 2,2,2-trifluoroacetic acid

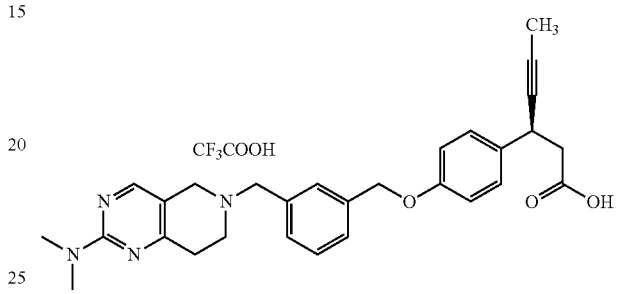

¹H NMR (CD₃OD, 400 MHz) δ: 8.00 (s, 1H), 7.54 (s, 1H), 7.45-7.42 (m, 3H), 7.28 (d, J=8.4 Hz, 2H), 6.93 (d, J=8.4 Hz, 2H), 5.13 (s, 2H), 4.01-3.99 (m, 3H), 3.74 (s, 2H), 3.14 (s, 6H), 3.10-3.07 (m, 2H), 2.90-2.87 (m, 2H), 2.64-2.60 (m, 2H), 1.80 (d, J=2.4 Hz, 3H).

Example 67

(S)-3-(4-((3-((2-Amino-7,8-dihydropyrido[4,3-d]pyrimidin-6(5H)-yl)methyl)benzyl)oxy)phenyl)hex-4-ynoic acid compound with 2,2,2-trifluoroacetic acid

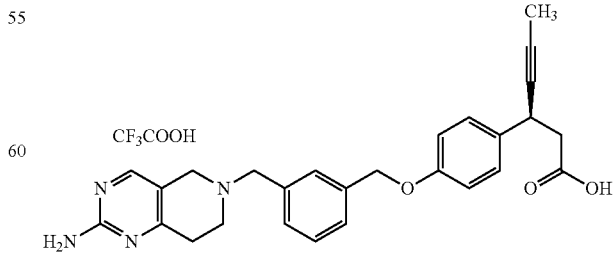

¹H NMR (CD₃OD, 400 MHz) δ: 8.10 (s, 1H), 7.67 (s, 1H), 7.62-7.54 (m, 3H), 7.30 (dd, J=6.8, 1.6 Hz, 2H), 6.96

(d, J=6.8, 1.6 Hz, 2H), 5.17 (s, 2H), 4.52 (s, 2H), 4.25 (s, 2H), 4.01-3.99 (m, 1H), 3.63 (s, 2H), 3.09-3.05 (m, 2H), 2.70-2.58 (m, 2H), 1.80 (d, J=2.4 Hz, 3H)

Example 68

(S)-3-(4-((3-((7,8-Dihydro-1,6-naphthyridin-6(5H)-yl)methyl)benzyl)oxy)phenyl) hex-4-ynoic acid

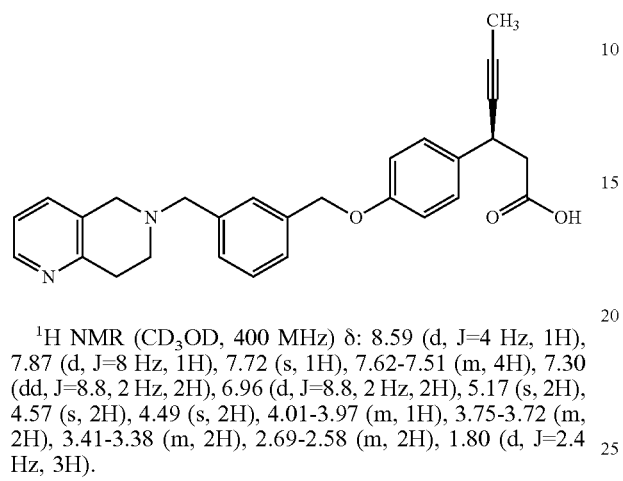

$^1$H NMR (CD$_3$OD, 400 MHz) δ: 8.59 (d, J=4 Hz, 1H), 7.87 (d, J=8 Hz, 1H), 7.72 (s, 1H), 7.62-7.51 (m, 4H), 7.30 (dd, J=8.8, 2 Hz, 2H), 6.96 (d, J=8.8, 2 Hz, 2H), 5.17 (s, 2H), 4.57 (s, 2H), 4.49 (s, 2H), 4.01-3.97 (m, 1H), 3.75-3.72 (m, 2H), 3.41-3.38 (m, 2H), 2.69-2.58 (m, 2H), 1.80 (d, J=2.4 Hz, 3H).

Example 69

(S)-3-(4-((3-((2-Cyclopropyl-6,7-dihydrothieno[3,2-c]pyridin-5(4H)-yl)methyl)benzyl)oxy)phenyl)hex-4-ynoic acid compound with 2,2,2-trifluoroacetic acid

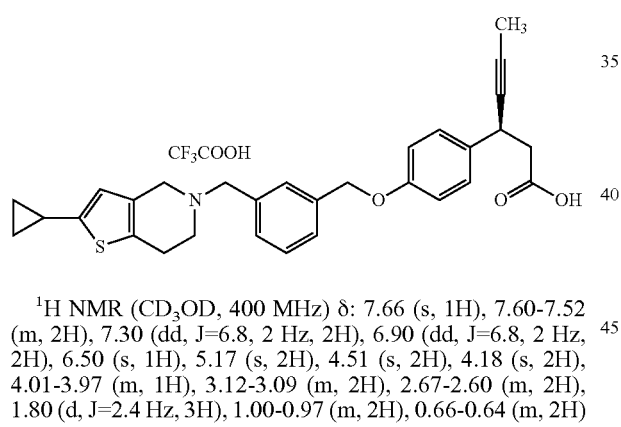

$^1$H NMR (CD$_3$OD, 400 MHz) δ: 7.66 (s, 1H), 7.60-7.52 (m, 2H), 7.30 (dd, J=6.8, 2 Hz, 2H), 6.90 (dd, J=6.8, 2 Hz, 2H), 6.50 (s, 1H), 5.17 (s, 2H), 4.51 (s, 2H), 4.18 (s, 2H), 4.01-3.97 (m, 1H), 3.12-3.09 (m, 2H), 2.67-2.60 (m, 2H), 1.80 (d, J=2.4 Hz, 3H), 1.00-0.97 (m, 2H), 0.66-0.64 (m, 2H)

Example 70

(S)-3-(4-((3-((2-Acetamido-6,7-dihydrothiazolo[5,4-c]pyridin-5(4H)-yl)methyl)benzyl)oxy)phenyl)hex-4-ynoic acid compound with 2,2,2-trifluoroacetic acid

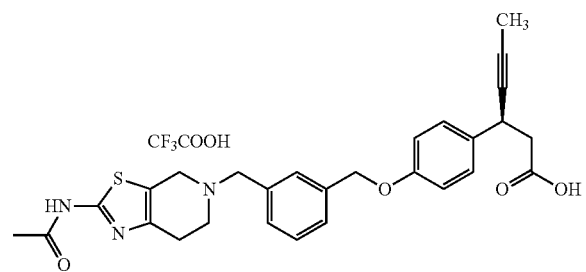 [SMILES: CC#C[C@@H](CC(=O)O)c1ccc(OCc2cccc(CN3CCc4nc(NC(C)=O)sc4C3)c2)cc1 ; "CF3COOH"]

$^1$H NMR (CD$_3$OD, 400 MHz) δ: 7.68 (s, 1H), 7.62-7.54 (m, 3H), 7.30 (d, J=8.8 Hz, 2H), 6.95 (d, J=8.8 Hz, 2H), 5.17 (s, 2H), 4.56 (s, 2H), 4.40 (s, 2H), 4.01-3.97 (m, 1H), 3.67 (s$_{(br)}$, 2H), 3.07-3.04 (m, 2H), 2.69-2.58 (m, 2H), 2.20 (s, 3H), 1.80 (d, J=2.4 Hz, 3H).

Example 71

(S)-3-(4-((3-((2-Ethyl-6,7-dihydrothieno[3,2-c]pyridin-5(4H)-yl)methyl)benzyl)oxy)phenyl)hex-4-ynoic acid

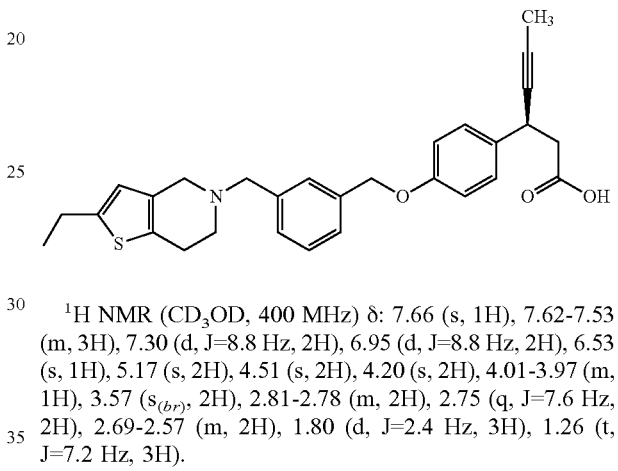

$^1$H NMR (CD$_3$OD, 400 MHz) δ: 7.66 (s, 1H), 7.62-7.53 (m, 3H), 7.30 (d, J=8.8 Hz, 2H), 6.95 (d, J=8.8 Hz, 2H), 6.53 (s, 1H), 5.17 (s, 2H), 4.51 (s, 2H), 4.20 (s, 2H), 4.01-3.97 (m, 1H), 3.57 (s$_{(br)}$, 2H), 2.81-2.78 (m, 2H), 2.75 (q, J=7.6 Hz, 2H), 2.69-2.57 (m, 2H), 1.80 (d, J=2.4 Hz, 3H), 1.26 (t, J=7.2 Hz, 3H).

Example 72

(S)-3-(4-((3-((2-Acetyl-6,7-dihydrothieno[3,2-c]pyridin-5(4H)-yl)methyl)benzyl)oxy)phenyl)hex-4-ynoic acid

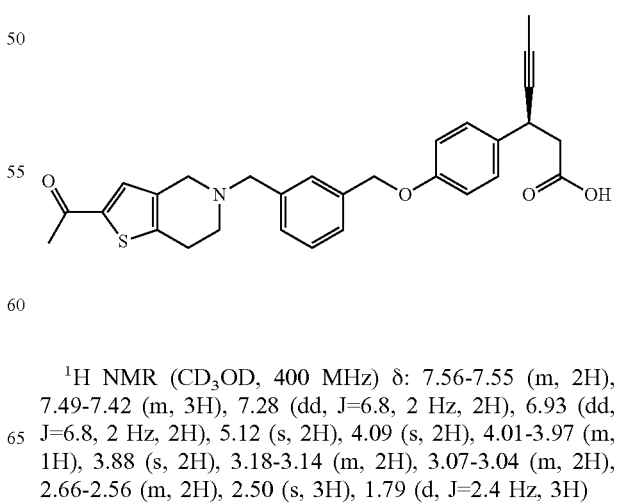

$^1$H NMR (CD$_3$OD, 400 MHz) δ: 7.56-7.55 (m, 2H), 7.49-7.42 (m, 3H), 7.28 (dd, J=6.8, 2 Hz, 2H), 6.93 (dd, J=6.8, 2 Hz, 2H), 5.12 (s, 2H), 4.09 (s, 2H), 4.01-3.97 (m, 1H), 3.88 (s, 2H), 3.18-3.14 (m, 2H), 3.07-3.04 (m, 2H), 2.66-2.56 (m, 2H), 2.50 (s, 3H), 1.79 (d, J=2.4 Hz, 3H)

Example 73

(S)-3-(4-((3-((2-((Methylamino)methyl)-6,7-dihydrothieno[3,2-c]pyridin-5(4H)-yl)methyl)benzyl)oxy)phenyl)hex-4-ynoic acid compound with 2,2,2-trifluoroacetic acid

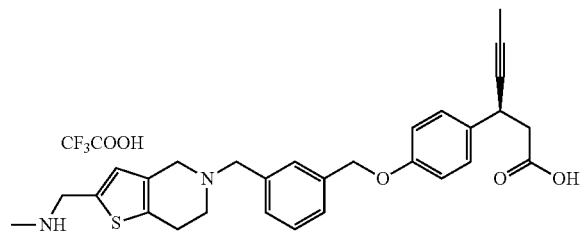 [SMILES: "CF3COOH" ; CC#C[C@@H](CC(=O)O)c1ccc(OCc2cccc(CN3CCc4sc(CNC)cc4C3)c2)cc1]

$^1$H NMR (CD$_3$OD, 400 MHz) δ: 7.67 (s, 1H), 7.62-7.60 (m, 1H), 7.55-7.53 (m, 2H), 7.30 (dd, J=6.8, 2 Hz, 2H), 7.03 (s, 1H), 6.96 (dd, J=6.8, 2 Hz, 2H), 5.17 (s, 2H), 4.52 (s, 2H), 4.36 (s, 2H), 4.27 (s, 2H), 4.01-3.98 (m, 1H), 3.62 (s$_{(br)}$, 2H), 3.24-3.21 (m, 2H), 2.71 (s, 3H), 2.69-2.62 (m, 2H), 1.81 (d, J=2.4 Hz, 3H).

The novel compounds of the present invention can be formulated into suitable pharmaceutically acceptable compositions by combining with suitable excipients by techniques and processes and concentrations as are well known.

The compounds of formula (1 or pharmaceutical compositions containing them are useful as ligands of the GPR 40 receptor suitable for humans and other warm blooded animals, and may be administered either by oral, topical or parenteral administration.

The quantity of active component, that is, the compounds of formula (I) according to this invention, in the pharmaceutical composition and unit dosage form thereof may be varied or adjusted widely depending upon several factors such as the particular application method, the potency of the particular compound and the desired concentration.

Biological Activity:

The biological activity of the compounds of the present invention was tested in the following in vitro and in vivo models mentioned here.

Summary of the In Vitro Screening Protocol

To determine the EC$_{50}$ of the compounds on intracellular Ca$^{2+}$ flux using a fluorescent assay (FLIPR)

GPR40 expressing stable cells were seeded at 25,000 numbers/well. 50 μL/well of assay buffer (20 mM HEPES+ 1×HBSS) was added to the cells and the cells were cultured for 20 min at 37° C. Cells were loaded with 50 μL/well of Calcium 5 dye and cultured for 45 min at 37° C.

The cells were challenged with compounds at a top concentration of 1000 nM (1:3 step down dilution—10 points). Intracellular Calcium flux was assessed by use of Screen Works 3.1 tool and statistical analysis was carried using Graph Pad Prism 4

Many of the compounds of the present invention demonstrated nanomolar potency and significant % stimulation on intracellular Ca$^{2+}$ flux when measured using fluorescent (FLIPR) assay The compounds exhibited potency in nanomolar range. (Table 1)

TABLE 1

In vitro EC50 values of the GPR 40 agonists of the present invention in FLIPR assay

| Compound | EC$_{50}$ (nM) |
|---|---|
| 1 | 117 |
| 7 | 1.8 |
| 16 | 2.72 |
| 17 | 10.2 |
| 19 | 2.32 |
| 22 | 36.3 |

Promoter-Luciferase Assay to Measure GPR40 Activation

GPR40 activation was measured in HEK293 cells stably transfected with GPR40 cDNA (ChemiBrite cell lines from Millipore, US). These cells were transiently transfected with a pGL2 (Promega Inc.) plasmid having a 5×SRE sequence, cloned 5' of a luciferase gene along with a β-galactosidase plasmid as normalizing control. Briefly, 35000 cells/well were seeded in a 96 well plates. After overnight incubation at 37° C., the cells were washed with PBS and transfected with the 5×-SRE-Luciferase plasmid and the β-galactosidase plasmid. 6 h post transfection, media was removed and replaced with fresh media with different concentration of drugs and incubated for 16 more hours. The cells were then lysed in 50 μL of Glo-Lysis buffer (Promega) for 30 min at room temperature. The cells were then centrifuged and lysates were collected. Luciferase activity was measured by adding 100 μL of luciferase substrate (Promega) in 20 μL of lysate and measuring the luminescence in luminometer. The θ-galactosidase activity was also measured by adding 20 μL of lysates with 20 μL of β-galactosidase buffer (Promega) and monitoring the absorbance at 415 nm. Luciferase values were divided by β-galactosidase values to normalize transfection efficiency (Table 2)

TABLE 2

In vitro EC50 values of the GPR 40 agonists of the present invention in Luciferase assay.

| Compound # | EC$_{50}$ (nM) |
|---|---|
| 1 | 7.5 |
| 7 | 1.49 |
| 8 | 11.8 |
| 10 | 16.9 |
| 12 | 5.6 |
| 13 | 0.8 |
| 14 | 0.8 |
| 15 | 4.6 |
| 16 | 4.6 |
| 17 | 4.7 |
| 18 | 8.8 |
| 19 | 0.2 |
| 20 | 2.7 |
| 21 | 2.8 |
| 22 | 31.46 |
| 23 | 5.3 |
| 24 | 0.7 |
| 26 | 4.1 |
| 30 | 4.5 |
| 31 | 9.7 |
| 32 | 4.8 |
| 35 | 204 |
| 38 | 17.8 |
| 39 | 1.7 |
| 40 | 8 |
| 43 | 7.3 |
| 44 | 4.8 |
| 46 | 6 |
| 47 | 9 |
| 50 | 20.8 |

TABLE 2-continued

In vitro EC50 values of the GPR 40 agonists of the present invention in Luciferase assay.

| Compound # | $EC_{50}$ (nM) |
|---|---|
| 51 | 3.0 |
| 55 | 56.5 |
| 58 | 3.7 |
| 60 | 5.6 |
| 61 | 12.6 |
| 62 | 3.0 |
| 63 | 4.4 |
| 64 | 1.2 |
| 65 | 1.6 |
| 68 | 11.9 |
| 69 | 0.8 |
| 71 | 0.4 |
| 72 | 2.3 |

Most of the compounds of the present invention were evaluated against CYP1A2, CYP2C8, CYP2C9, CYP2C19, CYP2D6 and CYP3A4 and there was no significant CYP inhibitory effect. The compounds did not show significant hERG binding at 10 µM.

In Vivo Efficacy Studies:

Primary Screening Protocol for GRP40 agonist test compounds in n-STZ rat model

Wistar rat pups of 1-2 day old injected with Streptozotocin (STZ) at 120 mg/kg dose by intraperitoneal route. All pups allowed grow normally and at the age of 12-14 week they were screen for glucose intolerance by performing the oral glucose tolerance test by tail clip method using glucometer. Animals showing glucose intolerance were selected for evaluation of test compound. Three to seven days of rest period animals were kept on overnight fasting. Next day morning blood glucose levels measured using glucometer and animals were grouped such that their pretreatment glucose levels were not significantly different between groups. Animals were administered with test compound and then 15-60 min after the compound administration "O" min blood glucose levels were measured and immediately glucose load at 2 g/kg was administered orally. Blood glucose levels were measured at 30, 60 and 120 min after glucose load using by tail clip method using glucometer. Blood was also collected at 10 min after glucose load for measurement of insulin levels. Glucose area under the curve (AUC) was calculated using Graph Pad Prism software and % reduction in AUC-glucose vs vehicle treated control was calculated (Table 3).

TABLE 3

Efficacy of the GPR 40 agonist of the present invention in n-STZ rat model

| Compound | Dose (per oral) | % improvement in AUC glucose vs. control |
|---|---|---|
| 7 | 0.1 mg/Kg | 30.4 |
|   | 1 mg/Kg | 46.0 |
|   | 10 mg/Kg | 57.0 |
| 10 | 0.1 mg/Kg | 21.1 |
|   | 1 mg/Kg | 35.7 |
|   | 10 mg/Kg | 45.0 |
| 16 | 1 mg/Kg | 44.6 |
|   | 10 mg/Kg | 59.6 |
| 17 | 1 mg/Kg | 37.1 |
|   | 10 mg/Kg | 44.7 |
| 60 | 1 mg/Kg | 44 |
|   | 10 mg/Kg | 47 |
| 64 | 1 mg/Kg | 46 |
|   | 10 mg/Kg | 47 |

In the n-STZ rat OGTT model the $ED_{50}$ of compounds 16, 60 & 64 has been found 0.05 mg/Kg, 0.04 mg/Kg & 0.09 mg/Kg respectively.

Few compounds have exhibited significant pharmacokinetics parameters in rats (Table 4)

TABLE 4

Pharmacokinetics parameters of compounds 16, 60 & 64

| Parameters | 16 | 60 | 64 |
|---|---|---|---|
| Dose (po) mg/Kg | 3 | 3 | 3 |
| $T_{max}$ (h) | 0.25 | 1 | 2 |
| $C_{max}$ (µg/mL) | 5.92 ± 2.10 | 7.77 ± 1.94 | 8.06 ± 2.19 |
| AUC (0-t) | 7.63 ± 127 | 52.52 ± 12.62 | 82.42 ± 27.63 |
| $T_{1/2}$, po (h) | 1.77 ± 0.42 | 5.45 ± 0.79 | 4.51 ± 0.61 |
| Mean residence time (h) | 2.19 ± 0.31 | 5.74 ± 0.10 | 6.59 ± 0.93 |
| iv dose (mg/Kg) | 1 | 1 | 1 |
| $C_0$ (µg/mL) | 5.02 ± 0.37 | 3.39 ± 0.33 | 10.16 ± 1.54 |
| AUC (0-t) (µg · h/mL) | 3.18 ± 0.40 | 18.61 ± 2.17 | 56.14 ± 4.35 |
| Vss (L/Kg) | 0.34 ± 0.03 | 0.33 ± 0.01 | 0.16 ± 0.01 |
| CL (mL/min./Kg) | 5.26 ± 0.65 | 0.89 ± 0.10 | 0.27 ± 0.03 |
| $T_{1/2}$, iv (h) | 1.45 ± 0.12 | 5.57 ± 1.46 | 7.77 ± 1.07 |
| Mean residence time (h) | 1.09 ± 0.07 | 6.28 ± 0.77 | 10.07 ± 1.36 |
| % F | 83 | 93 | 45 |

The compounds of formula (I) or pharmaceutical compositions containing them are suitable for humans and other warm blooded animals, and may be administered either by oral, topical or parenteral administration for the treatment of various disease conditions associated with dyslipidemia, obesity etc.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The invention claimed is:

1. A compound of general Formula (I')

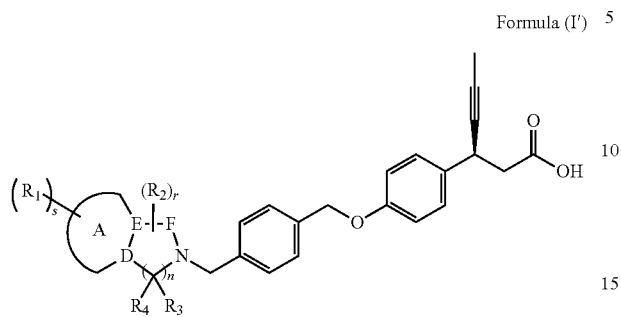

Formula (I')

a tautomeric form thereof, a stereoisomer thereof, or a pharmaceutically acceptable salt thereof, wherein each of $R_1$, $R_2$, $R_3$ and $R_4$ at each occurrence independently represents H, halogen, hydroxyl, CN, $NO_2$, CHO, COOH, CO, alkyl, alkoxy, thiol, sulphoxide, sulphone, acyl, $NH_2$, NHCO-linear or branched ($C_1$-$C_6$)alkyl, aralkyl, cycloalkyl, cycloalkylalkyl, heterocyclyl, hetererocyclylalkyl, heteroaryl, or heteroaralkyl or a group OR, C(O)OR, C(O)R, or $SO_2R$ wherein R at each occurrence is independently selected from H, linear or branched ($C_1$-$C_6$)alkyl, aryl, aralkyl, cycloalkyl, cycloalkylalkyl, heterocyclyl, hetrerocyclylalkyl, heteroaryl, and heteroaralkyl groups;

A is selected from 5 or 6 membered heteroaromatic rings which may further have one or more heteroatoms selected from O, S, and N;

each of E and D independently represents either nitrogen or carbon;

F is selected from C, N and O; and each of n, r, and s independently represents an integer ranging from 0 to 6.

2. The compound as claimed in claim 1, wherein the heterocycle representing

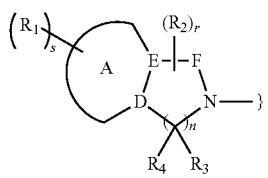

is selected from the group consisting of

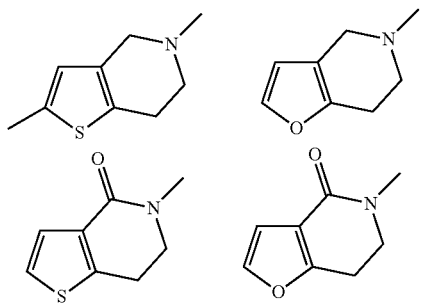

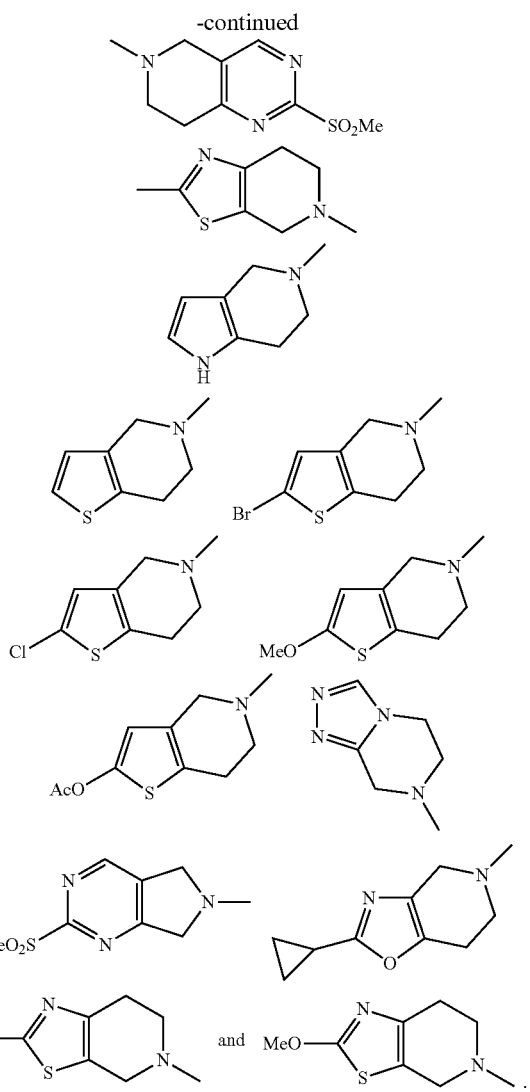

3. The compound as claimed in claim 1, wherein the COOH is replaced wherever possible with bioisosteric replacements selected from the group consisting of

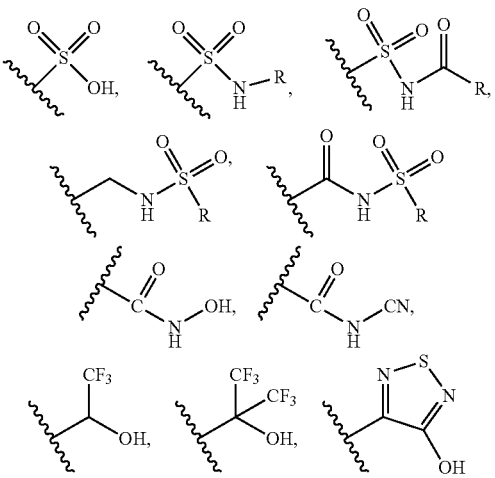

-continued

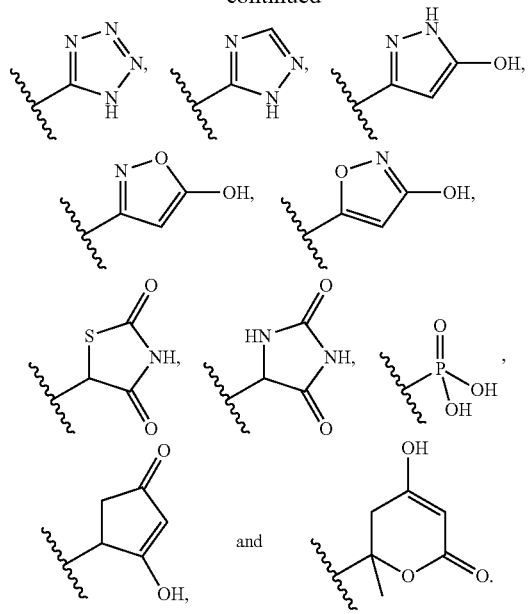

4. The compound according to claim 1 selected from the group consisting of
- (S)-3-(4-((3-((6,7-dihydrothieno[3,2-c]pyridin-5(4H)-yl) methyl)benzyl)oxy)phenyl)hex-4-ynoic acid;
- (S)-3-(4-((3-((2-methyl-6,7-dihydrothienazolo[5,4-c] pyridin-5(4H)-yl)methyl)benzyl)oxy) phenyl)hex-4-ynoic acid;
- (S)-3-(4-((3-((1-(tert-butoxycarbonyl)-6,7-dihydro-1H-pyrrolo[3,2-c]pyridin-5(4H)-yl) methyl)benzyl)oxy) phenyl)hex-4-ynoic acid;
- (S)-3-(4-((3-((6,7-dihydro-1H-pyrrolo[3,2-c]pyridin-5 (4H)-yl)methyl)benzyl)oxy)phenyl) hex-4-ynoic acid;
- (S)-3-(4-((3-((2-methyl-6,7-dihydrothiazolo[5,4-c]pyridin-5(4H)-yl)methyl)benzyl)oxy) phenyl)hex-4-ynoic acid;
- (S)-3-(4-((3-((3-(trifluoromethyl)-5,6-dihydro-[1,2,4]triazolo[4,3-a]pyrazin-7(8H)-yl) methylbenzyl)oxy)phenyl)hex-4-ynoic acid;
- (S)-3-(4-((3-((2-bromo-6,7-dihydrothieno[3,2-c]pyridin-5(4H)-yl)methyl)benzyl)oxy) phenyl)hex-4-ynoic acid;
- calcium(S)-3-(4-((3-((2-methyl-6,7-dihydrothieno[3,2-c] pyridin-5(4H)-yl)methyl) benzyl)oxy)phenyl)hex-4-ynoate(S)-3-(4-((3-((2-methyl-6,7-dihydrothieno[3,2-c]pyridin-5 (4H)-yl)methyl)benzyl)oxy)phenyl)hex-4-ynoate;
- calcium(S)-3-(4-((3-((2-methyl-6,7-dihydrothiazolo[4,5-c]pyridin-5(4H)-yl)methyl) benzyl)oxy)phenyl)hex-4-ynoate(S)-3-(4-((3-((2-methyl-6,7-dihydrothiazolo[4,5-c]pyridin-5(4H)-yl)methyl)benzyl)oxy)phenyl)hex-4-ynoate;
- (S)-3-(4-((3-((2-(Difluoromethyl)-6,7-dihydrothieno[3,2-c]pyridin-5(4H)-yl)methyl) benzyl)oxy)phenyl)hex-4-ynoic acid;
- Calcium (S)-3-(4-((3-((2-bromo-6,7-dihydrothieno[3,2-c] pyridin-5(4H)-yl)methyl) benzyl)oxy)phenyl)hex-4-ynoate;
- (S)-3-(4-((3-((7,8-Dihydropyrido[4,3-d]pyrimidin-6(5H)-yl)methyl)benzyl)oxy)phenyl) hex-4-ynoic acid;
- (S)-3-(4-((3-((1-Methylpyrrolo[3,4-c]pyrazol-5(1H,4H,6H)-yl)methyl)benzyl)oxy)phenyl) hex-4-ynoic acid;
- (S)-3-(4-((3-((5,6-Dihydro-[1,2,4]triazolo[4,3-a]pyrazin-7(8H)-yl)methyl)benzyl)oxy) phenyl)hex-4-ynoic acid;
- (S)-3-(4-((3-((2-Cyclopropyl-6,7-dihydrooxazolo[4,5-c] pyridin-5(4H)-yl)methyl)benzyl) oxy)phenyl)hex-4-ynoic acid;
- (S)-3-(4-((3-((4H-Thieno[2,3-c]pyrrol-5(6H)-yl)methyl) benzyl)oxy)phenyl)hex-4-ynoic acid;
- 6-(3-((4-((S)-1-carboxypent-3-yn-2-yl)phenoxy)methyl) benzyl)-6,7-dihydro-5H-pyrrolo[3,4-d]pyrimidin-6-ium formate;
- (S)-3-(4-((3-((2-Chloro-6,7-dihydrothiazolo[5,4-c]pyridin-5(4H)-yl)methyl)benzyl)oxy) phenyl)hex-4-ynoic acid;
- (S)-3-(4-((3-((2-Bromo-6,7-dihydrothiazolo[5,4-c]pyridin-5(4H)-yl)methyl)benzyl)oxy) phenyl)hex-4-ynoic acid;
- (S)-3-(4-((3-(pyrrolo[3,4-c]pyrazol-5(1H,4H,6H)-ylmethyl)benzyl)oxy)phenyl)hex-4-ynoic acid;
- (S)-3-(4-((3-((2-(hydroxymethyl)-6,7-dihydrothieno[3,2-c]pyridin-5(4H)-yl)methyl) benzyl)oxy)phenyl)hex-4-ynoic acid;
- (S)-5-(3-((4-(1-carboxypent-3-yn-2-yl)phenoxy)methyl) benzyl)-4,5,6,7-tetrahydrothieno[3,2-c]pyridine-2-carboxylic acid;
- 3-cyclopropyl-3-(3-((3-((2-methyl-6,7-dihydrothieno[3,2-c]pyridin-5(4H)-yl)methyl) benzyl)oxy)phenyl)propanoic acid;
- (S)-3-(4-((3-((1-methyl-6,7-dihydro-1H-pyrrolo[3,2-c] pyridin-5(4H)-yl)methyl) benzyl)oxy)phenyl)hex-4-ynoic acid;
- (S)-3-(4-((3-((2-amino-6,7-dihydrothiazolo[5,4-c]pyridin-5(4H)-yl)methyl)benzyl)oxy) phenyl)hex-4-ynoic acid;
- Calcium (S)-3-(4-((3-((2-chloro-6,7-dihydrothieno[3,2-c] pyridin-5(4H)-yl)methyl) benzyl)oxy)phenyl)hex-4-ynoate;
- (S)-3-(4-((3-((2-carbamoyl-6,7-dihydrothieno[3,2-c]pyridin-5(4H)-yl)methyl)benzyl)oxy) phenyl)hex-4-ynoic acid;
- (S)-3-(4-((3-((2-isopropylpyrrolo[3,4-c]pyrazol-5(2H,4H,6H)-yl)methyl)benzyl)oxy) phenyl)hex-4-ynoic acid;
- (S)-3-(4-((3-((2-(methoxycarbonyl)-6,7-dihydrothieno[3,2-c]pyridin-5(4H)-yl)methyl) benzyl)oxy)phenyl)hex-4-ynoic acid;
- (S)-3-(4-((3-((2-cyano-6,7-dihydrothieno[3,2-c]pyridin-5 (4H)-yl)methyl)benzyl)oxy) phenyl)hex-4-ynoic acid;
- (S)-3-(4-((3-((2-formyl-6,7-dihydrothieno[3,2-c]pyridin-5(4H)-yl)benzyl oxy)phenyl)hex-4-ynoic acid;
- S)-3-(4-((3-((2-methyl-6,7-dihydropyrazolo[1,5-a] pyrazin-5(4H)-yl)methyl)benzyl) oxy)phenyl)hex-4-ynoic acid;
- (S)-3-(4-((3-((2-(methylcarbamoyl)-6,7-dihydrothieno[3,2-c]pyridin-5(4H)-yl)methyl) benzyl)oxy)phenyl)hex-4-ynoic acid;
- (S)-3-(4-((3-((2-(dimethylcarbamoyl)-6,7-dihydrothieno [3,2-c]pyridin-5(4H)-yl)methyl) benzyl)oxy)phenyl) hex-4-ynoic acid;
- (S)-3-(4-((3-((2-(Methylsulfonyl)-7,8-dihydropyrido[4,3-d]pyrimidin-6(5H)-yl)methyl) benzyl)oxy)phenyl)hex-4-ynoic acid;
- (S)-3-(4-((3-((2-Methoxy-7,8-dihydropyrido[4,3-d]pyrimidin-6(5H)-yl)methyl)benzyl) oxy)phenyl)hex-4-ynoic acid;
- (S)-3-(4-((3-((1-isopropylpyrrolo[3,4-c]pyrazol-5(1H,4H,6H)-yl)methyl)benzyl)oxy) phenyl)hex-4-ynoic acid compound with formic acid;

(R)-3-(4-((3-((2-methyl-6,7-dihydrothieno[3,2-c]pyridin-5(4H)-yl)methyl)benzyl) oxy)phenyl)hex-4-ynoic acid;
(R)-3-(4-((3-((2-Methyl-6,7-dihydrothiazolo[5,4-c]pyridin-5(4H)-yl)methyl)benzyl) oxy)phenyl)hex-4-ynoic acid;
(S)-3-(4-((3-((6,7-Dihydro-[1,2,3]triazolo[1,5-a]pyrazin-5(4H)-yl)methyl)benzyl)oxy) phenyl)hex-4-ynoic acid;
3-(4-((3-((2-Methyl-6,7-dihydrothieno[3,2-c]pyridin-5 (4H)-yl)methyl)benzyl)oxy) phenyl)hex-4-ynoic acid;
3-(4-((3-((2-Methyl-6,7-dihydrothiazolo[5,4-c]pyridin-5 (4H)-yl)methyl)benzyl)oxy) phenyl)hex-4-ynoic acid;
Calcium (S)-3-(4-((3-((2-chloro-6,7-dihydrothiazolo[5,4-c]pyridin-5(4H)-yl)methyl) benzyl)oxy)phenyl)hex-4-ynoate;
(S)-3-(4-((3-((2-(cyclopropylcarbamoyl)-6,7-dihydrothieno[3,2-c]pyridin-5(4H)-yl)methyl)benzyl)oxy)phenyl)hex-4-ynoic acid;
(S)-3-(4-((3-((2-(pyrrolidine-1-carbonyl)-6,7-dihydrothieno[3,2-c]pyridin-5(4H)-yl)methyl)benzyl)oxy)phenyl)hex-4-ynoic acid;
(S)-3-(4-((3-((2-acetamido-6,7-dihydrothieno[3,2-c]pyridin-5(4H)-yl)methyl)benzyl) oxy)phenyl)hex-4-ynoic acid;
Calcium (S)-3-(4-((3-((2-cyclopropyl-6,7-dihydrooxazolo[4,5-c]pyridin-5(4H)-yl)methyl) benzyl)oxy)phenyl)hex-4-ynoate;
(S)-3-(4-((3-((2-Nitro-6,7-dihydrothieno[3,2-c]pyridin-5 (4H)-yl)methyl)benzyl) oxy)phenyl)hex-4-ynoic acid;
(S)-3-(4-((3-((2-(Dimethylamino)-7,8-dihydropyrido[4,3-d]pyrimidin-6(5H)-yl)methyl)benzyl)oxy)phenyl) hex-4-ynoic acid compound with 2,2,2-trifluoroacetic acid;
(S)-3-(4-((3-((2-Amino-7,8-dihydropyrido[4,3-d]pyrimidin-6(5H)-yl)methyl)benzyl)oxy)phenyl)hex-4-ynoic acid compound with 2,2,2-trifluoroacetic acid;
(S)-3-(4-((3-((7,8-Dihydro-1,6-naphthyridin-6(5H)-yl) methyl)benzyl)oxy)phenyl)hex-4-ynoic acid;
(S)-3-(4-((3-((2-Cyclopropyl-6,7-dihydrothieno[3,2-c] pyridin-5(4H)-yl)methyl)benzyl)oxy)phenyl)hex-4-ynoic acid compound with 2,2,2-trifluoroacetic acid;
(S)-3-(4-((3-((2-Acetamido-6,7-dihydrothiazolo[5,4-c] pyridin-5(4H)-yl)methyl) benzyl)oxy)phenyl)hex-4-ynoic acid compound with 2,2,2-trifluoroacetic acid;
(S)-3-(4-((3-((2-Ethyl-6,7-dihydrothieno[3,2-c]pyridin-5 (4H)-yl)methyl)benzyl) oxy)phenyl)hex-4-ynoic acid;
(S)-3-(4-((3-((2-Acetyl-6,7-dihydrothieno[3,2-c]pyridin-5(4H)-yl)methyl)benzyl) oxy)phenyl)hex-4-ynoic acid; and
(S)-3-(4-((3-((2-((Methylamino)methyl)-6,7-dihydrothieno[3,2-c]pyridin-5(4H)-yl)methyl)benzyl)oxy)phenyl)hex-4-ynoic acid compound with 2,2,2-trifluoroacetic acid.

5. A pharmaceutical composition comprising a therapeutically effective amount of a compound of Formula (I') as claimed in claim 1 and optionally one or more pharmaceutically acceptable carriers, diluents or excipients.

6. A pharmaceutical composition comprising a therapeutically effective amount of a compound of Formula (I') as claimed in claim 4 and optionally one or more pharmaceutically acceptable carriers, diluents or excipients.

* * * * *